United States Patent
Sim et al.

(10) Patent No.: US 6,852,847 B1
(45) Date of Patent: Feb. 8, 2005

(54) CANINE AND FELINE B7-2 NUCLEIC ACID MOLECULES AND USES THEREOF

(75) Inventors: Gek-Kee Sim, Fort Collins, CO (US); Shumin Yang, Palo Alto, CA (US); Karen S. Sellins, Fort Collins, CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 09/646,561

(22) PCT Filed: Mar. 19, 1999

(86) PCT No.: PCT/US99/06187

§ 371 (c)(1),
(2), (4) Date: Feb. 1, 2001

(87) PCT Pub. No.: WO99/47558

PCT Pub. Date: Sep. 23, 1999

(Under 37 CFR 1.47)

Related U.S. Application Data

(63) Continuation-in-part of application No. 09/062,597, filed on Apr. 17, 1998, now abandoned.
(60) Provisional application No. 60/078,765, filed on Mar. 19, 1998.

(51) Int. Cl.[7] .................. C07H 21/04; C12N 15/09; C12N 15/12; C12N 15/63
(52) U.S. Cl. .................. 536/23.5; 536/23.1; 514/44; 435/69.1; 435/455; 435/252.3; 435/320.1
(58) Field of Search ................. 536/23.1, 23.5; 514/44; 435/69.1, 455, 252.3, 320.1

(56) References Cited

U.S. PATENT DOCUMENTS 6,337,316 B1 * 1/2002 El Tayar et al.

2002/0028208 A1 * 3/2002 Collisson et al.

OTHER PUBLICATIONS

Lemer Nature 1982; 299:592–596.*
Coyle et al. Nature Immunol. 2:203–209 2001.*
Metzler et al. Nature Structural Biol. 1997;4:527–531.*
Maher et al. J. Immunol. 157:3838–3844, 1996; 1449.*
Branch TIBS 1998; 23:45–50.*
Mountain TIBTECH 18:119–128 2000.*
Voet et al. In Biochemistry. John Wiley & Sons. 1990, vol. 1, pp. 126–128, and p. 230.*
EMBL Accession No. U57755 Felis catus T–cell specific surface glycoprotein B7–1 mRNA, complete cds., Release date May 20, 1997.
Hash, S.M. *Cloning, Sequencing, Expression and Characterization of the Feline CD28/CD80 Accessory Signaling Complex*. Dissertation, Veterinary Microbiology, Texas A&M University, May, 1997.
Yang, S. et al. "Cloning of Genes Encoding Canine Co–Stimulatory Molecules" Annual Meeting of the Professional Research Scientists on Experimental Biology, part II, San Francisco, USA, Apr. 18–22, 1998. *FASEB Journal for Experimental Biology* 12(5):a940, No. 5444 (Mar. 1998).

* cited by examiner

*Primary Examiner*—Phillip Gambel
*Assistant Examiner*—Jessica H. Roark
(74) *Attorney, Agent, or Firm*—Heska Corporation

(57) ABSTRACT

The present invention relates to canine and feline B7 proteins; to B7 nucleic acid molecules, including those that encode such B7 proteins; to antibodies raised against such B7 proteins; and to therapeutic compounds that regulate B7 function. The present invention also includes methods to identify and obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to regulate an immune response in an animal.

18 Claims, No Drawings

CANINE AND FELINE B7-2 NUCLEIC ACID MOLECULES AND USES THEREOF

CROSS-REFERENCE TO RELATED APPLICATIONS

This application claims priority to international PCT Application No. PCT/US99/06187, filed Mar. 19, 1999; which is a continuation-in-part of U.S. application Ser. No. 09/062,597, filed Apr. 17, 1998 now abandoned; which claims priority to U.S. Provisional Application Ser. No. 60/078,765, filed Mar. 19, 1998.

FIELD OF THE INVENTION

The present invention relates to B7 and CILA4 nucleic acid molecules, proteins encoded by such nucleic acid molecules, antibodies raised against such proteins and inhibitors of such proteins or nucleic acid molecules. The present invention also includes therapeutic compositions comprising such nucleic acid molecules, proteins, antibodies and/or inhibitors, as well as their use to regulate an immune response in an animal.

BACKGROUND OF INVENTION

T lymphocytes (i.e., T cells) play a key role in regulating immune responses in animals. Activation of T cells requires two signals delivered by antigen presenting cells to non-activated T cells. The first, or primary, signal is mediated by the interaction of the T cell receptor/CD3 complex (TcR/CD3) with MHC-associated antigenic peptide. The second, or costimulatory, signal regulates the T cell proliferative response and induction of effector functions. Costimulatory signals determine whether a T cell will be activated or inactivated to a state of tolerance. Molecules present on the surface of antigen presenting cells which are involved in T cell costimulation include B7 molecules. As known in the arts B7 molecules include two forms, B7-1 and B7-2, also known as CD80 and CD86, respectively. These molecules are counter-receptors for two ligands, CD28 and CTLA4. Both B7-1 and B7-2 bind both CD28 and CTLA4. Upon binding to CD28 or CTLA4, mouse B7 can cause T cells to proliferate and secrete interleukin-2 in conjunction with engagement of T cell receptor with a major histocompatability molecule complexed with peptide.

A full-length B7 protein is composed of several regions including, from the N-terminus, a signal peptide, an extracellular region, a transmembrane region, and a cytoplasmic region. The predicted amino acid sequence of B7-1 shares homology with members of the immunoglobulin (Ig) superfamily due to the presence of two contiguous Ig-like domains in the extracellular region For example, in the mature mouse B7-1 protein, residues 1–112 share homology with the Ig variable (IgV) domain and residues 113–210 shares homology with Ig constant (gC) domain (Freeman et al., J. Immunol., Vol. 143, pp. 2714–2722, 1989). B7-2 was also found to have similar structural features in the extracellular region. Similarly, CD28 and CTLA4 each have one IgV-like domain in the extracellular region.

Prior investigators have disclosed sequences encoding: human B7-1 domains are encoded by distinct exons in their respective genes as described for human B7-1 (Freeman et at., J. Immunol., vol. 143, pp. 2714–2722, 1989); human B7 (Azuma et al., Nature, vol. 366, pp. 76–79, 1993; or Selvakumar et al., Immunogenetics., vol. 36, pp. 175–181, 1992); rhesus monkey B7-1 (Villinger et al., J. Immunol., vol. 155, pp. 3946–3954, 1995); cat B7-1 (Hash et al., Thesis, Veterinary Pathobiology, Texas A & M, 1996); rabbit B7-1 (Isono et al., Immunogenetics., vol. 42, pp. 217–220, 1995); rat B7-1 (Judge et al., Intl. Immunol., vol. 7, pp. 171–178, 1995; Jackerott et al., Genbank Accession No. U10925, 1994); mouse B7-1 (Borriello et al., J. Immunol, vol. 153, pp. 5038–5048, 1994); human B7-2 (Freeman et al., Science, vol. 262, pp. 909–911, 1993); mouse B7-2 freeman et al., J. Expt. Med, vol. 178, pp. 2185–2192, 1993; or) and rat B7 genes (Judge et al., Intl. Immunol., vol, 7, pp. 171–178, 1995; Goodman, Genbank Accession No. U31330, 1995).

Prior investigators have also disclosed sequences encoding: mouse CTLA4 (Brunet et al., Nature, vol. 328, pp. 267–270, 1987); human CTLA4 (Dariavach et al., Eur J Immunol, vol 18, pp. 1901–1905, 1988); rabbit CTLA4 (Isono and Seto, Immunogenetics, vol. 42, pp. 217–220, 1995); rat CTLA4 (Oaks et al., Immunogenetics, vol. 43, pp. 173–174, 1996); and bovine CTLA4 (Parsons et al. Immunogenetics, vol. 43, pp. 388–391, 1996).

Messenger RNA of different sizes have been identified for B7-2 genes by Northern blot hybridization (Inobe et al., Biochem. Biophys. Res. Communic., vol. 200, pp. 443–449, 1994; or Boriello et al., J. Immunol., vol. 155, pp. 5490–5497, 1995). These B7-2 mRNA species have been assumed to be generated through alternative splicing or differential use of polyadenylation sites.

There remains a need for compounds and methods to regulate an immune response by manipulation of the function of B7-1 and/or B7-2.

SUMMARY OF THE INVENTION

The present invention relates to B7 and CTLA4 nucleic acid molecules, proteins encoded by such nucleic acid molecules, antibodies raised against such proteins and inhibitors of such proteins or nucleic acid molecules. The inventors have discovered novel naturally-occuring variants of B7 proteins that are produced by, for example, alternative RNA splicing or alternative termination of full-length amino acid sequence. The inventors are the first to discover such variants and therefore disclose novel therapeutic compositions and methods to use such variants to regulate an immune response in an animal useful in the treatment of diseases including cancer, infectious diseases, inflammation or allergy. Thus, the present invention also includes therapeutic compositions comprising such nucleic acid molecules, proteins, antibodies and/or inhibitors, as well as their use to regulate an immune response in an animal.

One embodiment of the present invention is an isolated nucleic acid molecule having a nucleic acid sequence that is at least about 80 percent identical to a nucleic acid sequence selected from the group consisting of SEQ ID NO:1, SEQ ED NO:3, SEQ ID NO:4, SEQ ID NO:5, SEQ ID NO:6, SEQ ID NO:8, SEQ ID NO:9, SEQ ID NO: 10, t. SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ I NO:25, SEQ ID NO:27, SEQ ID NO:28 and SEQ ID NO:29, or a fragment thereof having at least 12 nucleotides.

Another embodiment of the present invention is an isolated nucleic acid molecule consisting of a nucleic acid sequence selected from the group consisting of SEQ ID NO:36, SEQ ID NO-38, SEQ ID NO:39, and SEQ ID NO:40.

Another embodiment is a nucleic acid molecule having a nucleic acid sequence that is at least about 90 percent identical to a nucleic acid sequence selected from the group consisting of SEQ ID NO:41, SEQ ID NO:43, SEQ ID NO:44, SEQ ID NO:45, SEQ ID NO:46, SEQ ID NO:48, SEQ ID NO:49, SEQ ID NO:50, or a fragment thereof having at least about 12 nucleotides.

Another embodiment of the present invention is an isolated nucleic acid molecule selected from the group consisting of: (a) a nucleic acid molecule having a nucleic acid sequence encoding a B7 protein selected from the group consisting of a protein having an amino acid sequence that is at least about 80 percent identical to the amino acid sequence SEQ ID NO:2, a protein comprising an epitope of said protein having an amino acid sequence that is at least about 80 percent identical to the amino acid sequence SEQ ID NO:2, a protein having an amino acid sequence that is at least about 60 percent identical to the amino acid sequence SEQ ID NO:7, a protein comprising an epitope of said protein having an amino acid sequence that is at least about 60 prevent identical to the amino acid sequence SEQ ID NO:7, a protein having an amino acid sequence that is at least about 80 percent identical to the amino acid sequence SEQ ID NO: 12, a protein comprising an epitope of said protein having an amino acid sequence that is at least about 80 percent identical to the amino acid sequence SEQ ID NO: 12, a protein having an amino acid sequence that is at least about 60 percent identical to the amino acid sequence SEQ ID NO: 17, a protein comprising an epitope of said protein having an amino acid sequence that is at least about 60 percent identical to the amino acid sequence SEQ ID NO:17, a protein having an amino acid sequence that is at least about 60 percent identical to the amino acid sequence SEQ ID NO:26, a protein comprising an epitope of said protein having an amino acid sequence that is at least about 60 percent identical to the amino acid sequence SEQ ID NO:26, a protein having an amino acid sequence that is at least about 80 percent identical to the amino acid sequence SEQ ID NO:34, a protein comprising an epitope of said protein having an amino acid sequence that is at least about 80 percent identical to the amino acid sequence SEQ ID NO:34, and a protein having amino acid sequence SEQ ID NO:37; (b) a nucleic acid molecule comprising a complement of any of said nucleic acid sequences set forth in (a); (c) a nucleic acid molecule having a nucleic acid sequence encoding a CTLA4 protein selected from the group consisting of: a protein having an amino acid sequence that is at least about 90 percent identical to an amino acid sequence selected from the group consisting of SEQ ID NO:42 and SEQ ID NO:47; and a protein comprising an epitope of said protein having an amino acid sequence that is at least about 90 percent identical to an amino acid sequence selected from the group consisting of SEQ ID NO:42 and SEQ ID NO:47; and (d) a nucleic acid molecule comprising a complement of any of said nucleic acid sequences set forth in (c); wherein said B7 protein elicits an immune response against a naturally-occuring B7 protein, and wherein said CTLA4 protein elicits an immune response against a naturally-occuring CTLA4 protein.

The present invention also includes methods to produce B7 proteins recombinantly using such nucleic acid molecules.

Yet another embodiment of the present invention is an isolated nucleic acid molecule that encodes a naturally-occuring soluble mammalian B7 protein, and complements thereof. A preferred nucleic acid molecule includes a nucleic acid molecule comprising a nucleic acid sequence encoding a naturally-occuring soluble B7-2 protein having extracellular and intracellular domains but lacking at least a portion of the transmembrane domain sufficient to produce a soluble protein upon translation of the nucleic acid molecule in a suitable host cell. Another preferred nucleic acid molecule includes a nucleic acid molecule comprising a nucleic acid sequence encoding a naturally-occuring soluble B7-1 protein having an extracellular domain but lacking at least a portion of the transmembrane and intracellular domains sufficient to produce a soluble protein upon translation of the nucleic acid molecule in a suitable host cell. Yet another preferred nucleic acid molecule comprises a nucleic acid sequence encoding a naturally-occuring soluble feline B7-1 protein having an extracellular domain but lacking at least a portion of transmembrane and intracellular domains sufficient to produce a soluble protein upon translation of said nucleic acid molecule in a suitable host cell, wherein said extracellular domain comprises an IgV-like domain, but lacks an IgC-like domain.

The present invention also includes (a) an isolated protein comprising a B7 protein selected from the group consisting of a protein having an amino acid sequence that is at least about 80 percent identical to the amino acid sequence SEQ ID NO:2, a protein comprising an epitope of said protein having an amino acid sequence that is at least about 80 percent identical to the amino acid sequence SEQ ID NO:2, a protein having an amino acid sequence that is at least about 60 percent identical to the amino acid sequence SEQ ID NO:7, a protein comprising an epitope of said protein having an amino acid sequence that is at least about 60 percent identical to the amino acid sequence SEQ ID NO:7, a protein having an amino acid sequence that is at least about 80 percent identical to the amino acid sequence SEQ ID NO: 12, a protein comprising an epitope of said protein having an amino acid sequence that is at least about 80 percent identical to the amino acid sequence SEQ ID NO:12, a protein having an amino acid sequence that is at least about 60 percent identical to the amino acid sequence SEQ ID NO:17, a protein comprising an epitope of said protein having an amino acid sequence that is at least about 60 percent identical to the amino acid sequence SEQ ID NO:17, a protein having an amino acid sequence that is at least about 60 percent identical to the amino acid sequence SEQ ID NO:26, a protein comprising an epitope of said protein having an amino acid sequence that is at least about 60 percent identical to the amino acid sequence SEQ ID NO:26, a protein having an amino acid sequence that is at least about 80 percent identical to the amino acid sequence SEQ ID NO:34, a protein comprising an epitope of said protein having an amino acid sequence that is at least about 80 percent identical to the amino acid sequence SEQ ID NO:34, and a protein consisting of amino acid sequence SEQ ID NO:37, wherein said B7 protein elicits an immune response against a naturally occurring B7 protein; and (b) an isolated protein comprising a CTLA4 protein selected from the group consisting of: a protein having an amino acid sequence that is at least about 90 percent identical to an amino acid sequence selected from the group consisting of SEQ ID NO:42 and SEQ ID NO:47; and a protein comprising an epitope of said protein having an amino acid sequence that is at least about 90 percent identical to an amino acid sequence selected from the group consisting of SEQ ID NO:42 and SEQ ID NO:47; wherein said CTLA4 protein elicits an immune response against a naturally-occuring CTLA4 protein.

The present invention also includes an isolated naturally-occuring soluble mammalian B7 protein. A preferred naturally-occuring soluble mammalian B7 protein comprises an isolated naturally-occuring soluble B7-2 protein comprising extracellular and intracellular domains but lacking at least a portion of the transmembrane domain of the B7-2 protein sufficient to be a soluble B7-2 protein. Another preferred naturally-occuring soluble mammalian B7 protein comprises an isolated naturally-occuring soluble B7-1 protein comprising the extracellular domain but lacking at least a portion of the transmembrane and intracellular domains of the B7-1 protein sufficient to produce a soluble B7-1 protein. Another preferred naturallyocumng soluble mammalian B7 protein comprises an isolated naturally-occuring soluble feline B7-1 protein having an extracellular domain but lacking at least a portion of transmembrane and intracellular domains sufficient to produce a soluble protein upon translation of said nucleic acid molecule in a suitable host cell, wherein said extracellular domain comprises an IgV-like domain, but lacks an IgC-like domain.

One aspect of the present invention is a therapeutic composition that, when administered to an animal, regulates T cell mediated immune responses in said animal, said therapeutic composition comprising a therapeutic compound selected from the group consisting of:an isolated protein comprising a B7 protein, wherein said B7 protein is selected from the group consisting of a protein having an amino acid sequence that is at least about 80 percent identical to the amino acid sequence SEQ ID NO:2, a protein comprising an epitope of said protein having an amino acid sequence that is at least about 80 percent identical to the amino acid sequence SEQ ID NO:2, a protein having an amino acid sequence that is at least about 60 percent identical to the amino acid sequence SEQ ID NO:7, a protein comprising an epitope of said protein having an amino acid she that is at least about 60 percent identical to the amino acid sequence SEQ ID NO:7, a protein having an amino acid sequence that is at least about 80 percent identical to the amino acid sequence SEQ ID NO:12, a protein comprising an epitope of said protein having an amino acid sequence that is at least about 80 percent identical to the amino acid sequence SEQ ID NO:12, a protein having an amino acid sequence that is at least about 60 percent identical to the amino acid sequence SEQ ID NO:17, a protein comprising an epitope of said protein having an amino acid sequence that is at least about 60 percent identical to the amino acid sequence SEQ ID NO:17, a protein having an amino acid sequence that is at least about 60 percent identical to the amino acid sequence SEQ ID NO:26, a protein comprising an epitope of said protein having an amino acid sequence that is at least about 60 percent identical to the amino acid sequence SEQ ID NO:26, a protein having an amino acid sequence that is at least about 80 percent identical to the amino acid sequence SEQ ID NO:34, a protein comprising an epitope of said protein having an amino acid sequence that is at least about 80 percent identical to the amino acid sequence SEQ ID NO:34, a protein having amino acid sequence SEQ ID NO:37, an isolated naturally-occuring soluble B7 protein; a mimetope of any of said B7 proteins; a multimeric form of any of said B7 proteins; an isolated protein comprising a CTLA4 protein selected from the group consisting of: a protein having an amino acid sequence that is at least about 90 percent identical to an amino acid sequence selected from the group consisting of SEQ ID NO:42 and SEQ ID NO:47; and a protein comprising an epitope of said protein having an amino acid sequence that is at least about 90 percent identical to an amino acid sequence selected from the group consisting of SEQ ID NO:42 and SEQ ID NO:47; a mimetope of any of said CTLA4 proteins; a multimeric form of any of said CTLA4 proteins; an isolated nucleic acid molecule selected from the group consisting of: a nucleic acid molecule having a nucleic acid sequence that is at least about 80 percent identical to a nucleic acid sequence selected from the group consisting of SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:25, SEQ ID NO:27, SEQ ID NO:28, SEQ ID NO:29, SEQ ID NO:30, SEQ ID NO:32, SEQ ID NO:33, and SEQ ID NO:35; a nucleic acid molecule consisting of a nucleic acid sequence selected from the group consisting of SEQ ID NO:36, SEQ ID NO:38, SEQ ID NO:39, and SEQ ID NO:40; and a nucleic acid molecule having a nucleic acid sequence that is at least about 90 percent identical to a nucleic acid sequence selected from the group consisting of SEQ ID NO:41, SEQ ID NO:43, SEQ ID NO:44, SEQ ID NO:45, SEQ ID NO:46, SEQ ID NO:48, SEQ ID NO:49, and SEQ ID NO:50; an isolated antibody that selectively binds to any of said B7 proteins; an inhibitor of B7 protein activity identified by its ability to inhibit the activity of any of said B7 proteins; an isolated antibody that selectively binds to any of said CTLA4 proteins; and an inhibitor of CTLA4 protein activity identified by its ability to inhibit the activity of any of said CTLA4 proteins, and a mixture thereof. The present invention also includes methods to administer such therapeutic compositions.

Yet another aspect of the present invention is a method to identify a compound capable of regulating T cell mediated immune responses in an animal, said method comprising: (a) contacting an isolated B7 or CTLA4 protein comprising an amino acid sequence selected from the group consisting of SEQ ID NO:2, SEQ ID NO:7, SEQ ID NO:12, SEQ ID NO:17, SEQ ID NO:26, SEQ ID NO:31, SEQ ID NO:34, SEQ ID NO:42, and SEQ ID NO:47 with a putative inhibitory compound under conditions in which, in the absence of the compound, the protein has T cell stimulating activity; and (b) determining if the putative inhibitory compound inhibits said activity.

DETAILED DESCRIPTION OF THE INVENTION

The present invention provides for isolated B7 and CTLA4 proteins, isolated B7 and CTLA4 nucleic acid molecules, antibodies directed against B7 and CTLA4 proteins, and compounds derived therefrom that regulate the immune response of an animal (e.g. inhibitors, antibodies and peptides). Identification of canine B7 nucleic acid molecules of the present invention is unexpected because initial attempts to obtain nucleic acid molecules using PCR were unsuccessful. After numerous attempts, the inventors discovered specific primers that were useful for isolating such nucleic acid molecules. In addition, the inventors discovered novel naturally-occuring nucleic acid molecules that encode variable forms of B7-1 and B7-2 proteins.

A B7 protein can refer to a B7-1 protein, a B7-2 protein, including variants thereof. As used herein, the phrase "regulate an immune response" refers to modulating the activity of cells involved in an immune response. The term "regulate" can refer to increasing or deceasing an immune response Regulation of an immune response can be determined using methods known in the art as well as methods disclosed herein. As used herein, the terms isolated B7 proteins, isolated CTLA4 proteins, isolated B7 nucleic acid molecules and isolated CTIA4 nucleic acid molecules refers to B7 and CTLA4 proteins and B7 and CTLA4 nucleic acid molecules derived from mammals and, as such, can be obtained from their natural source, or can be produced using, for example, recombinant nucleic acid technology or chemical synthesis. Also included in the present invention is the use of these proteins, nucleic acid molecules, antibodies and compounds derived therefrom as therapeutic compositions to regulate the immune response of an animal as well as in other applications, such as those disclosed below.

One embodiment of the present invention is an isolated protein that includes a B7 protein or a CTLA4 protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. According to tire present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, an isolated B7 or CTILA4 protein of the present invention (i.e., a B7 or CTLA4 protein) can be a full-length protein or any homolog of such a protein. An isolated protein of the present invention, including a homolog, can be identified in a straight-forward manner by the protein's ability to elicit an immune response against a B7 or CTLA4 protein, bind to CD28 or CTLA4 (for a B7 protein), or bind to B7 (for a CTLA4 protein), or stimulate T cell activity. Examples of B7 and CTLA4 homologs include B7 and CTLA4 proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against a B7 or CTLA4 protein, of binding to an antibody directed against a B7 or CTLA4 protein, of binding to CD28 or CTLA4 (for a B7 protein), of binding to B7 (for a CTLA4 protein) and/or of stimulating T cell activity. That is, when the homolog is administered to an animal as an immunogen, using techniques known to those skilled in the art, the animal will produce an immune response against at least one epitope of a natural B7 or CULA4 protein. The ability of a protein to effect an immune response can be measured using techniques known to those skilled in the art. As used herein, the term "epitope" refers to the smallest portion of a protein capable of selectively binding to the antigen binding Site of an antibody, or to B7, CD28 or CTLA4. It is well accepted by those skilled in the art that the minimal size of a protein epitope capable of selectively binding to the antigen binding site of an antibody is about six to seven amino acids.

B7 and CTLA4 protein homologs can be the result of natural allelic variation, including natural mutation. B7 and CTLA4 protein homologs of the present invention can also be produced using techniques known in the art including, but not limited to, direct modifications to the protein or modifications to the gene encoding the protein using, for example, classic or recombinant DNA techniques to effect random or targeted mutagenesis.

B7 and CTLA4 proteins of the present invention include variants of a full-length B7 or CTLA4 protein. Such variants include B7 or CTLA4 proteins that are less than full-length. As used herein variants of the present invention refer to nucleic acid molecules that are naturally-occuring as defmed below, and may result from alternative RNA splicing, alternative termination of an amino acid sequence or DNA recombination. Examples of variants include allelic variants as defined below, or soluble forms of a B7 or CTA4 protein.

B7 and CTLA4 proteins of the present invention are encoded by B7 and CTLA4 nucleic acid molecules. As used herein, a B7 nucleic acid molecule includes nucleic acid sequences related to natural B7 gene, and preferably, to a B7-1 or B7-2 gene. As used herein, a CTLA4 nucleic acid molecule includes nucleic acid sequences related to natural CTLA4 gene. As used herein, a B7 or CTLA4 gene refers to the natural genomic elements that encode a B7 or CTLA4 protein, and includes all regions such as regulatory regions that control production of the B7 or CTLA4 protein encoded by the gene (such as, but not limited to, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that region that is translated into a full-length, i.e., a complete, protein as would be initially translated in its natural millieu, prior to any post-translational modifications.

In one embodiment, a B7 gene of the present invention includes the nucleic acid sequence SEQ D NO:1, as well as the complement of SEQ ID NO. 1. Nucleic acid sequence SEQ ID NO:1 represents the deduced sequence of the coding strand of a cDNA (complementary DNA) denoted herein as nucleic acid molecule nCaB7-$1_{2830}$, the production of which is disclosed in the Examples. Nucleic acid molecule nCaB7-$1_{2830}$ comprises an apparently full-length coding region of canine B7-1. The complement of SEQ ID NO:1 (represented herein by SEQ ID NO:3) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is fully complementary to (i.e., can form a double helix with) the strand for which the sequence is cited It should be noted that since nucleic acid sequencing technology is not entirely error-free, SEQ ID NO:1 (as well as other nucleic acid and protein sequences presented herein) represents an apparent nucleic acid sequence of the nucleic acid molecule encoding a B7 protein of the present invention.

In another embodiment, a B7 gene of the present invention includes the nucleic acid sequence SEQ ID NO:6, as well as the complement represented by SEQ ID NO:8. Nucleic acid sequence SEQ ID NO:6 represents the deduced sequence of the coding strand of a cDNA denoted herein as nucleic acid molecule nCaB7-$2_{1897}$, the production of which is disclosed in the Examples. Nucleic acid molecule nCaB7-$2_{1987}$, comprises an apparently full-length coding region of canine B7-2.

In another embodiment, a B7 gene of the present invention includes the nucleic acid sequence SEQ ID NO:11, as well as the complement represented by SEQ ID NO:13. Nucleic acid sequence SEQ ID NO:11 represents the deduced sequence of the coding strand of a cDNA denoted herein as nucleic acid molecule nCaB7-$1s_{1024}$, the production of which is disclosed in the Examples. Nucleic acid molecule nCaB7-$1s_{1024}$ comprises an apparently full-length coding region of a naturally-occuring soluble canine B7-1.

In another embodiment, a B7 gene of the present invention includes the nucleic acid sequence SEQ ID NO:16, as well as the complement represented by SEQ ID NO 18. Nucleic acid sequence SEQ ID NO:16 represents the deduced sequence of the coding strand of a cDNA denoted herein as nucleic acid molecule nCaB7-2s$_{1795}$, the production of which is disclosed in the Examples. Nucleic acid molecule nCaB7-2s$_{1795}$ comprises an apparently full-length coding region of a naturally-occuring soluble canine B7-2.

In another embodiment, a B7 gene of the present invention includes the nucleic acid sequence SEQ ID NO:25, as well as the complement represented by SEQ ID NO:27. Nucleic acid sequence SEQ ID NO:25 represents the deduced sequence of the coding strand of a cDNA denoted herein as nucleic acid molecule nFeB7-2$_{1897}$, the production of which is disclosed in the Examples. Nucleic acid molecule nFeB7-2$_{1897}$ comprises an apparently full-length coding region of feline B7-2.

In another embodiment, a B7 gene of the present invention includes the nucleic acid sequence SEQ ID NO:36, as well as the complement represented by SEQ ID NO:38. Nucleic acid sequence SEQ ID NO:36 represents the deduced sequence of the coding strand of a cDNA denoted herein as nucleic acid molecule nFeB7-1s$_{594}$, the production of which is disclosed in the Examples. Nucleic acid molecule nFeB7-1s$_{594}$ comprises an apparently full-length coding region of a naturally-occuring soluble feline B7-1.

In another embodiment, a CTLA4 gene of the present invention includes the nucleic acid sequence SEQ ID NO:41, as well as the complement represented by SEQ ID NO:43. Nucleic acid sequence SEQ ID NO:41 represents the deduced sequence of the coding strand of a cDNA denoted herein as nucleic acid molecule nCaCTLA4$_{1856}$, the production of which is disclosed in the Examples. Nucleic acid molecule nCaCTLA4$_{1856}$ comprises an apparently full-length coding region of a canine CTlA4. In another embodiment, a CTLA4 gene of the present invention includes the nucleic acid sequence SEQ ID NO:46, as well as the complement represented by SEQ ID NO:48. Nucleic acid sequence SEQ ID NO:46 represents the deduced sequence of thee coding strand of a cDNA denoted herein as nucleic acid molecule nFeCTLA4$_{1883}$, the production of which is disclosed in the Examples. Nucleic acid molecule nFeCTLA4$_{1883}$ comprises an apparently full-length coding region of a feline CTLA4.

In another embodiment, a B7 or CTLA4 gene or nucleic acid molecule can be an allelic variant that includes a similar but not identical sequence to SEQ ID NO:1, SEQ ID NO:3, SEQ ID NO:4, SEQ ID NO:5, SEQ ID NO:6, SEQ ID NO:8, SEQ ID NO:9, and SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, SEQ ID NO:38, SEQ ID NO:39, SEQ ID NO:40, SEQ ID NO:41, SEQ ID NO:43, SEQ ID NO:44, SEQ ID NO:45, SEQ ID NO:46, SEQ ID NO:48, SEQ ID NO:49, SEQ ID NO:50 or any other B7 nucleic acid sequence cited herein. An allelic variant of a B7 or CTLA4 gene including the particular SEQ ID NO's cited herein, is a gene that occurs at essentially the same locus (or loci) in the genome as the gene including the particular SEQ ID NO's cited herein, but which, due to natural variations caused by, for example, mutation or recombination, has a similar but not identical sequence. Because natural selection typically selects against alterations that affect function, allelic variants usually encode proteins having similar activity to that of the protein encoded by the gene to which they are being compares Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to be found within a given animal, since the respective genomes are diploid, and sexual reproduction will result in the reassortment of alleles.

The minimal size of a B7 or CTLA4 protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As used herein, "stringent hybridization conditions" refer to those experimental conditions under which nucleic acid molecules having similar nucleic acid sequences will anneal to each other. Stringent hybridization conditions are well known to those of skill in the art Such standard conditions are disclosed, for example, in Sambrook et al., *Molecular Cloning Laboratory Manual,* Cold Spring Harbor Labs Press, 1989. Stringent hybridization conditions typically permit the hybridization of nucleic acid molecules having at least about 70% nucleic acid sequence identity with the nucleic acid molecule being used as a probe in the hybridization reaction. Formulae to calculate the appropriate hybridization and wash conditions to achieve hybridization permitting 30% or less mis-match between two nucleic acid molecules are disclosed, for example, in Meinkoth et al, 1984, *Anal. Biochem* 138, 267–284. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size, of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a B7 protein homolog of the present invention is from about 12 to about 18 nucleotides in length. Thus, the minimal size of a B7 protein homolog of the present invention is from about 4 to about 6 amino acids in length. There is no limit, other than a practical limit, on the maximal size of such a nucleic acid molecule in that the nucleic acid molecule can include a portion of a gene, an entire gene, or multiple genes, or portions thereof The preferred size of a protein encoded by a nucleic acid molecule of the present invention depends on whether a full-length, fusion, multivalent, or functional portion of such a protein is desired.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art See, for example, Sambrook, et al., 1989, *Molecular Cloning. A Laboratory Manual,* Cold Spring Harbor Labs Press, and Meinkoth, et al,. 1984, *Anal. Biochem* 138, 267–284. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° C. + 16.6 \log M + 0.41(\% G+C) - 500/n - 0.61(\% \text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art These simple procedures allow one skilled in the art to set the hybridization conditions (by altering, for example, the salt concentration, the formamide concentration or the temperature) so that only nucleic acid hybrids with greater than a specified % base pair mismatch will hybridize. Stringent hybridization conditions are commonly understood by those skilled in the art to be those experimental conditions that will allow about 30% base pair mismatch (i.e., about 70% identity). Because one skilled in the ant can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under stringent hybridization conditions with a specific or known canine nucleic acid molecule of about 150 bp in length, the following conditions could preferably be used. The average G+C content of canine DNA includes about 35%, about 36%, about 37%, about 38%, about 39%, about 41%, about 42%, about 43%, about 44%, about 45%, with about 40% being preferred The unknown nucleic acid molecules would be attached to a support membrane, and the specified 150 bp nucleic acid molecule would be labeled, e.& with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. In order to achieve high stringency hybridization, the skilled artisan would calculate the washing conditions required to allow up to 30% base-pair mismatch. For example, in a wash solution comprising 1×SSC and 0% formamide, the $T_m$ of perfect hybrids would be about 80.8° C.:

$$81.5° C. + 16.6 \log (0.15M) + (0.41 \times 40) - (500/150) - (0.61 \times 0) = 80.8° C.$$

Thus, to achieve hybridization with nucleic acid molecules having about 30% base-pair mismatch, hybridization washes would be carried out at a temperature of about 50.8° C. It is within the skill of one in the art to calculate the hybridization temperature based on the formulae and GIC content disclosed herein.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, the Wisconsin Package Version 9.0 sequence analysis software, available from Genetics Computer Group (GCG), Madison, Wis.; DNAsis™, available from Hitachi Software; San Bruno, Calif.; and MacVector™, available from the Eastman Kodak Company, New Haven, Conn. A preferred method to determine percent identity among amino acid sequences and also among nucleic acid sequences includes using the GAP program with pair-wise comparisons within the Wisconsin Package Version 9.0 sequence analysis software, available from Genetics Computer Group (GCG), Madison, Wis., hereinafter referred to as default parameters.

The present invention also includes mimetopes of B7 and CTLA4 proteins of the present invention. As used herein, a mimetope of a B7 or CTLA4 protein of the present invention refers to any compound that is able to mimic the activity of such a B7 or CTLA4 protein, often because the mimetope has a structure that mimics the particular B7 or CTLA4 protein. Mimetopes can be, but are not limited to: peptides that have been modified to decrease their susceptibility to degradation such as all-D retro peptides; anti-idiotypic and/ or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of a B7 or CTLA4 protein of the present invention is a fusion protein that includes a B7 or CTLA4 protein-containing domain attached to one or more fusion segments. Suitable fusion segments for use with the present invention include, but are not limited to, segments that can: link two or more B7 or CTLA4 proteins to form multimeric forms of B7 or CTLA4 protein; enhance a protein's stability, act as an immunopotentiator to enhance an immune response against a B7 or CTIA4 protein; and/or assist in purification of a B7 or CTLA4 protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the B7 or CTL4-containing domain of the protein and can be susceptible to cleavage in order to enable straight-forward recovery of a B7 or CTLA4 protein. Fusion proteins are preferably produced by culturing a recombinant cell transformed with a fusion nucleic acid molecule that encodes a protein including the fusion segment attached to either the carboxyl and/or amino terminal end of a B7 or CTLA4containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

A suitable fusion segment that links one B7 or CTLA4 protein to another B7 or CTLA4 protein includes any amino acid sequence that enables B7 or CTLA4 proteins to be linked while maintaining the biological function of the B7 or CTLA4 proteins. Selection of a suitable linker is dependent upon how many B7 or CTLA4 proteins are to be linked to form one multimeric molecule and from where on the B7 or CTLA4 molecule the linker extends. Preferably, a linker fusion segment of the present invention comprises a peptide of from about 6 amino acid residues to about 40 residues, more preferably from about 6 residues to about 30 residues in length.

In another embodiment, a B7 or CTIA4 protein of the present invention also includes at least one additional protein segment that is capable of targeting a B7 or CTLA4 protein to a desired cell or receptive molecule. Such a multivalent protective protein can be produced by culturing a cell transformed with a nucleic acid molecule comprising two or more nucleic acid domains joined together in such a manner that the resulting nucleic acid molecule is expressed as a multivalent targeting protein containing a B7 or CTLA4 protein or portion thereof and at least one targeting compound capable of delivering the B7 or CTLA4 protein to a desired site in an animal.

Examples of multivalent targeting proteins include, but are not limited to, a B7 or CTLA4 protein of the present invention attached to one or more compounds that can bind to a receptive molecule on the surface of a cell located in an area of an animal where regulation of an immune response is desired. One of skill in the art can select appropriate targeting fusion segments depending upon the cell or receptive molecule being targeted.

A naturally-occuring variant of B7-1 or B7-2 protein of the present invention is preferably isolated from (including isolation of the natural protein or production of the protein by recombinant or synthetic techniques) from mammals, including but not limited to dogs (i.e., canids), cats (i.e., felids), horses (i.e., equids), humans, cattle, chinchillas, ferrets, goats, mice, minks, rabbits, raccoons, rats, sheep, squirrels, swine, chickens, ostriches, quail and turkeys as well as other furry animals, pets, zoo animals, work animals and/or food animals. Particularly preferred animals from which to isolate B7 and CTLA4 proteins are dogs, cats, horses and humans.

A preferred isolated protein of the present invention is a protein encoded by at least one of the following nucleic acid molecules: nCaB7-$1_{2830}$, nCaB7-$1_{1385}$, nCaB7-$1_{912}$, nCaB7-$2_{1897}$, nCaB7-$2_{987}$, nCaB7-$1s_{1024}$, nCaB7-$1s_{705}$, nCaB7-$2s_{1795}$, nCaB7-$2s_{840}$, nFEB7-$2_{1897}$, nFeB7-$2_{996}$, λ-nCaB7-$2_{1897}$, pCMV-nCaB7-$2_{1897}$λ-nCaB7-$1_{2830}$, pCMV-nCaB7-$1_{1385}$, λ-nFeB7-$2_{1897}$, nCaB7-$1_{810}$, nCaB7-$2_{921}$, nCaB7-$1s_{603}$, nCaB7-$2s_{774}$ and/or nFeB7-$2_{918}$, or allelic variants of any of these nucleic acid molecules. Also preferred is an isolated protein that is encoded by a nucleic acid molecule the having nucleic acid sequence SEQ ID NO:1, SEQ ID NO:4, SEQ ID NO:6, SEQ ID NO:9, SEQ ID NO:11, SEQ ID NO:14, SEQ ID NO:16, SEQ ID NO:19, SEQ ID NO:25 and/or SEQ ID NO:28; or an allelic variant of such a nucleic acid molecule.

Translation of SEQ ID NO: 1, the coding strand of nCaB7-$1_{2830}$, yields a protein of about 304 amino acids, denoted herein as PCaB7-$1_{304}$, the amino acid sequence of which is presented in SEQ ID NO:2, assuming an open reading frame having an initiation codon spanning from nucleotide 337 through nucleotide 339 of SEQ ID NO:1 and a stop codon spanning from nucleotide 1249 through nucleotide 1251 of SEQ ID NO:1. The coding region encoding PCaB7-$1_{304}$ is presented herein as nCaB7-$1_{912}$, which has the nucleotide sequence SEQ ID NO:4 (the coding strand) and SEQ ID NO:5 (the complementary strand).

Translation of SEQ ID NO:6, the coding strand of nCaB7-$2_{1897}$, yields a protein of about 329 amino acids, denoted herein as PCaB7-$2_{329}$, the amino acid sequence of which is presented in SEQ ID NO:7, assuming an open reading frame having an initiation codon spanning from nucleotide 6 through nucleotide 8 of SEQ ID NO:6 and a stop codon spanning from nucleotide 993 through nucleotide 995 of SEQ ID NO:6. The coding region encoding PCaB7-$2_{329}$, not including the termination codon, is presented herein as nCaB7-$2_{987}$, which has the nucleotide sequence SEQ ID NO:9 (the coding strand) and SEQ ID NO:10 (the complementary strand).

Translation of SEQ ID NO:25, the coding strand of nFeB7-$2_{1897}$, yields a protein of about 332 amino acids, denoted herein as PFeB7-$2_{329}$, the amino acid sequence of which is presented in SEQ ID NO:26, assuming an open reading fame having an initiation codon spanning from nucleotide 6 through nucleotide 8 of SEQ ID NO:25 and a stop codon spanning from nucleotide 993 through nucleotide 995 of SEQ ID NO:25. The coding region encoding PFeB7-$2_{329}$ is presented herein as nFeB7-$2_{996}$, which has the nucleotide sequence SEQ ID NO:28 (the coding strand) and SEQ ID NO:29 (the complementary strand).

One embodiment of a B7 or CTLA4 protein of the present invention includes a naturally-occuring variant of B7 or CTLA4 protein. As used herein, a naturally-occuring variant refers to a B7 or CTLA4 protein that is originally encoded by a nucleic acid molecule that, in its native form, i.e., a native sequence encoded by a gene, and not mutated by human manipulation such as by recombinant or synthetic techniques that, for example, mutate, modify or create a variant B7 nucleic acid sequence, encodes a B7 variant. According to the present invention, copies of nucleic acid molecules encoding naturally-occurring variants can be produced recombinantly. Without being bound by theory, a variant may arise due to DNA recombination, alternative RNA splicing, or a mutation resulting in premature termination of translation. Examples include soluble B7 or CTLA4 proteins lacking at least a portion of transmembrane domain, or all or a portion of the transmembrane and intracellular domains, sufficient to produce a soluble protein upon translation of a nucleic acid molecule encoding the protein, either in vitro or in a suitable host cell. Such a protein retains the ability to bind to CD28 and/or CTLA4, and stimulate T cell activity, but is soluble. Preferred B7 variants include B7-1 and B7-2 variants. One example of a naturally-occuring B7-1 variant is a B7-1 protein encoded by a nucleic acid molecule lacking at least a portion of the nucleic acid molecule that encodes the transmembrane and intracellular domains of the B7-1 protein, sufficient to produce a soluble B7-1 protein upon translation of a nucleic acid molecule encoding the protein, either in vivo or in a suitable host cell. Another example of a naturally-occuring B7-2 variant is a B7-2 protein encoded by a nucleic acid molecule lacking at least a portion of the nucleic acid molecule that encodes the transmembrane domain, sufficient to produce a soluble B7-2 protein upon translation of a nucleic acid molecule encoding the protein, either in vivo or in a suitable host cell. A naturally-occuring B7-1 variant of the present invention is preferably encoded by a nucleic acid molecule that hybridizes under stringent hybridization conditions to a nucleic acid molecule including SEQ ID NO:13, and/or SEQ ID NO:15. More preferably, a naturally-occuring B7-1 variant comprises an amino acid molecule including SEQ ID NO:12. More preferably, a naturally-occuring B7-1 variant of the present invention is encoded by a nucleic acid molecule that comprises a nucleic acid molecule including SEQ ID NO:11, and/or SEQ ID NO:14.

An example of a naturally-occuring B7-1 variant is encoded by the nucleic acid molecule nCa7-$1s_{1024}$. Translation of SEQ ID NO:11, the coding strand of nCaB7-$1s_{1024}$, yields a protein of about 235 amino acids, denoted herein as PCaB7-$1s_{235}$, the amino acid sequence of which is presented in SEQ ID NO:12, assuming an open reading frame having an initiation codon spanning from nucleotide 79 though nucleotide 81 of SEQ ID NO:11 and a stop codon spanning from nucleotide 784 through nucleotide 786 of SEQ ID NO:11. The coding region encoding PCaB7-$1s_{235}$, not including the termination codon, is presented herein as nCaB7-$1s_{705}$, which has the nucleotide sequence SEQ ID NO:14 (the coding strand) and SEQ ID NO:15 (the complementary strand).

One example of a naturally-occuring B7-2 variant is a B7-2 protein lacking at least a portion of the transmembrane domain. Such a naturally-occuring B7-2 variant is preferably encoded by a nucleic acid molecule that hybridizes under stringent hybridization conditions to a nucleic acid molecule including SEQ ID NO:18, and/or SEQ ID NO:20. More preferably, a naturally-occuring of B7-2 variant comprises an amino acid molecule including SEQ ID NO:17. More preferably, a naturally-occuring of B7-2 variant is encoded by a nucleic acid molecule that comprises a nucleic acid molecule including SEQ ID NO:16, and/or SEQ ID NO:19.

An example of a naturally-occuring B7-2 variant is encoded by the nucleic acid molecule nCaB7-$2s_{1795}$. Translation of SEQ ID NO:16, the coding strand of nCaB7-$2s_{1795}$, yields a protein of about 280 amino acids, denoted herein as PCaB7-$2s_{280}$, the amino acid sequence of which is presented in SEQ ID NO:17, assuming an open reading frame having an initiation codon spanning from nucleotide 7 through nucleotide 9 of SEQ ID NO:16 and a stop codon spanning from nucleotide 847 through nucleotide 849 of SEQ ID NO:16. The coding region encoding PCaB7-$2s_{280}$, not including the termination codon, is presented herein as nCaB7-$2s_{280}$, which has the nucleotide sequence SEQ ID NO:19 (the coding strand) and SEQ ID NO:20 (the complementary strand). SEQ ID NO:16 is predicted to encode a B7-2 protein lacking at least a portion of the transmembrane domain.

Preferred B7 proteins of the present invention include proteins that are at least about 80%, preferably at least about 85%, even more preferably at least about 90%, and even more preferably at least about 95% identical to PCaB7-$1_{304}$, or epitopes thereof; are at least about 60%, preferably at least about 65%, more preferably at least about 70%, more preferably at least about 75%, more preferably at least about 80%, more preferably at least about 85%, more preferably at least about 90%, and even more preferably at least about 95%, identical to PCaB7-$2_{329}$, or epitopes thereof; are at least about 80%, preferably at least about 85%, even more preferably at least about 90%, and even more preferably at least about 95% identical to PCaB7-$1s_{235}$, or epitopes thereof; are at least about 60%, preferably at least about 65%, more preferably at least about 70%, more preferably at least about 75%, more preferably at least about 80%, more preferably at least about 85%, more preferably at least about 90%, and even more preferably at least about 95%, identical to PCaB7-$2s_{280}$, or epitopes thereof; or are at least about 60%, preferably at least about 65%, more preferably at least about 70%, more preferably at least about 75%, more preferably at least about 80%, more preferably at least about 85%, more preferably at least about 90%, and even more preferably at least about 95%, identical to PFeB7-$2_{332}$, or epitopes thereof.

More preferred are B7 proteins comprising PCaB7-$1_{304}$, PCaB7-$2_{329}$, PCaB7-$1s_{235}$, PCaB7-$2s_{280}$, PFeB7-$2_{332}$, PCaB7-$1_{270}$, PCaB7-$2_{307}$, PCaB7-$1s_{201}$, PCaB7-$2s_{258}$ or PFeB7-$2_{309}$, and proteins encoded by alielic variants of nucleic acid molecules encoding proteins PCaB7-$1_{304}$, PCaB7-$2_{329}$, PCaB7-$1s_{235}$, PCaB7-$2s_{280}$, PFeB7-$2_{332}$, PCaB7-$1_{270}$, PCaB7-$2_{307}$, PCaB7-1s201, PCaB7-$2s_{258}$ or PFeB7-309.

Also preferred are B7 proteins of the present invention having amino acid sequences that are at least about 80%, preferably at least about 85%, even more preferably at least about 90%, and even more preferably at least about 95% identical to SEQ ID NO:2, or epitopes thereof, are at least about 60%, preferably at least about 65%, more preferably at least about 70%, more preferably at least about 75%, more preferably at least about 80%, more preferably at least about 85%, more preferably at least about 90%, and even more preferably at least about 95%, identical to SEQ ID NO:7, or epitopes thereof; are at least about 80%, preferably at least about 85%, even more preferably at least about 90%, and even more preferably at least about 95% identical to, identical to SEQ ID NO:12, or epitopes thereof; are at least about 60%, preferably at least about 65%, more preferably at least about 70%, more preferably at least about 75%, more preferably at least about 80%, more preferably at least about 85%, more preferably at least about 90%, and even more preferably at least about 95%, identical to SEQ ID NO:17, or epitopes thereof; or are at least about 60%, preferably at least about 65%, more preferably at least about 70%, more preferably at least about 75%, more preferably at least about 80%, more preferably at least about 85%, more preferably at least about 90%, and even more preferably at least about 95%, identical to SEQ ID NO:26, or epitopes thereof. More preferred are B7 proteins comprising amino acid sequences SEQ ID NO:2, SEQ ID NO:7, SEQ ID NO:12, SEQ ID NO:17 and/or SEQ ID NO:26; and B7 proteins encoded by allelic variants of nucleic acid molecules encoding B7 proteins having amino acid sequences SEQ ID NO:2, SEQ ID NO:7, SEQ ID NO:12, SEQ ID NO:17 and/or SEQ ID NO:26.

Preferred CTLA4 proteins of the present invention include proteins that are at least about 90%, preferably at least about 95% identical to PCaCTJLA4$_{224}$, or epitopes thereof; or are at least about 90%, preferably at least about 95% identical to PFeCTLA4$_{223}$, or epitopes thereof More preferred are CTLA4 proteins comprising PCaCTLA4$_{223}$, or PFeCTLA4$_{223}$, and proteins encoded by allelic variants of nucleic acid molecules encoding proteins PCaCTLA4$_{223}$, or PFeCTLA4$_{223}$.

Also preferred are CTLA4 proteins of the present invention having amino acid sequences that are at least about 90%, preferably at least about 95% identical to SEQ ID NO:41, or epitopes thereof; or are at least about 90%, a, preferably at least about 95% identical to SEQ ID NO:46, or epitopes thereof More preferred are CTLA4 proteins comprising amino acid sequences SEQ ID NO:41, and/or SEQ ID NO46; and CTLA4 proteins encoded by allelic variants of nucleic acid molecules encoding CTLA4 proteins having amino acid sequences SEQ ID NO:41, and/or SEQ ID NO:46.

Percent identities between amino acid or nucleic acid sequences can be determined using standard methods known to those of skill in the art. It is known in the art that methods to determine the percentage identity and the number of gaps are: substantially similar when different methods for determining sequence similarity are used and when the degree of similarity is greater than 30% amino acid identity, as described by Johnson et al., *J. Mol. Biol.,* vol. 233, pages 716–738, 1993, and Feng et al., *J. Mol. Evol.,* vol. 21, pages 112–125, 1985. Preferred methods to determine percentage identities between amino acid sequences and between nucleic acid sequences include comparison using various computer programs such as the Wisconsin Package Version 9.0 sequence analysis software, available from Genetics Computer Group (GCG), Madison, Wis.; DNAsis™ program, available from Hitachi Software, San Bruno, Calif.; or the MacVector™ program, available from the Eastman Kodak Company, New Haven, Conn. A preferred method to determine percentage identities between amino acid sequences and between nucleic acid sequences includes using the DNAsis™ computer program with the following settings: the gap penalty set at 5; the number of top diagonals set at 5; the fixed gap penalty set at 10; the k-tuple set at 2; the window size set at 5 and the floating gap penalty set at 10.

Additional preferred B7 or CTLA4 proteins of the present invention include proteins encoded by nucleic acid molecules comprising at least a portion of nCaB7-1$_{2830}$, nCaB7-1$_{1385}$, nCaB7-1$_{912}$, nCaB7-2$_{1897}$, nCaB7-2$_{987}$, nCaB7-1s$_{1024}$, nCaB7-1s$_{705}$, nCaB7-2s$_{1795}$, nCaB7-2s$_{840}$, nFeB7-2$_{2830}$, nFeB7-2$_{996}$, nCaB7-1$_{810}$, nCaB7-2$_{921}$, nCaB7-1s$_{603}$, nCaB7-2s$_{774}$, nFeB7-2$_{918}$, nFeB7-2$_{509}$, nFeB7-2s$_{359}$, nFeB7-1s$_{594}$ nFeB7-1s$_{519}$, nCaCTLA4$_{1856}$, nCaCTLA4$_{672}$, nFeCTLA4$_{1883}$, and/or nFeCTLA4672, as well as B7 or CTLA4 proteins encoded by allelic variants of such nucleic acid molecules.

Also preferred are B7 proteins encoded by nucleic acid molecules having nucleic acid sequences comprising at least a portion of SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, SEQ ID NO:38, SEQ ID NO:39, SEQ ID NO:40 SEQ ID NO:41SEQ ID NO:43, SEQ ID NO:44, SEQ ID NO:45, SEQ ID NO:46, SEQ ID NO:48, SEQ ID NO:49, and/or SEQ ID NO:50, as well as allelic variants of these nucleic acid molecules.

Another embodiment of the present invention is a B7 or CTLA4 nucleic acid molecule that includes one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a B7 or CTLA4 nucleic acid molecule of the present invention is from about 12 to about 18 nucleotides in length.

In accordance with the present invention, an isolated nucleic acid molecule is a nucleic acid molecule Fat has been removed from its natural milieu (i.e., that has been subjected to human manipulation) and can include DNA, RNA, or derivatives of either DNA or RNA. As such, "isolated" does not reflect the extent to which the nucleic acid molecule has been purified. An isolated B7 or CTLA4 nucleic acid molecule of the present invention can be isolated from its natural source or produced using recombinant DNA technology (e.g., polymerase chain reaction (PCR) amplification or cloning) or chemical synthesis. Isolated B7 or CTLA4 nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode a B7 protein of the present invention.

A B7 or CTLA4 nucleic acid molecule homolog can be produced using a number of methods known to those skilled in the art, see for example, Sambrook et al., 1989, *Molecular Cloning: A Laboratory Manual,* Cold Spring Harbor Labs Press. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologs can be selected by hybridization with a B7 or CTLA4 nucleic acid molecule or by screening the function of a protein encoded by the nucleic acid molecule (e.g., ability to elicit an immune response against at least one epitope of a B7 protein).

An isolated nucleic acid molecule of the present invention can include a nucleic acid sequence that encodes at least one B7 protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a B7 protein.

A preferred nucleic acid molecule of the present invention, when administered to an animal, is capable of regulating an immune response in an animal. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode an immunoregulatory protein (e.g., a cell-bound or soluble B7 protein of the present invention), the nucleic acid molecule being delivered to the animal, for example, by direct injection (i.e, as a genetic vaccine) or in a vehicle such as a recombinant virus vaccine or a recombinant cell vaccine.

One embodiment of the present invention is a B7 or CTLA4 nucleic acid molecule comprising all or part (i.e., a fragment of the B7 or CTLA4 nucleic acid molecule) of nucleic acid molecules nCaB7-1$_{2830}$, nCaB7-1$_{1385}$, nCaB7-1$_{912}$, nCaB7-2$_{1897}$, nCaB7-2$_{987}$, nCaB7-1s$_{1024}$, nCaB7-1s$_{705}$, nCaB7-2s$_{1795}$, nCaB7-2s$_{840}$, nFeB7-2$_{2830}$, nFeB7-2$_{996}$, nCaB7-1$_{810}$, nCaB7-2$_{921}$, nCaB7-1s$_{603}$, nCaB7-2s$_{774}$, nCaB7-2$_{918}$, nFeB7-2$_{509}$, nFeB7-2s$_{359}$, nFeB7-1s$_{594}$, nFeB7-1s$_{519}$, nCaCTLA4$_{1856}$, nCaCTLA4$_{672}$, nFeCTLA4$_{1883}$, and/or nFeCTLA$_{4672}$, or allelic variants of these nucleic acid molecules. Another preferred nucleic acid molecule of the present invention includes at least a portion of (i.e., a fragment of the nucleic acid molecule) nucleic acid sequence SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:25, SEQ ID NO:27, SEQ ID NO:28, SEQ ID NO:29,SEQ ID NO:30, SEQ ID NO:32, SEQ ID NO:33, SEQ ID NO:35, SEQ ID NO:36, SEQ ID NO:38, SEQ ID NO:39, SEQ ID NO:40, SEQ ID NO:41, SEQ ID NO:43, SEQ ID NO:44, SEQ ID NO:45, SEQ ID NO:46, SEQ ID NO:48, SEQ ID NO:49, and/or SEQ ID NO:50, as well as allelic variants of nucleic acid molecules having these nucleic acid sequences. Such nucleic acid molecules can include nucleotides in addition to those included in the SEQ ID NOs, such as, but not limited to, a fill-length gene, a full-length coding region, a nucleic acid molecule encoding a fusion protein, or a nucleic acid molecule encoding a multivalent therapeutic compound.

In one embodiment, a B7 nucleic acid molecule of the present invention encodes a protein that is at least about 80%, preferably at least about 85%, even more preferably at least about 90%, and even more preferably at least about 95% identical to PcaB7-1$_{304}$ or PCaB7-1s$_{235}$; or are at least about 60%, preferably at least about 65%, more preferably at least about 70%, more preferably at least about 75%, more preferably at least about 80%, more preferably at least about 85%, more preferably at least about 90%, and even more preferably at least about 95%, identical to PCaB7-2$_{329}$, PCaB7-2s280, or PFeB7-2$_{332}$. Even more preferred is nucleic acid molecule encoding PCa7-1$_{304}$, PCaB7-2$_{329}$, PCaB7-1s$_{235}$, PCaB7-2s280, PFeB7-2$_{332}$, PFeB7-2$_{169}$, PFeB7-2$_{119}$, PCaB7-1$_{270}$, PCaB7-2$_{307}$, PCAB7-1s$_{201}$, PCaB7-2s$_{258}$, or PFeB7-2$_{309}$, and/or an allelic variant of such a nucleic acid molecule.

In another embodiment, a B7 nucleic acid molecule of the present invention encodes a protein having an amino acid sequence that is at least about 80%, preferably at least about 85%, even more preferably at least about 90%, and even more preferably at least about 95% identical to SEQ ID NO:2 or SEQ ID NO:12; or at least about 60%, preferably at least about 65%, more preferably at least about 70%, more preferably at least about 75%, more preferably at least about 80%, more preferably at least about 85%, more preferably at least about 90%, and even more preferably at least about 95%, identical to SEQ ID NO:7, SEQ ID NO:17 or SEQ ID NO:26. The present invention also includes a B7 nucleic acid molecule encoding a protein having at least a portion of SEQ ID NO:2, SEQ ID NO:7, SEQ ID NO:12, SEQ ID NO:17, SEQ ID NO:26, SEQ ID NO:31, SEQ ID NO:34, SEQ ID NO:37, as well as allelic variants of a B7 nucleic acid molecule encoding a protein having these sequences, including nucleic acid molecules that have been modified to accommodate codon usage properties of the cells in which such nucleic acid molecules are to be expressed.

In one embodiment, a B7 nucleic acid molecule of the present invention is at least about 80%, preferably at least about 85%, more preferably at least about 90%, and more preferably at least about 95% identical to nCaB7-1$_{2830}$, nCaB7-2$_{1897}$, nCaB7-1s$_{1024}$nCaB7-2$_{1897}$, nCaB7-2s$_{1795}$, nCaB7-1s$_{1024}$, or nFeB7-2$_{1897}$. Even more preferred is a nucleic acid molecule comprising nCaB7-1$_{2830}$, nCCaB7-1$_{912}$, nCaB7-2$_{1897}$, nCaB7-2$_{1897}$, nCaB7-2s$_{1795}$, nCaB7 -1s$_{1024}$, nCaB7-1s$_{705}$, nCaB7-2s$_{1795}$, nCaB7-2s$_{840}$, nFeB7-2$_{1897}$, nFeB7-2$_{996}$, nCaB7-1$_{810}$, nCaB7-2$_{921}$, nCaB7-1s$_{603}$, nCaB7-2s774, nFeB7-2$_{918}$, and/or an allelic variant of such a nucleic acid molecule.

In another embodiment, a B7 nucleic acid molecule of the present invention comprises a nucleic acid sequence that is at least about 80%, preferably at least about 85%, more preferably at least about 90%, and more preferably at least about 95% identical to SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, SEQ ID NO:38, SEQ ID NO:39, or SEQ ID NO:40. The present invention also includes a B7 nucleic acid molecule comprising at least a portion of SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:15, SEQ ID NO:16, SEQ ID NO:18, SEQ ID NO:19, SEQ ID NO:25, SEQ ID NO:27, SEQ ID NO:28, SEQ ID NO:29, SEQ ID NO:30, SEQ ID NO:32, SEQ ID NO:33, SEQ ID NO:35, SEQ ID NO:36, SEQ ID NO:38, SEQ ID NO:39, and/or SEQ ID NO:40 as well as allelic variants of such B7 nucleic acid molecules, including nucleic acid molecules that have been modified to accommodate codon usage properties of the cells in which such nucleic acid molecules are to be expressed.

In one embodiment, a CTLA4 nucleic acid molecule of the present invention encodes a protein that is at least about 90%, and preferably at least about 95% identical to PCaCTLA4$_{223}$ or PFeCTLA4$_{223}$. Even more preferred is nucleic acid molecule encoding PCaCTLA4$_{223}$ or PFeCTLA4$_{223}$, and/or an allelic variant of such a nucleic acid molecule.

In another embodiment, a CTLA4 nucleic acid molecule of the present invention encodes a protein having an amino acid sequence that is at least about 90%, and preferably at least about 95% identical to SEQ ID NO:42 or SEQ ID NO:47. The present invention also includes a CTLA4 nucleic acid molecule encoding a protein having at least a portion of SEQ ID NO:42, SEQ ID NO:46, as well as allelic variants of a CTLA nucleic acid molecule encoding a protein having these sequences, including nucleic acid molecules that have been modified to accommodate codon usage properties of the cells in which such nucleic acid molecules are to be expressed.

In one embodiment, a CTLA4 nucleic acid molecule of the present invention is at least about 90%, and preferably at least about 95% identical to nCaCTLA4$_{1856}$ or nFeCTLA4$_{1856}$. Even more preferred is a nucleic acid molecule comprising nCaCTLA4$_{1856}$, nCaCTLA4$_{1883}$, and/or an allelic variant of such a nucleic acid molecule.

In another embodiment, a CTLA4 nucleic acid molecule of the present invention comprises a nucleic acid sequence that is at least about 90%, and preferably at least about 95% identical to SEQ ID NO:41, SEQ ID NO:43, SEQ ID NO:44, SEQ ID NO:45, SEQ ID NO:46, SEQ ID NO:48, SEQ ID NO:49, or SEQ ID NO:50. The present invention also includes a CTLA4 nucleic acid molecule comprising at least a portion of SEQ ID NO:41, SEQ ID NO:43, SEQ ID NO:44, SEQ ID NO:45, SEQ ID NO:46, SEQ ID NO:48, SEQ ID NO:49, and/or SEQ ID NO:50, as well as allelic variants of such CTLA4 nucleic acid molecules, including nucleic acid molecules that have been modified to accommodate codon usage properties of the cells in which such nucleic acid molecules are to be expressed.

Knowing the nucleic acid sequences of certain B7 and CTLA4 nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other B7 or CTLA4 nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include mammalian cDNA libraries as well as genomic DNA libraries. Similarly, preferred DNA sources from which to amplify nucleic acid molecules include mammalian cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising B7 or CTLA4 nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably about 200 nucleotides, more preferably about 150 nucleotides, more preferably about 100 nucleotides and even more preferably about 50 nucleotides. The present invention includes oligonucleotides that can be used as, for example, probes to identify nucleic acid molecules, primers to produce nucleic acid molecules, or therapeutic reagents to inhibit B7 or CTLA4 protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid Recombinant vectors can be used in the cloning, sequencing, and/or otherwise manipulating of B7 or CTLA4 nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically virus or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein, more preferably in vivo.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which unction in bacterial, yeast, helminth or other endoparasite, or insect and mammalian cells, such as, but not limited to, tac, lac, trp, trc, oxy-pro, omp/lpp, mB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with mammals, such as dog, cat, horse, or human transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nCaB7-1_{2830}$, $nCaB7-1_{1358}$, $nCaB7-1_{912}$, $nCaB7-2_{1897}$, $nCaB7-2_{987}$, $nCaB7-1s_{1024}$, $NCaB7-1s_{705}$, $nCaB7-2s_{1795}$, $nCaB7-2s_{840}$, $nFeB7-2_{2830}$, $nFeB7-2_{996}$, $nCaB7-1_{810}$, $nCaB7-2_{921}$, $nCaB7-1s_{603}$, $nCaB7-2s_{774}$, $nFeB7-2_{918}$, $nFeB7-2_{509}$, $nFeB7-2s_{359}$, $nFeB7-1s_{594,}$ $nFeB7-1s_{519}$, $nCaCTLA4_{1856}$, $nCaCTLA4_{672}$, $nFeCTLA4_{1883}$, and $neCTLA4_{4672}$.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment Eukaryotic recombinant molecules may also include intervening and/or untranslated sequences surrounding and/or within the nucleic acid sequences of nucleic acid molecules of the present invention. Preferred recombinant molecules of the present invention include λ-nCaB7-$2_{1897}$pCMV-nCaB7-$2_{1897}$, λ-nCaB7-$1_{2830}$, pCMV-nCaB7-$1_{1385}$ sor λ-nFeB7-1897.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include B7 or CTLA4 nucleic acid molecules disclosed herein. Particularly preferred nucleic acid molecules with which to transform a cell include $nCaB7-1_{2830}$, $nCaB^7-1_{1385}$, $nCaB7-1_{912}$, $nCaB7-2_{1897}$, $nCaB7-2_{987}$, $nCaB7-1s_{1024}$, $nCaB7-1s_{705}$, $nCaB7-2s_{1795}$, $nCaB7-2s_{840}$, $nFeB7-2_{2830}$, $nFeB7-2_{996}$, $nCaB7-1_{810}$, $nCaB7-2_{921}$, $nCaB7-1s_{603}$, $nCaB7-2s_{774}$, $nFeB7-2_{918}$, $nFeB7-2_{509}$, $nFeB7-2s_{359}$, $nFeB7-1_{594}$, $nFeb7-1s_{519}$, $nCaCTLA4_{1856}$, $nCaCTLA4_{672}$ $nFeCTLA4_{1883}$, and $nFeCTLA_{4672}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing B7 or CTLA4 proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, chinese hamster ovary (CHO) cells, Ltk cells and Vero cells. Particularly preferred host cells are *Escherichia coli*, including *E. coli* K-12 derivatives; *Salmonella ophi*; *Salmonella typhimurium*, including attenuated strains such as UK-1 $_03987$ and SR-11 $_04072$; *Spodopterafrugiperda; Trichoplusia ni;* BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH3T3 cells, LMTK[31] cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including B7 or CTLA4 nucleic acid molecules encoding one or more proteins of the present invention and one or more other nucleic acid molecules encoding other protective compounds, as disclosed herein (e.g, to produce multivalent vaccines).

Preferred recombinant cells of the present invention include CHO-pCMV-nCaB7-$2_{1897}$ or CHO-pCMV-nCaB7-$1_{1385}$.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but arc not limited to, operatively linking nucleic acid molecules to highcopy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correpond to the codon usage of the host cell, deletion of sequences that destabilize transcripts, and use of control signals that temporally separate recombinant cell growth from recombinant enzyme production during fermentation The activity of an expressed recombinant protein of the present invention may be improved by fragmenting, modifying, or derivatizing nucleic acid molecules encoding such a protein.

Isolated B7 or CTLA4 proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a B7 or CTLA4 protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art Depending on the vector and host system used for production, resultant proteins of the present invention may either remain within the recombinant cell; be secreted into the fermentation medium; be secreted into a space between two cellular membranes, such as the periplasmic space in *E. coli;* or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a B7 or CTLA4 protein of the present invention or a mimetope thereof (e.g., anti-B7 or CTLA4 antibodies). As used herein, the term "selectively binds to" a B7 or CTLA4 protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual,* Cold Spring Harbor Labs Press. An anti-B7 or CTLA4 antibody of the present invention preferably selectively binds to a B7 or CTLA4 protein in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce B7 or CTLA4 proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as reagents in assays to detect B7 or CTLA4 protein, (b) as reagents in assays to modulate cellular activity through a B7 or CTLA4 protein (e.g., mimicking ligand binding to B7 or CTLA4 protein), and/or (c) as tools to screen expression libraries and/or to recover desired proteins of the present invention from a mixture of proteins and other contaminants. Furthermore, antibodies of the present invention can be used to target compounds (e.g., nucleic acid molecules, drugs or proteins) to antigen presenting cells. Targeting can be accomplished by conjugating (i.e., stably joining) such antibodies to the compounds using techniques known to those skilled in the art. Suitable compounds are known to those skilled in the art.

One embodiment of the present invention is a therapeutic composition that, when administered to an animal in an effective manner, is capable of regulating an immune response in an animal. Therapeutic compositions of the present invention include at least one of the following therapeutic compounds: an isolated B7 or CTLA4 protein of the present invention or a mimetope thereof, an isolated B7 or CTLA4 nucleic acid molecule of the present invention, an isolated antibody that selectively binds to a B7 or CTLA4 protein of the present invention, an inhibitor of B7 or CTLA4 function identified by its ability to bind to a B7 or CTLA4 protein of the present invention and inhibit binding of a B7 protein to CD28 and/or CTLA4, or inhibit binding of a CTLA4 protein to B7, and a mixture thereof (i.e., combination of at least two of the compounds). As used herein, a therapeutic compound refers to a compound that, when administered to an animal in an effective manner, is able to treat, ameliorate, and/or prevent a disease. Examples of proteins, nucleic acid molecules, antibodies and inhibitors of the present invention are disclosed herein.

The present invention also includes a therapeutic composition comprising at least one B7 or CTLA4-based compound of the present invention in combination with at least one additional protective compound. Examples of such compounds are disclosed Lilt herein.

Therapeutic compositions of the present invention can be administered to any animal susceptible to such therapy, preferably to mammals, and more preferably to dogs, cats, humans, ferrets, horses, cattle, sheep and other pets, economic food animals and/or zoo animals. Preferred animals include dogs, cats, horses and humans.

A therapeutic composition of the present invention is administered to an animal in an effective manner such that the composition is capable of regulating an immune response in that animal. Therapeutic compositions of the present invention can be administered to animals prior to onset of a disease (i.e., as a preventative vaccine) and/or can be administered to animals after onset of a disease in order to treat the disease (i.e., as a therapeutic vaccine). Preferred diseases to prevent or treat include autoimmune diseases, allergic reactions, infectious diseases, tumor development and graft rejection.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., Flt-3 ligand, granulocyte macrophage colony stimulating factor (GM-CSF), granulocyte colony stimulating factor (G-CSF), macrophage colony stimulating factor (MOSF), colony stimulating factor (CSF), erythropoietin (EPO), interleukin 2 (IL-2), interleukin-3 (IL3), interleukin 4 (IL4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation normal T-cell expressed and presumably secreted), macrophage inflammatory proteins (e.g., MIP-1 alpha and MIP-1 beta), and Leishmania elongation initiating factor (LEIF)); bacterial components (e.g, endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to regulate an immune response in an animal. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to and/or after onset of disease. Acceptable protocols to administer therapeutic compositions in an effective manner include individual dose size, number of doses, frequency of dose administration, and mode of administration. Determination of such protocols can be accomplished by those skilled in the art A suitable single dose is a dose that is capable of regulating the immune response in an animal when administered one or more times over a suitable time period. For example, a preferred single dose of a protein, mimetope or antibody therapeutic composition is from about 1 microgram (g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is woe in which from about 10 g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, intraoccular, oral, transdermal and intramuscular routes.

According to one embodiment, a nucleic acid molecule of the present invention can be administered to an animal in a fashion to enable expression of that nucleic acid molecule into a therapeutic protein or therapeutic RNA (e.g, antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent A genetic vaccine of the present invention can comprise one or more nucleic acid molecules of the present invention in the form of, for example, a dicistronic recombinant molecule. Preferred genetic vaccines include at least a portion of a viral genome (i.e., a viral vector). Preferred viral vectors include those based on alphaviruses, poxviruses, adenoviruses, herpesvirus, picornavirus, and retroviruses, with those based on alphaviruses (such as sindbis or Semliki forest virus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal intranasal and oral routes of administration being preferred. A preferred single dose of a genetic vaccine ranges from about 1 nanogram (ng) to about 600 g, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picomaviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in PCT Publication No. WO 94/17813, by Xiong et al., published Aug. 18, 1994.

When administered to an animal, a recombinant virus vaccine of the present invention infects cells within the immunized animal and directs the production of a therapeutic protein or RNA nucleic acid molecule that is capable of protecting the animal from disease caused by a parasitic helminth as disclosed herein. For example, a recombinant virus vaccine comprising a B7 or CTLA4 nucleic acid molecule of the present invention is administered according to a protocol that results in the regulation of an immune response in an animal. A preferred single dose of a recombinant virus vaccine of the present invention is from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intranasal, intraoccular and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to regulate the immune response in an animal can be tested in a variety of ways including, but not limited to, detection of cellular immunity within the treated animal, determining T cell activity (helper or cytotoxic T cell activity), identify T cell repertoire, detection of IL-2 levels, detection of antibody levels, determine tumor development or challenge of the treated animal with an infectious agent to determine whether the treated animal is resistant to disease. In one embodiment, therapeutic compositions can be tested in animal models such as mice. Such techniques are known to those skilled in the art.

According to the present invention, a therapeutic composition can be used to treat cancer, infectious diseases, inflammation or allergy. One of skill in the art will appreciate the diseases associated with inflammation or allergy, including for example, arthritis, autoimmune diseases and atopic diseases, such as atopic dermatitis. The inventors present below novel therapeutic compositions based on the discovery of novel B7 variants. The inventors have discovered that naturally-occuring forms of B7 protein include both membrane-bound and soluble forms of B7 protein. Without being bound by theory, the inventors believe that antigen presenting cells (APC's) in an animal produce both forms of B7 protein to regulate an immune response, and that the ratio of membrane-bound to soluble B7 protein is important in such regulation. It is known that an immune response can be upregulated by activating immunoregulatory cells, e.g., T helper cells or dendritic cells, or downregulated by inactivating such immunoregulatory cells. The inventors' discovery of different forms of B7 protein suggests that such forms or derivatives thereof can be used to upregulate or downregulate an immune response. Thus, when stimulation of an immune response is desired, a therapeutic composition of the present invention can include a B7 protein that stimulates the upregulation of immunoregulatory cells and/or inhibits the downregulation of immunoregulatory cells. Alternatively, when inhibition of an immune response is desired, a therapeutic composition of the present invention can include a B7 protein that inhibits the upregulation of immunoregulatory cells and/or stimulates the downregulation of immunoregulatory cells. One of skill in the art will understand that different formulations of a therapeutic composition can be used to upregulate or downregulate an immune response as desired in a particular therapy.

One therapeutic composition of the present invention includes a B7 protein, or a nucleic acid molecule that encodes a B7 protein, that stimulates the upregulation of an immune response, i.e., activates immunoregulatory cells, referred to herein as a stimulatory activating B7 protein. A suitable stimulatory activating B7 protein includes a protein that activates T helper cell and/or T cytotoxic cell activity. A preferred stimulatory activating B7 protein comprises a membrane-bound form of a B7-1 and/or B7-2 protein of the present invention and/or a multimeric form of a naturally-occuring soluble form of B7 of the present invention. As used herein, a membrane-bound B7 protein refers to a B7 protein that is associated with a carrier, such as those disclosed herein. Preferably, a membrane-bound B7 protein is associated with the lipid bilayer of a cell in which the B7 protein has been expressed, e.g., a recombinant cell of the present invention. A preferred stimulatory activating B7 protein is encoded by a nucleic acid molecule that hybridizes under stringent hybridization conditions to SEQ ID NO:3, SEQ ID NO:5, SEQ ID NO:8, SEQ ID NO:10, SEQ ID NO:27 and/or SEQ ID NO:29. A more preferred stimulatory activating B7 protein comprises the amino acid sequence SEQ ID NO:2, SEQ ID NO:7, SEQ ID NO:12, SEQ ID NO:17 and/or SEQ ID NO:26. An even more preferred stimulatory activating B7 protein is encoded by a nucleic acid molecule that comprises the nucleic acid sequence SEQ ID NO:1, SEQ ID NO:4, SEQ ID NO:6, SEQ ID NO:9, SEQ ID NO:11, SEQ ID NO:14, SEQ ID NO:16, SEQ ID NO:19, SEQ ID NO:25 and/or SEQ ID NO:28. A stimulatory activating protein can be delivered to an animal in the form of a protein or a nucleic acid molecule encoding the stimulatory activating protein using methods described herein.

Another therapeutic composition of the present invention includes a B7 protein, or a nucleic acid molecule that encodes a B7 protein, that stimulates the downregulation of an immune response, i.e., inactivates immunoregulatory cells. A suitable stimulatory inactivating B7 protein includes a protein that inactivates T helper cell activity, in particular mature dendritic cell activity. A preferred stimulatory inactivating B7 protein comprises a soluble form of a B7-1 and/or B7-2 protein of the present invention. A preferred stimulatory inactivating B7 protein is encoded by a nucleic acid molecule that hybridizes under stringent conditions to SEQ ID NO:13; SEQ ID NO:15, SEQ ID NO:18 SEQ ID NO:20, SEQ ID NO:33, and/or SEQ ID NO:36, or a nucleic acid molecule encoding a soluble form of a protein ended by the complement of nucleic acid sequence SEQ ID NO:25 and/or SEQ ID NO:28. A more preferred stimulatory activating B7 protein comprises the amino acid sequence SEQ ID NO:12, SEQ ID NO:17, and/or SEQ ID NO:37, or a soluble form of the amino acid sequence SEQ ID NO:26. An even more preferred stimulatory inactivating B7 protein is encoded by a nucleic acid molecule that comprises the nucleic acid sequence SEQ ID NO:11, SEQ ID NO:13, SEQ ID NO:14, SEQ ID NO:15, SEQ ID NO:16, SEQ ID NO:18, SEQ ID NO:19, SEQ ID NO:20, SEQ ID NO:33, SEQ ID NO:35, SEQ ID NO:36, SEQ ID NO38, SEQ ID NO:39 and/or SEQ ID NO:40, or a nucleic acid molecule encoding a soluble form of a protein encoded by a nucleic acid sequence SEQ ID NO;25, SEQ ID NO:27, SEQ ID NO:28 and/or SEQ ID NO:29.

Another therapeutic composition of the present invention includes a blocking therapeutic compound that inhibits the upregulation of downregulation of an immune response, i.e., blocks activation or inactivation of immunoregulatory cells. A blocking compound is capable of substantially interfering with the function of a B7 protein susceptible to inhibition. For example, a blocking compound is administered in an amount and manner that inhibits an immune response to an extent that is sufficient, to treat an animal for a disease that requires downregulation of an immune response.

Suitable blocking therapeutic compounds include compounds that prevent the activation of an immunoregulatory cell through CD28 and/or CTLA4 by, for example, interfering with the binding of B7 protein to CD28 and/or CTLA4 by binding to either the B7 protein, or CD28 and/or CTLA4. Alternatively a blocking therapeutic compound can include a compound that binds to CD28 and/or CTLA4 but does not result in activation of a T cell upon binding. Preferably, a blocking compound is derived from a B7 or CTLA4 protein of the present invention. Examples of blocking compounds include an antibody of the present invention, that is administered to an animal in an effective manner (i.e., is administered in an amount so as to be present in the animal at a titer that is sufficient, upon interaction of that antibody with a native B7 or CTLA4 protein, to decrease B7 or CTLA4 activity in an animal, at least temporarily). Oligonucleotide nucleic acid molecules of the present invention can also be administered in an effective manner, thereby reducing expression of B7 or CTLA4 proteins in order to interfere with B7 or CTLA4 activity targeted in accordance with the present invention. Peptides of B7 or CTLA4 proteins of the present invention can also be administered in an effective manner, thereby reducing binding of B7 proteins to CD28 and/or CTLA4, or reducing binding of CTLA4 to B7, in order to interfere with B7 or CTLA4 activity targeted in accordance with the present invention. A blocking compound of B7 or CTLA4 function can be identified using B7 or CTLA4 proteins of the present invention. One embodiment of the present invention is a method to identify a compound capable of inhibiting B7 or CTLA4 function.

Such a method includes the steps of: (a) contacting (e.g., combining, mixing) an isolated B7 or CTLA4 protein of the present invention, with a putative inhibitory compound under conditions in which, in the absence of the compound, the B7 protein binds to CD28 or CTLA4, or the CTLA4 protein binds to B7, and (b) determining if the putative inhibitory compound inhibits the binding of B7 protein to CD28 or CTLA4, or the binding of CTLA4 protein to B7. Putative inhibitory compounds to screen include small organic molecules, antibodies (including mimetopes thereof), and ligand analogs. Such compounds are also screened to identify those that are substantially not toxic in host animals.

Inhibitors of B7 or CTLA4 function identified by such a method can be tested for their ability to block T cell activation in vivo. Preferred B7 or CTLA4 proteins to inhibit are those produced by dogs, cats, horses or humans, even more preferred B7 or CTLA4 proteins to inhibit are those produced by domestic dogs or cats. A particularly preferred inhibitor of the present invention is capable of regulating an immune response in an animal. It is also within the scope of the present invention to use inhibitors of the present invention to target diseases involving undesired helper T cell activity in animals. Compositions comprising inhibitors of B7 or CTLA4 function can be administered to animals in an effective manner to regulate the immune response in the animals, and preferably to prevent autoimmune disease, allergy or prevent graft rejection in animals, or to treat animals with such diseases. Effective amounts and dosing regimens can be determined using techniques known to those skilled in the art.

According to the present invention, different therapeutic compositions of the present invention can be used to administer to patients having a disease. In one embodiment, a therapeutic composition comprising a nucleic acid molecule that encodes a stimulatory activating B7 protein and/or stimulatory inactivating B7 protein is administered to an animal having cancer. Suitable nucleic acid molecules, and methods to deliver and express such molecules in an animal, are disclosed herein. Preferably, a nucleic acid molecule encoding a stimulatory inactivating B7 protein is delivered in amounts sufficient to produce low doses of stimulatory inactivating B7 protein. Preferably, a nucleic acid molecule encoding a stimulatory activating B7 protein is delivered in amounts sufficient to produce low doses of stimulatory activating B7 protein.

In another embodiment, a therapeutic composition comprising a nucleic acid molecule encoding a stimulatory activating B7 protein is administered to an animal susceptible to or having an infectious disease. Suitable nucleic acid molecules, and methods to deliver and express such molecules in an animal, are disclosed herein. Preferably, a nucleic acid molecule encoding a stimulatory activating B7 protein is delivered in amounts sufficient to produce low doses of stimulatory activating B7 protein. An infectious disease therapy preferably includes co-administration of an antigen derived from the pathogen causing an infectious disease. Suitable antigens can be selected by one of skill in the art depending on the pathogen, and can include parasites, viruses, bacteria and fungi. Preferred parasite antigens include heartworm; Yersinia. Pasteurella, Francisella, fleas; ticks, including both hard ticks of the family Ixodidae (e.g., Ixodes and Amblyomma) and soft ticks of the family Argasidae (e.g., Ornithodoros, such as O. parkeri and O. turicata); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Preferred viruses include FeLV and FIV. In addition, an infectious disease therapy can include co-administration of a compound capable of shifting an immune response to a TH1 response. An example of such a compound is IL12.

In another embodiment, a therapeutic composition comprising a high concentration of stimulatory activating and stimulatory inactivating B7 protein is administered to an animal having inflammation and/or autoimmune disease. Suitable proteins and methods to deliver and express such proteins in an animal are disclosed herein. Preferably, a stimulatory activating and stimulatory inactivating B7 protein is delivered to a localized area in an animal that is afflicted with inflammation or autoimmune disease. Localized areas can include, for example, joints or organs. As used herein, the term organ includes skin and lung, and other tissues understood to be organs by those of skill in the art.

In another embodiment, a therapeutic composition comprising a protein, and/or a nucleic acid molecule encoding a protein, including a stimulatory activating and stimulatory inactivating B7 protein, is administered to an animal having an allergy. Suitable proteins and nucleic acid molecules, and methods to deliver and express such proteins and nucleic acid molecules in an animal, are disclosed herein. Doses of an allergy therapy can vary depending upon the allergy being treated and the location of an allergic response. For example, one dose may be suitable for treatment of an allergy requiring topical administration compared with a dose suitable for treatment of an allergy requiring inhaled administration. One of skill in the art can select appropriate doses based on the allergy and mode of administration being used.

It is also within the scope of the present invention to use isolated proteins, mimetopes, nucleic acid molecules and antibodies of the present invention as diagnostic reagents. Methods to use such diagnostic reagents are well known to those skilled in the art.

The following examples are provided for the purposes of illustration and are not intended to limit the scope of the present invention.

EXAMPLES

It is to be noted that the examples include a number of molecular biology, microbiology, immunology and biochemistry techniques considered to be familiar to those skilled in the art. Disclosure of such techniques can be found, for example, in Sambrook et al., ibid. and Ausubel, et al., 1993, *Current Protocols in Molecular Biology,* Greene/Wiley Interscience, New York, N.Y., and related references. It should also be noted that since nucleic acid sequencing technology, and in particular the sequencing of PCR products, is not entirely error-free, that the nucleic acid and deduced protein sequences presented herein represent apparent nucleic acid sequences of the nucleic acid molecules encoding B7 or CTLA4 proteins of the present invention.

Example 1

This example describes the isolation and DNA sequencing of two forms of *Canis familiaris* B7-1 nucleic acid molecules.

A *C. familiaris* mitogen activated PBMC cDNA library was constructed in the Uni-ZAP® XR vector, available from Stratagene Cloning Systems, La Jolla, Calif., using Stratagene's ZAP-cDNA® Synthesis Kit and the manufacturer's protocol. The mRNA was isolated from *C. familiaris* peripheral blood mononuclear cells 4 hours after they were activated by a polyclonal activating agent in culture. A first polymerase chain reaction (PCR) product corresponding to a 3' portion of a canine B7-1 nucleic acid molecule was produced as follows. A pair of primers was used to amplify DNA from the CDNA library. A 3' T7 primer from the Uni-ZAPD® XR vector, available from Stratagene, was used in combination with a degenerate primer, the design of which was based on conserved regions of B7-1 cDNA sequences from other species in the public databases corresponding to the positions shown below:

| Database | Accession number | Nucleotides | Animal |
|---|---|---|---|
| gb | U57755 | 412–429 | cat |
| gb | M27533 | 729–746 | human |
| gb | U10925 | 708–725 | rat |
| dbj | D49843 | 430–447 | rabbit |
| gb | U19840 | 412–429 | rhesus monkey |

The degenerate primer is a 5' primer having the nucleic acid sequence 5' GTC ARA GCT GAC TTC CCT 3', where R can be either A or G, designated herein as SEQ ID NO:21. This degenerate primer for B7-1 was one of several degenerate primers tested and was the only primer that was found to be useful for the production of a canine B7-1 nucleic acid molecule. Initial attempts using a combination of several pairs of degenerate B7-1 primers to directly amplify finents of canine B7-1 nucleic acid molecules from the CDNA library or from mRNA by RT/PCR were unsuccessful. The PCR product was cloned and sequenced using an Applied Biosystems, Inc. automated DNA sequencer using standard methods.

A second PCR product corresponding to a 5' portion of a canine B7-1 nucleic acid molecule was produced as follows. A pair of primers was used to amplify DNA from the cDNA library. An antisense primer was designed using sequence derived from the first PCR product, the primer having the nucleic acid sequence 5' GTA GAA ACT CCT CAG AAC AAT G 3' (designated herein as SEQ ID NO:22), was used in combination with the 5' vector primer M13 Rev, available from Ufe Technologies, Gaithersburg, Md. This second PCR fragment was cloned and sequenced using standard methods.

To identify full-length B7-1 clones, the second PCR product was used to generate an about 545 base pair DNA fragment. The fragment was then labeled with $^{32}$P and used as a probe to screen the canine PBMC CDNA library. Hybridization was done at about 68° C. in 6×SSC, 5× Denhardt's solution, 0.5% SDS, 100 μg/ml of salmon sperm DNA and yeast tRNA. The blot was washed two times, for about 30 minutes per wash, at 55° C. in 1XSSC, 0.1%SDS. Positive clones were isolated and the CDNA inserts were sequenced for both strands using vector flanking primers and gene-specific internal primers. Sequence analysis was performed with DNAsis™0 using the alignment settings of: gap penalty set at 5; number of top diagonals set at 5; fixed gap penalty set at 10; k-tuple set at 2; window size set at 5 and floating gap penalty set at 10.

A. A first clone (Clone 14) was isolated, referred to herein as nCaB7-$1_{2830}$, contained in a recombinant molecule referred to herein as λ-nCaB7-$1_{2830}$, the coding strand of which was shown to have a nucleic acid sequence denoted herein as SEQ ID NO:1. The complement of SEQ ID NO:1 is represented herein by SEQ ID NO:3. Translation of SEQ ID NO:1 suggests that nucleic acid molecule nCaB7-$1_{2230}$ encodes a full-length B7-1 protein of about 304 amino acids, denoted herein as PCaB7-$1_{304}$, the amino acid sequence of which is presented in SEQ ID NO:2, assuming an open reading frame having an initiation codon spanning from nucleotide 337 through nucleotide 339 of SEQ ID NO:1 and a stop codon spanning from nucleotide 1249 through nucleotide 1251 of SEQ ID NO:1. The coding region encoding PCaB7-$1_{304}$ m is presented herein as nCaB7-$1_{912}$, which has the nucleotide sequence SEQ ID NO:4 (the coding strand) and SEQ ID NO:5 (the complementary strand). A putative signal sequence extends from amino acid residue 1 though residue 34 of SEQ ID NO:2. The proposed mature protein (i.e., canine B7-1 protein from which the signal sequence has been cleaved), denoted herein as PCaB7-$1_{270}$, contains about 270 amino acids, extending from residue 35 through residue 304 of SEQ ID NO:2. The nucleic acid molecule encoding PCaB7-$1_{270}$ is denoted herein as nCaB7-$s_{1810}$, extending from nucleotide 102 through nucleotide 912 of SEQ ID NO:4.

Comparison of nucleic acid sequence SEQ ID NO:1 with nucleic acid sequences reported in GenBank indicates that SEQ ID NO:1 showed the most homology, i.e., about 79.7% identity, between SEQ ID NO:1 and a feline B7-1 gene. Comparison of amino acid sequence SEQ ID NO:2 with amino acid sequences reported in GenBank indicates that SEQ ID NO:2 showed the most homology, i.e., about 79.1% identity, between SEQ ID NO:2 and a feline B7-1 protein.

B. A second clone (Clone 22) was isolated, referred to herein as nCaB7-$1_{1024}$, the coding strand of which was shown to have a nucleic acid sequence denoted herein as SEQ ID NO:11. The complement of SEQ ID NO:11 is referred to herein as SEQ ID NO:13. Translation of SEQ ID NO:11 suggests that nucleic acid molecule nCaB7-$1s_{1024}$ encodes a variant form of B7-1 protein of about 235 amino acids, denoted herein as PCaB7-$1s_{235}$, the amino acid sequence of which is presented in SEQ ID NO:12, assuming an open reading frame having an initiation codon spanning from nucleotide 79 through nucleotide 81 of SEQ ID NO:11 and a stop codon spanning from nucleotide 784 through nucleotide 786 of SEQ ID NO:11. The coding region encoding PCaB7-$1s_{235}$, not including the termination codon, is presented herein as nCaB7-$1s_{235}$, which has the nucleotide sequence SEQ ID NO:14 (the coding stand) and SEQ ID NO:15 (the complementary strand). A putative signal sequence extends from amino acid residue 1 through residue 34 of SEQ ID NO:12. The proposed mature protein (i.e., canine soluble B7-1 protein from which the signal sequence has been cleaved), denoted herein as PCaB7-$1s_{201}$, contains about 201 amino acids, extending from residue 35 through residue 235 of SEQ ID NO:12. The nucleic acid molecule encoding PCaB7-$1s_{201}$, is denoted herein as nCaB7-$1s_{603}$, extending from nucleotide 103 through nucleotide 705 of SEQ ID NO:14.

The open reading frame (ORF) of nCaB7-$1s_{1024}$ encodes a polypeptide of 235 amino acid residues, which is 69 residues shorter than the protein encoded by the nucleic acid molecule nCaB7-$1_{2830}$, which is 304 amino acid residues in length. Nucleotides 1 through 699 of nCaB7-$1_{2830}$ are shared by nucleic acid molecules nCaB7-$1s_{1024}$ and nCaB7-$1_{2830}$, which corresponds to the extracellular domain of B7-1. Nucleotides 700 through 912 of nCaB7-$1_{2830}$ are deleted in the nucleic acid molecule nCaB7-$1s_{1024}$. Thus, nucleic acid molecule nCaB7-$1s_{1024}$ lacks portions of the transmembrane and cytoplasmic domains of B7-1 present in nCaB7-$1_{2830}$. The sequence of nucleic acid molecules nCaB7-$1s_{11024}$ and nCaB7-$1_{2830}$ indicates that nCaB7-$1_{2830}$ encodes a soluble B7-1 protein and that nCaB7-$1_{2830}$ encodes a membrane bound form of B7-1. The 3' untranslated sequence of nCaB7-$1_{2830}$, however, differs from nCaB7-$1s_{1024}$. This suggests that the different forms of canine B7-1 are likely generated by alternate RNA splicing.

Example 2

This example describes the isolation and DNA sequencing of two forms of *Canis familiaris* B7-2 nucleic acid molecules.

The canine PBMC cDNA library constructed as in Example 1 was used to identify and isolate B7-2 nucleic acid molecules using the following method As a first step, a 322-bp PCR fragment encoding a portion of canine B7-2 was amplified using two degenerate primers. The primers were designed based on conserved regions of the B7-2 gene of mouse, rat and human.

| Primer | Database | Accession number | Nucleotides | Animal |
|---|---|---|---|---|
| F1 | gb | L25606 | 258–276 | mouse |
| F1 | gb | U31330 | 21–39 | rat |
| F1 | gb | L25259 | 266–284 | human |
| B1 | gb | L25606 | 576–554 | mouse |
| B1 | gb | U31330 | 339–317 | rat |
| B1 | gb | L25259 | 584–562 | human |

A sense degenerate primer, referred to as F1, having the nucleic acid sequence 5' GTA GTA TTT TGG CAG GAC C 3' (designated SEQ ID NO:23), was used in combination with an antisense degenerate primer, referred to as B1, having the nucleic acid sequence 5' TAG AYG SGC AGG TCA AAT TTA TG 3' (designated SEQ ID NO:24), where Y can be either C or T, and S can be either C or G. Initial attempts using numerous degenerate B7-2 primers to directly amplify figments of canine B7-2 nucleic acid molecules from the cDNA library were unsuccessful. The resulting 322-bp PCR product was cloned and sequenced using an Applied Biosystems, Inc. automated DNA sequencer using standard methods.

To identify full-length B7-2 clones, the 322-bp PCR product was labeled with 32P and used as a probe to screen the canine PBMC cDNA library. Hybridization was performed as described in Example 1. Positive clones were isolated and the cDNA inserts were sequenced for both strands using vector flanking primers and gene-specific internal primers. Sequence analysis was performed with DNAsis™ using the settings described in Example 1.

A. clone (Clone 10) was isolated, referred to herein as nCaB7-$2_{1897}$, contained in a recombinant molecule referred to herein as λ-nCaB7-$2_{1897}$, the coding strand of which was shown to have a nucleic acid sequence denoted herein as SEQ ID NO:6. The complement of SEQ ID NO:6 is represented herein by SEQ ID NO:8. Translation of SEQ ID NO:6 suggests that nucleic acid molecule nCaB7-$2_{1897}$ encodes a full-length B7-2 protein of about 329 amino acids, denoted herein as PCaB7-$2_{329}$, the amino acid sequence of which is presented in SEQ ID NO:7, assuming an open reading frame having an initiation codon spanning from nucleotide 6 through nucleotide 8 of SEQ ID NO:6 and a stop codon spanning from nucleotide 993 through nucleotide 995 of SEQ ID NO:6. The coding region encoding PCaB7-$2_{329}$, not including the termination codon, is presented herein as nCaB7-$2_{987}$, which has the nucleotide sequence SEQ ID NO:9 (the coding strand) and SEQ ID NO:10 (the complementary strand). A putative signal sequence extends from amino acid residue 1 through residue 22 of SEQ ID NO:6.

The proposed mature protein (i.e., canine B7-2 protein from which the signal sequence has been cleaved), denoted herein as PCaB7-$2_{307}$, contains about 307 amino acids, extending from residue 23 though residue 329 of SEQ ID NO:7. The nucleic acid molecule encoding PCaB7-$2_{307}$. is denoted herein as nCaB7-$2_{921}$, extending from nucleotide 66 through nucleotide 987 of SEQ ID NO:9.

Comparison of nucleic acid sequence SEQ ID NO:6 with nucleic acid sequences reported in GenBank indicates that SEQ ID NO:6 showed the most homology, i.e., about 77.2% identity, between SEQ ID NO:6 and a swine B7-2 gene. Comparison of amino acid sequence SEQ ID NO:7 with amino acid sequences reported in GenBank indicates that SEQ ID NO:7 showed the most homology, i.e., about 56.3% identity, between SEQ ID NO:7 and a swine B7-2 protein.

B. Another clone (Clone 1) was isolated, referred to herein as nCaB7-$2s_{1795}$ the coding strand of which was shown to have a nucleic acid sequence denoted herein as SEQ ID NO:16. The complement of SEQ ID NO:16 is represented herein by SEQ ID NO:18. Translation of SEQ ID NO:16 suggests that nucleic acid molecule nCaB7-$2s_{1795}$ encodes a variant form of B7-2 protein of about 280 amino acids, denoted herein as PCaB7-$2s_{280}$ the amino acid sequence of which is presented in SEQ ID NO:17, assuming an open reading frame having an initiation codon spanning from nucleotide 7 through nucleotide 9 of SEQ ID NO:16 and a stop codon spanning from nucleotide 847 through nucleotide 849 of SEQ ID NO:16. The coding region encoding PCaB7-$2s_{280}$, not including the termination codon, is presented herein as nCaB7-2s840, which has the nucleotide sequence SEQ ID NO:19 (the coding strand) and SEQ ID NO:20 (the complementary strand). SEQ ID NO:16 is predicted to encode a B7-2 protein lacking at least a portion of the transmembrane domain. A putative signal sequence extends from amino acid residue 1 through residue 22 of SEQ ID NO:17. The proposed mature protein (i.e., canine soluble B7-2 protein from which the signal sequence has been cleaved), denoted herein as PCaB7-$2s_{258}$, contains about 258 amino acids, extending from residue 23 through residue 280 of SEQ ID NO:17. The nucleic acid molecule encoding PCaB7-$2s_{258}$, is denoted herein as nCaB7-$2s_{774}$, extending from nucleotide 66 through nucleotide 840 of SEQ ID NO:19.

C. The ORF of nCaB7-$2s_{1795}$ encodes a polypeptide of 280 amino acid residues, which is 49 residues shorter than the protein encoded by the nucleic acid molecule nCaB7-$2_{1897}$, which is 329 amino acid residues in length. Nucleotides 1 through 702 of nCaB7-$2_{1897}$ mare shared by nucleic acid molecules nCaB7-$2s_{1795}$ and nCaB7-$2_{1897}$, which corresponds to the extracellular domain of B7-2. Nucleotides 703 through 852 of nCaB7-$2_{1897}$ are deleted in the nucleic acid molecule nCaB7-$2s_{1795}$, which corresponds to a portion of the transmembrane domain of B7-2. Nucleotides 853 through 907 of nCaB7-$2_{1897}$ are identical to nucleotides 703 through 840 of nucleic acid molecule nCaB7-$2s_{1795}$, which corresponds to the intracellular domain of B7-2. Thus, nucleic acid molecule nCaB7-$2t_{1795}$ lacks a portion of the transmembrane domain of B7-2 present nCaB7-$2_{1897}$. The sequence of nucleic acid molecules nCaB7-$2s_{1795}$ and nCaB7-$2_{1897}$ indicates that nCaB7-$2_{1795}$ encodes a soluble B7-$2s_{1795}$ protein and that nCaB7-$2_{1897}$ encodes a membrane bound form of B7-2. The different forms of canine B7-2 are encoded by contiguous sequence, differing by the location of their respective termination codons. The different locations of termination codons may be due to alternative RNA splicing, due to the existence of two different genes or due to DNA recombination.

A search of the databases revealed that predicted amino acid sequences of the canine B7-1 and B7-2 proteins, similar to those of mouse B7 proteins, shared homology with members of the immunoglobulin (Ig) superfamily due to the presence of two contiguous Ig-like domains in the extracellular region. The first canine B7 Ig domain is consistent with the structure of an Ig V domain. The second canine B7 Ig domain is consistent with the structure of an Ig C domain. For the full-length canine B7-1, the IgV-like domain extends from residue 34 to residue 139 SEQ ID NO:2, and the IgC-like domain extends from residue 140 to residue 233 of SEQ ID NO:2. For the secreted canine B7-1, the IgV-like domain extends from residue 34 to residue 139 SEQ ID NO:12, and the IgC-like domain extends from residue 140 to residue 235 of SEQ ID NO:12.

Example 3

This example describes the production of recombinant molecules encoding different forms of canine B7-1 and B7-2 proteins, and the expression of these recombinant molecules in mammalian cells.

A. A recombinant expression plasmid, denoted herein as pCMV-nCaB7-$2_{1897}$, capable of expressing a full length form of B7-2, was produced as follows. Recombinant molecule λ-nCaB7-$2_{1897}$ was digested with the restriction endonucleases BamH I and Xho I. The 1897-bp insert encoding full-length B7-2 was gel purified and ligated into the HCMV immediate-early transcription control region of the pCMV-Int A plasmid vector that had been digested with BamH I and Xho I and gel purified, to produce the recombinant molecule pCMV-nCaB7-$2_{1897}$. The insert size and identity were confirmed by reaction digestion, PCR, and sequencing The pCMV-Int A plasmid vector was produced as follows. Vector pRc/RSV, available from Invitrogen Corp., San Diego, Calif., was cleaved by restriction enzyme with PvuII, and the 2963-base pair PvuII fragment was gel purified. The fragment was self-ligated to form the vector pRc/RSV(Pvu), which contains a Rous Sarcoma Virus (RSV) long terminal repeat, a multiple cloning site, a bovine growth hormone polyadenylation sequence, a bacterial origin of replication, and an ampicillin resistance gene. Vector pRc/RSV(Pvu) was retraction enzyme digested using HindIII and NruI. A HindIII/SspI fragment containing the HCMV intermediate early promoter and first intron (i.e., intron A) was ligated into the digested pRc/RSV(Pvu) vector to produce the vector pCMV-Int A.

B. A second recombinant expression clone, denoted herein as pCMV-nCaB7-$1_{1385}$, capable of expressing a full length form of B7-1, was produced as follows. Nucleic acid molecule λ-nCaB7-$1_{2830}$ was digested with the restriction endonuclease PstI to produce a 1385-bp PstI fragment The 1385-bp fragment encoding full-length B7-1 was gel purified and ligated into the plasmid vector pCMV-Int A that had been digested with PstI and gel purified, to produce the recombinant molecule pCMV-nCaB7-$1_{1385}$. Insert size and identity were confirmed by restriction digestion, PCR, and sequencing.

C. Stable expression of recombinant canine B7-1 and B7-2 in mammalian cells carrying the recombinant plasmids, pCMV-nCaB7-$2_{1897}$ or pCMV-nCaB7-$1_{1385}$ was demonstrated by introducing these plasmids into Chinese Hamster Ovary cells (CHO, available from ATCC, as follows. Briefly, six-well polystyrene tissue culture plates were seeded with approximately 5×10⁵/well in 2 ml of MEM, available from Life Technologies, supplemented with 100 mM L-glutamine, gentamicin, and 10% FBS (TCM). Cells were grown to about 80% confluence (about 18 hrs). The recombinant molecules to be transfected were purified using the 5' Prime to 3' Prime Kit, available from 5' to 3', Inc., Boulder, Colo., as per the manufacturer's instructions. The recombinant plasmids were linearized using the restriction enzyme PvuI. The plasmid pcDNA3, available from Invitrogen, which contains the neomycin resistance gene, was linearized with the restriction enzyme EcoRI. Approximately 2 μg ofpCMV-nCaB7-$2_{1897}$ or pCMV-nCaB7-$1_{1385}$, were mixed separately with about 2 ng of pcDNA3 in about 100 μl OptiMEM medium, available from Life Technologies. About 10 μl Lipofectamine, available from Life Technologies, was mixed with about 100 μl OptiMEM. The plasmid mixture was then added to the Lipofectamine mixture and incubated at room temperature for about 45 min. After incubation, about 800 μl of OptiMEM was added, and the entire mixture was overlaid onto the CHO cells that had been rinsed with OptiMEM. Cells were incubated for about 5 hours at 37° C., 5% $CO_2$, 95% relative humidity. Approximately 1 ml of TCM with 20% FBS was added, and the cells were incubated overnight. The media was changed after about 24 hr. About 72 hr post transfection, the cells were split 1:4 and put into selection TCM containing about 400 μg/ml geneticin (G418), available from Life Technologies. The media was changed every 3–5 days. After several weeks, G418-resistant colonies were trypsinized using cloning cylinders, and the cells were plated into 24 well plates. The resulting recombinant cells are referred to herein as CHO-pCMV-nCaB7-$2_{1897}$ and CHO-pCMV-nCaB7-$1_{1385}$, respectively. The recombinant cells were then expanded for testing.

Example 4

This example describes the mitogen costimulatory activity of B7-2 protein expressed in CHO-pCMV-nCaB7-$2_{1897}$ or B7-1 protein expressed in CHO-pCMV-nCaB7-$1_{1385}$ cells.

The stable transfectants produced in Example 3 were tested in a mitogen costimulatory assay for expression of full length B7 molecules as follows. Briefly, CHO-pCMV-nCaB7-$2_{1897}$ or CHO-pCMV-nCaB7-$1_{1385}$ cells were trypsinized and plated into 96 well flat bottom plates at about 5×10⁴cells/well. After about 18–24 hrs, the CHO-pCMV-nCaB7-$2_{1897}$ or CHO-pCMV-nCaB7-$1_{1385}$ cells were fixed with about 1% paraformaldehyde in phosphate buffered saline (PBS) for about 15 mins at room temperature and then washed extensively with PBS. About 5×10³ to about 5×10⁴ resting canine T cells were added to the wells containing the CHO-pCMV-nCaB7-$2_{1897}$ or CHO-pCMV-nCaB7-$1_{1385}$ cells in the absence or presence of approximately 0.1 to 1 μg/ml Concanavalin A (Con A; available from Sigma, St Louis, Mo.). The cultures were incubated at about 37° C., 5% $CO_2$, 95% relative humidity for about 5 to 7 days. About 1 μCi tritiated thymidine was added to each well for the last 18 to 24 hrs of the incubation The cells were harvested onto filter mats which were then counted. The stimulation indices using 1 or 0.1 μg/ml Con A are shown below in Tables 1 and 2.

TABLE 1

Costimulation of resting canine T cells
by Recombinant B7-2 Protein

| Con A | CHO | B7-2 Transfectant | B7-2 Transfectant |
|---|---|---|---|
| 1.0 μg/ml | 3 | 14 | 16 |
| 0.1 μg/ml | 2 | 19 | 16 |
| None | 2 | 1 | 1 |

TABLE 2

Costimulation of resting canine T cells
by Recombinant B7-1 Molecules

| Con A | CHO | B7-1 Transfectant | B7-1 Transfectant |
|---|---|---|---|
| 1.0 μg/ml | 3 | 13 | 50 |
| 0.1 μg/ml | 2 | 12 | 34 |
| None | 1 | 1 | 1 |

The results indicated that the B7-2 or B7-1 recombinant proteins expressed by recombinant cells CHO-pCMV-nCaB7-$2_{1897}$ or CHO-pCMV-nCaB7-$1_{1385}$, respectively, are capable of stimulating resting T cells.

Example 5

This example describes the isolation and DNA sequencing of Felis B7-2 nucleic acid molecules.

A Fells mitogen activated PBMC cDNA library was constructed in the Uni-ZAPS® XR vector using the methods described above in Example 1. As a first step in the isolation of full-length feline B7-2 cDNA, a 322-bp PCR fragment encoding a portion of feline B7-2 was amplified from the cDNA library using the two degenerate primers described above in Example 2. To identify full-length B7-2 clones, the 322-bp PCR product was labeled with $^{32}$P and used as a probe to screen the feline PBMC cDNA library using the hybridization conditions described above in Example 1. Positive clones were isolated and the cDNA inserts were sequenced for both strands using vector flanking primers and gene-specific internal primers. Sequence analysis was performed with DNAsis™ using the settings described above in Example 1.

A clone (Clone 4–6) was isolated, referred to herein as nFeB7-$2_{2830}$, contained in a recombinant molecule referred to herein as λ-nFeB7-$2_{2830}$, the coding strand of which was shown to have a nucleic acid sequence denoted herein as SEQ ID NO:25. The complement of SEQ ID NO:25 is represented herein by SEQ ID NO:27. Translation of SEQ ID NO:25 suggests that nucleic acid molecule nFeB7-$2_{22830}$ encodes a full-length B7-2 protein of about 332 amino acids, denoted herein as PFeB7-$2_{332}$, the amino acid sequence of which is presented in SEQ ID NO:26, assuming an open reading frame having an initiation codon spanning from nucleotide 179 through nucleotide 181 of SEQ ID NO:25 and a stop codon spanning from nucleotide 1175 through nucleotide 1177 of SEQ ID NO:25. The coding region encoding PFeB7-$2_{332}$, not including the termination codon, is presented herein as nFeB7-$2_{996}$, which has the nucleotide sequence SEQ ID NO:28 (the coding strand) and SEQ ID NO:29 (the complementary strand). A putative signal sequence extends from amino acid residue 1 through residue 23 of SEQ ID NO:26. The proposed mature protein (i.e., feline B7-2 protein from which the signal sequence has been cleaved), denoted herein as PFeB7-$2_{309}$ contains about 309 amino acids, extending from residue 24 through residue 329 of SEQ ID NO:26. The nucleic acid molecule encoding PFeB7-$2_{309}$ is denoted herein as nFeB7-$2_{918}$, extending from nucleotide 69 through nucleotide 996 of SEQ ID NO:28.

Comparison of nucleic acid sequence SEQ ID NO:25 with nucleic acid sequences reported in GenBank indicates that SEQ ID NO:25 showed the most homology, i.e., about 76.9% identity, between SEQ ID NO:25 and a swine B7-2 gene. Comparison of amino acid sequence SEQ ID NO:26 with amino acid sequences reported in GenBank indicates that SEQ ID NO:26 showed the most homology, i.e., about 57.5% identity, between SEQ ID NO:26 and a swine B7-2 protein.

Example 6

This example describes the identification of transcripts encoding a soluble form of feline B7-2.

In order to identify different forms of feline B7-2, first strand cDNA was synthesized from felis lymph node and spleen cells using methods described above in Example 1. The cDNA was used as a template for PCR with feline B7-2 specific sense primers 5'ATA CAA GGT TAC CCA GAA CC 3' (designated herein as SEQ ID NO:51), corresponding to nucleotides 662–681 of SEQ ID NO:25; and antisense primer 5' TGT GTA GTA CTT TTG TCG CC 3' (designated herein as SEQ ID NO:52), corresponding to the reverse complement of nucleotides 1151–1170 of SEQ ID NO:25. The PCR reaction resulted in the amplification of two nucleic acid molecules, having sizes of about s509 base-pairs and about 359 base-pairs, respectively. The two PCR products were cloned and subjected to nucleotide sequencing using standard methods.

The larger fragment, denoted herein as nFeB7-$2_{509}$, has a coding strand corresponding to nucleotides 662–1170 of SEQ ID NO:25, represented herein as SEQ ID NO:30. The complement of SEQ ID NO:30 is represented herein as SEQ ID NO:32. Nucleic acid molecule nFeB7-$2_{509}$ encodes a B7-2 protein of about 169 amino acids, denoted herein as PFeB7-$2_{169}$, the amino acid sequence of which is presented in SEQ ID NO:31, assuming an open reading frame spanning from nucleotide 1 through nucleotide 507 of SEQ ID NO:30, SEQ ID NO:31 corresponds to amino acids 162–330 of SEQ ID NO:26.

The smaller fragment, denoted herein as nFeB7-$2s_{359}$, has a coding strand represented herein as SEQ ID NO:33. The complement of SEQ ID NO:33 is represented herein as SEQ ID NO:35. SEQ ID NO:33 is identical to SEQ ID NO:30, except for a deletion of 150 nucleotides extending from nucleotide 226 to nucleotide 375 of SEQ ID NO:30, and from nucleotide 887 to nucleotide 1036 of SEQ ID NO:25. Nucleic acid molecule nFeB7-$2s_{359}$, encodes a B7-2 protein of about 119 amino acids, denoted herein as PFcB7-$2s_{119}$, the amino acid sequence of which is presented in SEQ ID NO:34, assuming an open reading frame spanning from nucleotide 1 through nucleotide 357 of SEQ ID NO:30.

SEQ ID NO:30 and SEQ ID NO:33 were aligned with the canine B7-2 nucleic acid molecules isolated as described in Example 2. The nucleotides deleted in SEQ ID NO:33 relative to SEQ ID NO:30 corresponded to the nucleotides deleted in nucleic acid molecule nCaB7-$2s_{1795}$ (SEQ ID NO:16), which encodes a soluble canine B7-2, relative to nCaB7-$2_{1897}$ (SEQ ID NO:6), that encodes a membrane bound form of B7-2. The length of the deleted fragment in nFCB7-$2s_{359}$ was 150 nucleotides and that in nCaB7-$2s_{1795}$, was 147 nucleotides. This suggests that the transcript encoding soluble feline B7-2 is generated by the same mechanism that was described for canine B7-2 in Example 2.B., i.e., by deletion of the transmembrane domain exon.

Example 7

This example describes the identification and cloning of a cDNA molecule encoding a truncated form of feline B7-1.

In order to identify different forms of feline B7-1, the Felis PBMC cDNA library, constructed as described in Example 5, was used as a template for PCR with feline B7-1-specific sense primer 5' GGG AAT TCG CCA CCA TGG GTC ACG CAG CAA AGT G 3', designated herein as SEQ ID NO:53, with nucleotides 15–34 corresponding to nucleotides 1–20 of GenBank accession number U57755; and as the antisense primer either feline B7-1-specific antisense primer 5' CCC TCG AGC TAT GTA GAC AGG TGA GAT C 3',designated herein as SEQ ID NO:54, with nucleotides 9–28 corresponding to the reverse complement of nucleotides 860–879 of GenBank accession number U57755; or the λ-Zap vector primer T7 5' GTA ATA CGA CTC ACT ATA GGG C 3',designated herein as SEQ ID NO:55, available from Stratagene. To facilitate translation in eukaryotic cells and cloning into pCMV-IntA as described in Example 8, an Eco RI site and Kozak translation start sequence (shown in bold) were added to the sense primer SEQ ID NO:53, and an xho I site (shown in bold) was added to the antisense primer SEQ ID NO:54. The fragment amplified using the two feline B7-1-specific primers was 879 nucleotides in length, corresponding to the predicted coding region of full-length feline B7-1. When the λ-Zap vector primer T7 was used, a predominant fragment of 594 base-pairs was amplified The 594-base-pair fragment was cloned and subjected to nucleotide sequencing using standard methods.

The cloned 594base-pair nucleic acid molecule, referred to herein as nFeB7-1s$_{594}$, has a coding strand having the nucleic acid sequence denoted herein as SEQ ID NO:36. The reverse complement of SEQ ID NO:36 is represented herein by SEQ ID NO:38. Translation of SEQ ID NO:36 suggests that nucleic acid molecule nFeB7-1s$_{594}$ encodes a truncated B7-1 protein of about 173 amino acids, denoted herein as PFeB7-1s$_{173}$, the amino acid sequence of which is presented in SEQ ID NO:37, assuming an open reading frame having an initiation codon spanning from nucleotide 1 through nucleotide 3 of SEQ ID NO:36 and a stop codon spanning from nucleotide 520 through nucleotide 522 of SEQ ID NO:36. The coding region encoding PFeB7-1s$_{173}$, not including the termination codon, is presented herein as neB7-1s$_{519}$, which has the nucleotide sequence SEQ ID NO:39 (the coding strand) and SEQ ID NO:40 (the complementary strand). At the nucleotide level, the first 408 nucleotides of SEQ ID NO:36 were identical to the fast 408 nucleotides of coding region of full-length feline B7-1, as represented by Genbank accession number U57755, but the remaining sequences, i.e., nucleotides 409–594, were unique. At the amino acid level, the first 139 residues of SEQ ID NO:37 were identical to the first 139 residues of full-length feline B7-1 as represented by PID accession number g2065521, but the remaining sequence, i.e., amino acids 140–173, were unique.

Both full-length and the truncated forms of feline B7-1 transcripts were expressed by spleen and lymph node cells of cats as indicated by RT-PCR of messenger RNA isolated from these cells. RT-PCR reactions were carried out with primers specific for the full-length feline B7-1 using sense primer 5' ACC ACT CCA TTG TGA TCA TG 3', denoted herein as SEQ ID NO:56, and corresponding to nucleotides 293–312 of GenBank accession number U57755; and antisense primer SEQ ID NO:54. RT-PCR reactions were also carried out with primers specific for the truncated form of feline B7–1 using sense primer SEQ ID NO:53; and antisense primer 5' GTC TTG ATC TCA GGG TCA TG 3', denoted herein as SEQ ID NO:57, and corresponding to the reverse complement of nucleotides 465–484 of SEQ ID NO:36. The RT-PCR reaction amplified fragments of 587 and 484 base pairs, which corresponded to the full-length and truncated forms of feline B7-1.

When compared to the domain structure of B7-1 from human, mouse and dog, the divergence point of the truncated feline B7-1 amino acid sequence, i.e. between amino acid residues 139 and 140 of SEQ ID NO:38, corresponded to the junction between the IgV- and IgC-like domains in the extracellular regions of the human, mouse, and dog molecules. It is likely that, while the soluble form of canine B7-1, as described in Example 2.C, consists of both IgV- and IgC like domains, soluble feline B7-1 consists of only the IgV-like domain. Previous work by Rennert et al., *Int. Immunol.*, Vol. 9, pp. 805–813, 1997, indicated that a fusion protein consisting of the IgV-like domain of human B7-1 did not bind to CTLA4 while a fusion protein consisting of the IgV-like domain of human B7-2 or IgV- and IgC-like domains of either B7-1 or B7-2 bound to CTLA4. It is not known at the present time whether the feline B7-1 protein encoded by the truncated transcript can bind to B7 receptors CD28 or CTLA4.

Example 8

This example describes the production of recombinant molecules encoding feline B7-1 and B7-2 proteins, and the expression of these recombinant molecules in mammalian cells.

A. A recombinant plasmid, denoted herein as pCMV-nFeB7-1$_{879}$, capable of expressing a full length form of B7-1, was produced as follows. Feline B7-1 was cloned from the feline PBMC cDNA library, produced as described in Example 5, by PCR using the feline B7-1 gene-specific primers SEQ ID NO:53 and SEQ ID NO:54. The resulting PCR fragment was first cloned into pCR2.1 (Invitrogen), and then the insert was excised with restriction endonucleases Eco RI and Xho I. The insert was gel purified and ligated into the HCMV immediate-early transcription control region of the pCMV-Int A plasmid vector, produced as described in Example 3.A., that had been digested by Eco RI and Aho I and gel purified, to produce recombinant molecule pCMV-nFeB7-1$_{879}$. Insert size and identity were confirmed by restriction digestion, PCR, and sequencing.

B. A recombinant plasmid, denoted herein as pCMV-nFeB7-2$_{999}$, capable of expressing a full length form of feline B7-2, was produced as follows. The complete coding region encoding feline B7–2, i.e., nucleotides 179–1177 of SEQ ID NO:25, was amplified by PCR from full length cDNA nFeB7-2$_{2830}$ with the following gene specific primers: sense primer 5' GCG GAT CCA CCA TGG GCA iTT GTG ACA GCA C 3', denoted herein as SEQ ID NO:58, with nucleotides 12–31 corresponding to nucleotides 179–198 of SEQ ID NO:25; and antisense primer 5' GCC TCG AGT TAA AAA TGT GTA GTA CTT TTG TCG 3', denoted herein as SEQ ID NO:59, with nucleotides 9–33 corresponding to the reverse complement of nucleotides 1153–1177 of SEQ ID NO:25. To facilitate cloning into pCMV-IntA, a Bam H1 site (shown in bold) was added to the sense primer SEQ ID NO:58, and an Xho I site (shown in bold) was added to the antisense primer SEQ ID NO:59. The PCR-amplified nucleic acid molecule nFeB7-2$_{999}$ was digested with restriction endonucleases Bam H1 and Xho I. The insert was gel purified and ligated into the HCMV immediate-early transcription control region of the pCMV-IntA plasmid vector, produced as described in Example 3.A., that had been digested by Bam H1 and Xho 1 and gel purified, to pie recombinant molecule pCMV-nFeB7-2$_{999}$. The insert size and identity were confirmed by restriction digestion, PCR, and sequencing.

C. Stable recombinant cells individually expressing recombinant plasmids pCMV-nFeB7-2$_{999}$ and pCMV-nFeB7-1$_{879}$ were established in mouse L-M (TK-) cell fibroblasts (L cells, available from ATCC) as follows. Briefly, six-well polystyrene tissue culture plates were seeded with approximately 5×10$^5$ cells/well in 2 ml of DMEM, available from Life Technologies, supplemented with 100 mM L-glutamine, gentamicin, and 10% FBS (L-TCM). Cells were grown to about 80% confluence (about 18 hr). The recombinant plasmids to be transfected were purified using the 5 Prime to 3 Prime Kit as per the manufacturer's instructions. The recombinant plasmids were linearized with the restriction enzyme PvuI. The plasmid PMLBKTK, available from ATCC, which contains the thymidine kinase gene was also linearized with PvuI. Approximately 2 μg of recombinant plasmid DNA and 0.2 μg of PMLBKTK were mixed with about 100 μl OptiMEM medium, available from Life Technologies. About 10 μt Lipofectamine, available from Life Technologies, was mixed with 100 μl OptiMEM. The plasmid mixture was then added to the Lipofectamine mixture and incubated at room temperature for about 45 min. After incubation, about 800 μl of OptiMEM was added, and the entire mixture was overlaid onto the L cells that had been rinsed with OptiMEM. Cells were incubated for 5 hours at 37° C., 5% CO$_2$, 95% relative humidity. Approximately 1 ml of LTCM with 20% FBS was added, and the cells were incubated overnight. The media was changed after about 24 hr. About 72 hr post transfection, the cells were split 1:4 and put into selection L-TCM containing 1× HAT, available from Sigma. The media was changed every 3–5 days. After several weeks, HAT-resistant colonies were trypsinized using cloning cylinders, and the cells were plated into 24 well plates. The resulting recombinant cells are referred to herein as L-pCMV-nFeB7-2$_{999}$ and L-pCMV-nFeB7-1$_{879}$ respectively. The recombinant cells were then expanded for testing.

Example 9

This example describes the detection of expression of feline B7-2 protein expressed in L-pCMV-nFeB7-2$_{999}$ or feline B7-1 protein expressed in L-pCMV-nFeB7-1$_{879}$ Recombinant cells L-pCMV-nleB7-2$_{999}$, and L-pCMV-neB7-1$_{879}$, produced as described in Example 8, were tested for surface expression of feline B7-1 or B7-2 by determining if hwnan CTLA4 will bind. Briefly, 1×10$^5$ (per condition) L-pCMV-nFeB7-2$_{999}$ or L-pCMV-nFeB7-1$_{879}$ cells or, as a negative control, L cells transfected with the empty pCMV vector and the PMBKTK plasmid (L-CMV) were incubated in phosphate buffered saline (PBS) containing 30% fetal bovine serum (FBS) for about 30 min on ice. The cells were then spun down and treated with the following:

| Primary incubation | Secondary Incubation |
|---|---|
| Human CTLA4/Fc | Mouse anti human IgG Fc FTTC |

Human CTLA4 Fc chimeric protein, available from R&D systems, Minneapolis, Minn., was used at about 20 μg/ml. Mouse anti human IgG Fc FITC, available from Sigma, was used at about 65 μg/ml. These reagents were diluted in PBS/5% FBS. All incubations were performed in about 100 μl for about 1 hr on ice with 3 washes of PBS/5% FBS in between each incubation. Cells were then analyzed on a flow cytometer (MoFlow Desk Top System, Cytomation, Ft Collins, Colo.) with the fluorescein gate set at 10$^1$. The results arc shown below in Table 3.

TABLE 3

Binding of human CTLA4/Fc chimeric protein to feline B7-2 and B7-1 molecules expressed on L cell transfectants.

| Cells | % positive |
|---|---|
| L-CMV | 1 |
| L-pCMV-nFeB7-2$_{999}$ | 98 |
| L-pCMV-nFeB7-1$_{879}$ | 84 |

This experiment shows that feline B7-2 and B7-1 expressed on the membrane of L cell tansfectants are able to bind to recombinant CTLA4 protein.

Example 10

This example describes the expression of canine B7-1 and B7-2 proteins in mammalian cells. Stable recombinant cells individually expressing recombinant. plasmids pCMV-nCaB7-2$_{1897}$ and pCMV-nCaB7-1$_{1385}$, produced as described in Examples 3.A and 3.B., respectively, were established in mouse L cells by the method described in Example 8.C. The resulting recombinant cells are referred to herein as L-pCMV-nCaB7-2$_{1897}$ and L-pCMV-nCaB7-1$_{1385}$, respectively. The recombinant cells were then expanded for testing.

Example 11

This example describes the cloning of CDNA encoding Canis and Felis CTLA4.

Two oligonucleotide primers were made according to conserved regions of human, bovine, rabbit, mouse, and rat CTLA4 gene sequences available in GenBank: sense primer, 5' GTG AAC CTS ACY ATC CAA GG 3', where S was either G or C and Y was either T or C, denoted herein as SEQ ID NO:60; and antisense primer, 5' GCA TTT TCA CAT AGA CCC CTG 3', denoted herein as SEQ ID NO:61. The primers correspond to the positions as shown below:

| Database | Accession Number | Nucleotides Sense | Antisense | Animal |
|---|---|---|---|---|
| gb | X05719 | 391–410 | 650–670 | mouse |
| gb | U37121 | 334–353 | 593–613 | rat |
| gb | L15006 | 334–353 | 593–613 | human |

-continued

| Database | Accession Number | Nucleotides Sense | Antisense | Animal |
|---|---|---|---|---|
| gb | X93305 | 328–347 | 587–607 | cattle |
| dbj | D49844 | 382–401 | 641–661 | rabbit |

A. A 280 nucleotide fragment of canine CTLA4, obtained by PCR using the two primers described above, was used to isolate from the canine PBMC CDNA library, prepared as described in Example 1, a clone (Clone 21), referred to herein as nCaCTLA4$_{1856}$, the coding strand of which was shown to have nucleic acid sequence SEQ ID NO:41. The reverse complement of SEQ ID NO:41 is referred to herein as SEQ ID NO:43. Translation of SEQ ID NO:41 suggests that nucleic acid molecule nCaCTLA4$_{1856}$ encodes a CTLA4 protein of 223 amino acids, denoted herein as PCaCTLA4$_{223}$, the amino acid sequence of which is presented in SEQ ID NO:42, assuming an open reading frame having an initiation codon spanning from nucleotide 60 through nucleotide 62 of SEQ ID NO:41 and a stop codon spanning from nucleotide 729 through nucleotide 731 of SEQ ID NO:41. The coding region encoding PCaCTLA4$_{223}$, not including the termination codon, is presented herein as nCaCTLA4$_{669}$, which has the nucleotide sequence SEQ ID NO:44 (the coding strand) and SEQ ID NO:45 (the complementary strand).

B. A 280 nucleotide fragment of feline CTLA4 obtained by PCR using the two primers described above was used to isolate from the feline PBMC CDNA library, prepared as described in Example 5, a clone (Clone 16), referred to herein as nFeCTLA4$_{1883}$, the coding strand of which was shown to have a nucleic acid sequence SEQ ID NO:46. The reverse complement of SEQ ID NO:46 is referred to herein as SEQ ID NO:48. Translation of SEQ ID NO:46 suggests that nucleic acid molecule nFeCTLA4$_{1883}$ encodes a CTLA4 protein of 223 amino acids, denoted herein as PFeCTLA4$_{223}$, the amino acid sequence of which is presented in SEQ ID NO:47, assuming an open reading frame having an initiation codon spanning from nucleotide 69 through nucleotide 71 of SEQ ID NO:46 and a slop codon spanning from nucleotide 738 through nucleotide 740 of SEQ ID NO:46. The coding region encoding PFeCTLA4$_{223}$, not including the termination codon, is presented herein as nFCCTLA4$_{669}$, which has the nucleotide sequence SEQ ID NO:49 (the coding strand) and SEQ ID NO:50 (the complementary strand).

Sequence analysis was performed with DNAsis™ using the alignment settings of: gap penalty set at 5; number of top diagonals set at 5; fixed gap penalty set at 10; k-tuple set at 2; window size set at 5 and floating gap penalty set at 10. At the amino acid level, PCaCRtA4$_{223}$, shared 88.5%, 88.2%, 87.4%, 76.7%, and 76.2% of identity with the CTLA4 proteins of rabbit, bovine, human, mouse, and rat, respectively. PFeCTLA4$_{223}$ shared 88.8%, 87.9%, 86.9%, 77.6%, and 77.1% of identity with the CTLA4$_{223}$ proteins of rabbit, human, bovine, mouse, and rat, respectively. PCaCTLA4$_{223}$ and PFeCTLA4$_{223}$ shared the highest identity (97.2%).

At the nucleotide level, nCaCTLA4$_{1856}$ shared 86.7%, 86.7%, 86.3%, 76.1%, and 59.5% identity with the cDNA sequences of human, rabbit, bovine, rat, and mouse CTLA4, respectively. Nucleic acid molecule nFeCTLA4$_{11883}$ shared 88.7%, 86.4%, 86.3%, 77.3% and 57.3% identity with the cDNA sequences of human rabbit, bovine, rat, and mouse CTLA4, respectively. Nucleic acid molecules nCaCTLA4$_{1856}$ and nFeCTL4$_{1883}$ shared the 89.2% identity.

Example 12

This example describes the expression in Pichia of a canine CTLA4 cDNA fragment, nucleotides 168–542 of SEQ ID NO:41, encoding the extracellular domain of the mature canine CTLA4 protein, i.e., amino acid residues 37–161 of SEQ ID NO:42. A 375-nucleotide fragment, denoted herein as nCaCTLA4$_{375}$, was isolated from nCaCTLA4$_{1856}$ by PCR using sense primer 5' GGT ACG TAG GGA TGC ATG TGG CTC AGC 3' denoted herein as SEQ ID:62, with nucleotides 9–27 corresponding to nucleotides 168–186 of SEQ ID NO:41; and antisense primer 5' CCG AAT TCT CAG TCA GAA TCT GGG CAA GGT TC 3', denoted herein as SEQ ID NO:63, with nucleotides 9–32 corresponding to the reverse complement of nucleotides 522–542 of SEQ ID NO:41. To facilitate cloning, an Sna BI site (shown in bold) was added to the sense primer and an Eco RI site (shown in bold) was added to the antisense primer. The PCR fragment was digested with restriction endonucleases Sna BI and Eco RI, gel purified and ligated into pPIC9K plasmid vector, available from Invitrogen, that had been digested by Sna R1 and Eco RI and gel purified to produce recombinant molecule pPIC9K-nCaCTLA4$_{375}$. The insert in the recombinant plasmid was verified by DNA sequencing. After linearization, the plasmid was used to transform Pichia strain GS115, available in kit form from Invitrogen, by electroporation. Colonies containing putative high copy number of the plasmid was selected on plates with G418. Colonies resistant to at least 200 μg/ml of G418 were selected for expression by induction with 0.5% methanol in BMM, available from Invitrogen, according to manufacturer's instructions. Recombinant protein was isolated using a Sepharose Q high-trap column, available from Pharmacia Biotech, Inc., Piscttaway, N.J. The identity of the protein was verified by N-terminal sequencing.

Example 13

This example describes the ability of a recombinant canine CTLA4 protein expressed in Pichia to bind to canine B7-1 or B7-2, expressed on the surface of mouse cells.

Recombinant canine CTLA4 protein, produced in Pichia, was tested for its ability to bind to canine B7 molecules, as follows. Briefly, 1×10$^5$ (per condition) L-pCMV-nCaB7-2$_{1897}$ or LpCMV-nCaB7-1$_{1385}$, produced as described in Example 10, were incubated in phosphate buffered saline (PBS) containing 30% fetal bovine serum (FBS) for about 30 min on ice. The cells were then spun down and treated in one of the following manners:

| Condition | Primary Incubation | Secondary Incubation | Tertiary Incubation |
|---|---|---|---|
| 1 | PBS/5% FBS | PBS/5% FBS | Rabbit anti goat IgG FITC |
| 2 | PBS/5% FBS | Goat anti human CTLA4 | Rabbit anti goat IgG FITC |
| 3 | Canine CTLA4 | Goat anti human CTLA4 | Rabbit anti goat IgG FITC |

Polyclonal rabbit anti goat IgG FITC, available from Southern Biotechnologies, Birmingham, Ala., was used at approximately 10 μg/ml. Polyclonal goat anti human CTLA4, available from R & D systems, was used at approximately 2 μg/ml. Canine CTLA4 expressed in Pichia was used at 60–600 μg/ml All reagents were diluted in PBS/5% FBS.

All incubations were performed in about 100 μl for about 1 hr on ice with 3 washes of PBS/5% FBS in between each incubation. Cells were then analyzed on a flow cytometer as described in Example 9. The results are shown below in Tables 4 and 5.

TABLE 4

Binding of canine CTLA4 expressed in Pichia to canine B7-2 expressed on L cell transfectants.

| Condition | % positive cells |
|---|---|
| 1 | 1 |
| 2 | 1 |
| 3 | 89 |

TABLE 5

Binding of canine CTLA4 expressed in Pichia to canine B7-1 expressed on L cell transfectants.

| Condition | % positive cells |
|---|---|
| 1 | 4 |
| 2 | 2 |
| 3 | 63 |

This experiment shows that recombinant canine CTLA-4 protein produced in Pichia is able to bind to canine B7-2 and B7-1 expressed on the membrane of recombinant L cells.

Example 14

This example describes the production of mouse polyclonal sera to canine B7-2 expressed on LpCMV-nCaB7-$2_{1897}$ and expression in Pichia of soluble canine B7-2.

A. Mouse antibodies specifically reactive with canine B7-2 were produced in mice as follows: Briefly, Balbic mice were immunized with about $10^6$ L-pCMV-nCaB7-$2_{1897}$ recombinant cells, prepared as described in Example 10. The mice were boosted after about 4 weeks with about $1 \times 10^6$ L-pCMV-nCaB7-$2_{1897}$ recombinant cells. Serum isolated from the mice was screened by flow cytometry for positive reactivity on L-pCMW-nCaB7-$2_{1897}$ recombinant cells.

The sera was negative on L-CMV cells (described in Example 9) and on L-pCMV-nCaB7-$1_{1385}$ recombinant cells, prepared as described in Example 10. This 30 suggests that the sera was not cross-reactive with canine B7-1.

B. A 780-nucleotide canine B7-2 cDNA fragment, i.e., nucleotides 70–849 of SEQ ID NO. 16, encoding the mature portion of soluble canine B7-2 protein, i.e., residues 22–280 of SEQ ID NO. 17, was isolated by PCR from nCaB7-$2s_{1795}$ using sense primer 5' GGT ACG TAG GTG CTG CTT CCA TGA AGA G 3', denoted herein as SEQ ID NO:64, with nucleotides 9–28 corresponding to nucleotides 70–89 of SEQ ID NO:16; and antisense primer, CCC CTA GGT TAA AAC TGT GTA GTA CTG TTG TCG CC-3', denoted herein as SEQ ID NO:65, with nucleotides 9–35 corresponding to the reverse complement of nucleotides 823–849 of SEQ ID NO:16. To facilitate cloning, an Sna BI site (shown in bold) was added to the sense primer and an Avr It site (shown in bold) was added to the antisense primer. The PCR fragment was digested with restriction endonucleases Sna Bland Avr II, gel purified and ligated into pPIC9K plasmid vector that had been digested by Sna R1 and Avr II and gel purified to produce recombinant molecule pPIC9K-nCaB7-$2s_{780}$. The insert in the recombinant plasmid was verified by DNA sequencing. After linearization, the plasmid was used to transform GS115 strain of Pichia. Secreted protein in the supernatant from G418 resistant colonies, produced as described in Example 12, specifically reacted in immunoblots and ELISA with polyclonal antibodies produced in mice immunized with canine B7-2 recombinant cell pCMV-nCaB7-$2_{1897}$ produced as described in Example 14.A., above.

While various embodiments of the present invention have been described in detail, it is apparent that modifications and adaptations of those embodiments will occur to those skilled in the art It is to be expressly understood, however, that such modifications and adaptations arc within the scope of the present invention, as set forth in the following claims.

What is claimed is:

1. An isolated nucleic acid molecule selected from the group consisting of:
   (a) a nucleic acid molecule having a nucleic acid sequence that is at least about 95 percent identical over the full length to of a nucleic acid sequence selected from the group consisting of SEQ ID NO:6, SEQ ID NO:9, SEQ ID NO:16, SEQ ID NO:19, SEQ ID NO:25 and SEQ ID NO:28, wherein the isolated nucleic acid molecule encodes a protein that elicits an immune response against a canine protein having the amino acid sequence of SEQ ID NO:7, SEQ ID NO:17 or SEQ ID NO:28 or wherein said encoded protein, in conjunction with engagement of a T cell receptor with a major histocompatability molecule complexed with a peptide, stimulates T cell proliferation; and
   (b) a nucleic acid molecule fully complementary to the nucleic acid molecule of (a).

2. An isolated nucleic acid molecule selected from the group consisting of:
   (a) a nucleic acid molecule having a nucleic acid sequence that is at least about 95% identical over the full length of SEQ ID NO:33, wherein the isolated nucleic acid molecule encodes a protein that elicits an immune response against a protein having the amino acid sequence of SEQ ID NO:34 or wherein said encoded protein, in conjunction with engagement of a T cell receptor with a major histocompatability molecule complexed with a peptide, stimulates T cell proliferation;
   (b) a nucleic acid molecule comprising a nucleic acid sequence encoding a protein that is at least about 95% identical over the full-length of SEQ ID NO:34, wherein said encoded protein elicits an immune response against a protein having the amino acid sequence of SEQ ID NO:34 or wherein said encoded protein, in conjunction with engagement of a T cell receptor with a major histocompatibility molecule complexed with a peptide, stimulates T cell proliferation;
   (c) a nucleic acid molecule comprising the nucleic acid sequence of SEQ ID NO:30; and,
   (d) a nucleic acid molecule fully complementary to the nucleic acid molecule of (a), (b) or (c).

3. The isolated nucleic acid molecule of claim 1, wherein said nucleic acid molecule comprises a nucleic acid sequence selected from the group consisting of:
   (a) SEQ ID NO:6, SEQ ID NO:9, SEQ ID NO:16, SEQ ID NO:19, SEQ ID NO:25, SEQ ID NO:28; and
   (b) a nucleic acid sequence fully complementary to the nucleic acid sequence of (a).

4. The isolated nucleic acid molecule of claim 2, wherein said nucleic acid molecule comprises a nucleic acid sequence is selected from the group consisting of:
   (a) SEQ ID NO:30, SEQ ID NO:33; and
   (b) a nucleic acid sequence fully complementary to the nucleic acid sequence of (a).

5. An isolated nucleic acid molecule selected from the group consisting of:
   (a) a nucleic acid molecule having a nucleic acid sequence encoding a B7-2 protein that is at least about 95% identical over the full length of an amino acid sequence selected from the group consisting of SEQ ID NO:7, SEQ ID NO:17 and SEQ ID NO:26, wherein said encoded B7-2 protein elicits an immune response against a protein having the amino acid sequence of SEQ ID NO:7, SEQ ID NO:1 or SEQ ID NO:28 or wherein said encoded B7-2 protein, in conjunction with engagement of a T cell receptor with a major histocompatibility molecule complexed with a peptide, stimulated T cell proliferation; and
   (b) a nucleic acid molecule fully complimentary to the nucleic acid molecule of (a).

6. The isolated nucleic acid molecule of claim 5, wherein said encoded B7-2 protein has an amino acid sequence selected from the group consisting of SEQ ID NO:7, SEQ ID NO:17 and SEQ ID NO:26.

7. The isolated nucleic acid molecule of claim 2, wherein said nucleic acid molecule comprises a nucleic acid sequence encoding a protein having the amino acid sequence of SEQ ID NO:31 or SEQ ID NO:34.

8. An isolated nucleic acid molecule selected from the group consisting of:
   (a) an isolated nucleic acid molecule consisting of a fragment of SEQ ID NO:6, SEQ ID NO:9, SEQ ID NO:16, SEQ ID NO:19, SEQ ID NO:25 or SEQ ID NO:28, wherein said fragment is greater than about 50 nucleotides of SEQ ID NO:6, SEQ ID NO:9, SEQ ID NO:16, SEQ ID NO:19, SEQ ID NO:25 or SEQ ID NO:28; and
   (b) a nucleic acid molecule fully complementary to the nucleic acid molecule of (a).

9. A composition comprising the isolated nucleic acid molecule as specified in any one of claims 1–8 and an excipient.

10. A method to produce a canine or feline B7-2 protein, said method comprising culturing a cell capable of expressing said B7-2 protein, said B7-2 protein being encoded by a nucleic acid molecule having a nucleic acid sequence that is at least about 95% identical over the full length of a nucleic acid sequence selected from the group consisting of SEQ ID NO:6, SEQ ID NO:9, SEQ ID NO:16, SEQ ID NO:19, SEQ ID NO:25 and SEQ ID NO:28, wherein said encoded protein elicits an immune response against a protein having the amino acid sequence of SEQ ID NO:7, SEQ ID NO:17 or SEQ ID NO:28 or wherein said encoded protein, in conjunction with engagement of a T cell receptor with a major histocompatability molecule complexed with a peptide, stimulates T-cell proliferation and recovering said canine or feline B7-2 protein.

11. The method of claim 10, wherein said nucleic acid molecule encodes a B7-2 protein that is at least about 95% identical over the full length of an amino acid sequence selected from the group consisting of SEQ ID NO:7, SEQ ID NO:17 and SEQ ID NO:26.

12. The method of claim 10, wherein said nucleic acid molecule comprises a nucleic acid sequence selected from the group consisting of SEQ ID NO:6, SEQ ID NO:9, SEQ ID NO:16, SEQ ID NO:19, SEQ ID NO:25 and SEQ ID NO:28.

13. The method of claim 10, wherein said nucleic acid molecule comprises a nucleic acid sequence that encodes a protein having an amino acid sequence selected from the group consisting of SEQ ID NO:7, SEQ ID NO:17 and SEQ ID NO:26.

14. A method to produce a canine or feline B7-2 protein said method comprising:

(a) culturing a cell comprising the isolated nucleic acid molecule from (a), (b) or (c) of claim 2, wherein said cell is capable of expressing said B7-2 protein; and (b) recovering said canine or feline B7-2 protein.

15. A method to produce a canine or feline B7-2 peptide, said method comprising culturing a cell capable of expressing said B7-2 peptide, said B7-2 peptide being encoded by a nucleic acid molecule consisting of a fragment of SEQ ID NO:6, SEQ ID NO:9, SEQ ID NO:16, SEQ ID NO:19, SEQ ID NO:25 or SEQ ID NO:28, wherein said fragment is greater than about 50 nucleotides of SEQ ID NO:6, SEQ ID NO:9, SEQ ID NO:16, SEQ ID NO:19, SEQ ID NO:25 or SEQ ID NO:28; and recovering said canine or feline B7-2 protein.

16. A recombinant molecule comprising a nucleic acid sequence as set forth in any one of claims 1–8 operatively linked to a transcription control sequence.

17. A recombinant virus comprising a nucleic acid molecule as set forth in any one of claims 1–8.

18. A recombinant cell comprising a nucleic acid molecule as set forth in any one of claims 1–8.

* * * * *

UNITED STATES PATENT AND TRADEMARK OFFICE
CERTIFICATE OF CORRECTION

PATENT NO. : 6,852,847 B1  
APPLICATION NO. : 09/646561  
DATED : February 8, 2005  
INVENTOR(S) : Gek-Kee Sim and Shumin Yang It is certified that error appears in the above-identified patent and that said Letters Patent is hereby corrected as shown below:

On the title page, item (75), please remove Inventor: Karen S. Sellins

Column 125, line 22, please replace "length to of a nucleic acid sequence selected from the" with --length of a nucleic acid sequence selected from the--.

Column 125, line 27, please replace "against a canine protein having the amino acid" with --against a protein having the amino acid--.

Column 126, line 19, please replace "sequence is selected from the group consisting of:" with --sequence selected from the group consisting of:--.

Column 126, line 37, please replace "stimulated T cell proliferation; and" with --stimulates T cell proliferation; and--.

Signed and Sealed this

Twenty-ninth Day of July, 2008

JON W. DUDAS  
*Director of the United States Patent and Trademark Office*

SEQUENCE LISTING

```
<160> NUMBER OF SEQ ID NOS: 65

<210> SEQ ID NO 1
<211> LENGTH: 2830
<212> TYPE: DNA
<213> ORGANISM: Canis familiaris
<220> FEATURE:
<221> NAME/KEY: CDS
<222> LOCATION: (337)..(1248)

<400> SEQUENCE: 1
gtgctttgtc ctagccacac tctctgaggt ggctgacaaa aagggacagc agaaccagct      60
tcctcaagtt atacataaca tctacacatc ccctgctttg acttaaatac tgctggtaat     120
gaacatcagc tagatcttcc agcgagtaaa aggaagttgg aaagggggatt gcctctggta   180 tatcacccaa agaaaagctg agcaacttgc cattattttg gagacagcaa gaaaggaaca    240
tctcagaact ggggcctcat cctttgacgt tttgttttgt tttgttctaa cacaagaaaa     300
aaaaaaaaga ggagttatcc ttcagcagca gaagcc atg gat tac aca gcg aag      354
                                         Met Asp Tyr Thr Ala Lys
```

-continued

|  |  |  |  |  |  | 1 |  |  |  | 5 |  |  |  |  |  |
|---|---|---|---|---|---|---|---|---|---|---|---|---|---|---|---|
| tgg | aga | aca | cca | cca | ctc | aaa | cac | cca | tat | ctc | aag | gtc | tct | cag | ctc | 402 |
| Trp | Arg | Thr | Pro | Pro | Leu | Lys | His | Pro | Tyr | Leu | Lys | Val | Ser | Gln | Leu |
|  |  |  | 10 |  |  |  | 15 |  |  |  |  | 20 |  |  |  |

```
tgg aca cca cca ctc aaa cac cca tat ctc aag gtc tct cag ctc      402
Trp Arg Thr Pro Pro Leu Lys His Pro Tyr Leu Lys Val Ser Gln Leu
             10              15                  20 ttg gtg cta gct agt ctc ttt tac ttc tgt tca ggc atc atc cag gtg  450
Leu Val Leu Ala Ser Leu Phe Tyr Phe Cys Ser Gly Ile Ile Gln Val
         25              30              35 aac aag aca gtg aaa gaa gta gca gta ctg tcc tgt gat tac aac att  498
Asn Lys Thr Val Lys Glu Val Ala Val Leu Ser Cys Asp Tyr Asn Ile
     40              45              50 tcc act aca gaa ctg atg aaa gtt cga atc tat tgg caa aag gat gat  546
Ser Thr Thr Glu Leu Met Lys Val Arg Ile Tyr Trp Gln Lys Asp Asp
 55              60              65                      70 gaa gtg gtg ctg gct gtc aca tct gga caa acg aaa gtg tgg tcc aag  594
Glu Val Val Leu Ala Val Thr Ser Gly Gln Thr Lys Val Trp Ser Lys
                     75              80              85 tat gag aat cgc acc ttt gct gac ttc acc aat aac ctc tcc atc gtg  642
Tyr Glu Asn Arg Thr Phe Ala Asp Phe Thr Asn Asn Leu Ser Ile Val
                 90              95                  100 att atg gct ctg cgc ctg tca gac aat ggc aaa tac acc tgt atc gtt  690
Ile Met Ala Leu Arg Leu Ser Asp Asn Gly Lys Tyr Thr Cys Ile Val
             105             110             115 caa aag act gaa aaa agg tct tac aaa gtg aaa cac atg act tcg gtg  738
Gln Lys Thr Glu Lys Arg Ser Tyr Lys Val Lys His Met Thr Ser Val
         120             125             130 atg tta ttg gtc aga gct gac ttc cct gtc cct agt ata act gac ctt  786
Met Leu Leu Val Arg Ala Asp Phe Pro Val Pro Ser Ile Thr Asp Leu
135             140             145                 150 gga aat cca tcc cat gac atc aaa agg ata atg tgt tca acc tct gga  834
Gly Asn Pro Ser His Asp Ile Lys Arg Ile Met Cys Ser Thr Ser Gly
                 155             160                 165 ggt ttt cca aag cct cac ctc tcc tgg tgg gaa aat gaa gaa gaa ttg  882
Gly Phe Pro Lys Pro His Leu Ser Trp Trp Glu Asn Glu Glu Glu Leu
             170             175                 180 aat gct gcc aac aca aca gtt tcc caa gac ccg gac act gag ttg tac  930
Asn Ala Ala Asn Thr Thr Val Ser Gln Asp Pro Asp Thr Glu Leu Tyr
                     185             190             195 act att agt agt gaa ctg gat ttc aat ata aca agc aac cat agc ttt  978
Thr Ile Ser Ser Glu Leu Asp Phe Asn Ile Thr Ser Asn His Ser Phe
200                 205                 210 gtg tgt ctt gtc aag tat gga gac tta aca gta tca cag atc ttc aac  1026
Val Cys Leu Val Lys Tyr Gly Asp Leu Thr Val Ser Gln Ile Phe Asn
215             220                 225                 230 tgg caa aaa tca gtc gag cca cac cct ccc aat aac cag caa cag ctc  1074
Trp Gln Lys Ser Val Glu Pro His Pro Pro Asn Asn Gln Gln Gln Leu
                 235                 240                 245 tgg gtc atc ctg atc tta gta gta agt ggt gtg att gct gtg atc act  1122
Trp Val Ile Leu Ile Leu Val Val Ser Gly Val Ile Ala Val Ile Thr
             250                 255                 260 gcc att aca gga ggc tgc cta gcc cac aga tct gct gca aga tgg aga  1170
Ala Ile Thr Gly Gly Cys Leu Ala His Arg Ser Ala Ala Arg Trp Arg
         265                 270                 275 cag aga aat agg aac aaa gag gac atg gac ctg gaa aag atg tcc cct  1218
Gln Arg Asn Arg Asn Lys Glu Asp Met Asp Leu Glu Lys Met Ser Pro
     280                 285                 290 ata aac ata gga tct gcc caa gca tct gta tgagcagaac atctggaggt    1268
Ile Asn Ile Gly Ser Ala Gln Ala Ser Val
295                 300 cccacctcca tcttagattg acctcatctt tgaatttcct cagatggcca ggattatccc  1328
```

-continued

```
accttgcact tcatgcatct gttctctagg agcctgttca tttcagtggc cctgcagaaa   1388
gtgaccagag gaatatggtg gggacataag tagctctctg gtagccttgg tcaaagaatt   1448
gttcaggcct gggaagagac attcggaaaa tacttgtctc attaatgaca aggacatcaa   1508
ggcctagggg gtgacctgaa tgataaaggt ctgagctaga acccagattt cctgtctcgg   1568
gtgctctttt ccatcagtag tccggctctg tgctattaac tggtgtgtac aggtgtacac   1628
accagtcaaa atgcttctgg aaaagagta tgtccaatgt caggtcaact tcagagactt    1688
catctgatgc aacactagaa ggttttgtgt tgctgtcaaa agcaatctga tgctaatgtg   1748
tggtagtatg atggtatata taccaatatg agaatgatgg aaaaattact ggggtttact   1808
cagtatctca tctttcattg tgttctcctc tgttgctttc ccacttctcc atcaggttct   1868
ggagaaagta gatctatcca aaactaatat ctgctgacat gtaagatgaa tgacttatat   1928
acctcaaagc gatagtcacg ttggagaggg ataggttggt ttagagagtc acatcctact   1988
ggttcatatt ggactgataa tctccttaat ggctttatgc tagtttaaac tcatttataa   2048
aacatgagaa agttctcatt taaaatgaga taggttttaa ttgtatatta ctaaacagat   2108
attactaaac agtagctgtc cttagaattt gattgaggta atgaaaatag cattccatag   2168
ggtttcccta gattcctcaa gttgctcttc ctccttggta tttctgatcc ttctgacatc   2228
agcagagaat taaaaataaa gaagtggcca actgccgttc ctgtgtcact tactcatgat   2288
tcctttctct gaagttgtct tccataactc agtggacctg gaggtagacc tgactggagg   2348
aatcagacat tctcatttga aaatttgacg ttggacagca agttggccaa gtttctcaca   2408
tgtagctggg tttacaatgt ttaattttgg cagctatcaa gggaccagat tatgctatat   2468
agtctaagga gcagaagtac agtttttaaat ggttgccctc agaacaaaat cactgaaaga   2528
aataaaagtt ggagactgac ctgaactcaa agcaaagaaa caaaaaaaat gggaactgct   2588
gcatttaatt aaaattaata atccttagac atgctcaaaa ggagacctca agaagtaatc   2648
acaaaatagg acacatctag gagacagctt atttatactt aaaataaatt atattacatt   2708
acttattaca tttgataaat gtgttggtac tattttccaa agaattatac ttttattgat   2768
atttttgtga tatgaataaa attatttta aaaccaaaaa aaaaaaaaa aaaaaaaaa     2828 aa                                                                  2830
```

<210> SEQ ID NO 2
<211> LENGTH: 304
<212> TYPE: PRT
<213> ORGANISM: Canis familiaris

<400> SEQUENCE: 2

```
Met Asp Tyr Thr Ala Lys Trp Arg Thr Pro Pro Leu Lys His Pro Tyr
 1               5                  10                  15

Leu Lys Val Ser Gln Leu Leu Val Leu Ala Ser Leu Phe Tyr Phe Cys
            20                  25                  30

Ser Gly Ile Ile Gln Val Asn Lys Thr Val Lys Glu Val Ala Val Leu
        35                  40                  45

Ser Cys Asp Tyr Asn Ile Ser Thr Thr Glu Leu Met Lys Val Arg Ile
    50                  55                  60

Tyr Trp Gln Lys Asp Asp Glu Val Val Leu Ala Val Thr Ser Gly Gln
65                  70                  75                  80

Thr Lys Val Trp Ser Lys Tyr Glu Asn Arg Thr Phe Ala Asp Phe Thr
                85                  90                  95
```

-continued

Asn Asn Leu Ser Ile Val Ile Met Ala Leu Arg Leu Ser Asp Asn Gly
            100                 105                 110

Lys Tyr Thr Cys Ile Val Gln Lys Thr Glu Lys Arg Ser Tyr Lys Val
        115                 120                 125

Lys His Met Thr Ser Val Met Leu Leu Val Arg Ala Asp Phe Pro Val
    130                 135                 140

Pro Ser Ile Thr Asp Leu Gly Asn Pro Ser His Asp Ile Lys Arg Ile
145                 150                 155                 160

Met Cys Ser Thr Ser Gly Gly Phe Pro Lys Pro His Leu Ser Trp Trp
                165                 170                 175

Glu Asn Glu Glu Leu Asn Ala Ala Asn Thr Thr Val Ser Gln Asp
            180                 185                 190

Pro Asp Thr Glu Leu Tyr Thr Ile Ser Ser Glu Leu Asp Phe Asn Ile
            195                 200                 205

Thr Ser Asn His Ser Phe Val Cys Leu Val Lys Tyr Gly Asp Leu Thr
    210                 215                 220

Val Ser Gln Ile Phe Asn Trp Gln Lys Ser Val Glu Pro His Pro Pro
225                 230                 235                 240

Asn Asn Gln Gln Gln Leu Trp Val Ile Leu Ile Leu Val Val Ser Gly
                245                 250                 255

Val Ile Ala Val Ile Thr Ala Ile Thr Gly Gly Cys Leu Ala His Arg
                260                 265                 270

Ser Ala Ala Arg Trp Arg Gln Arg Asn Arg Asn Lys Glu Asp Met Asp
            275                 280                 285

Leu Glu Lys Met Ser Pro Ile Asn Ile Gly Ser Ala Gln Ala Ser Val
            290                 295                 300

<210> SEQ ID NO 3
<211> LENGTH: 2830
<212> TYPE: DNA
<213> ORGANISM: Canis familiaris

<400> SEQUENCE: 3
tttttttttt tttttttttt ttttttttggt tttaaaaata attttattca tatcacaaaa    60
atatcaataa aagtataatt ctttggaaaa tagtaccaac acatttatca aatgtaataa   120
gtaatgtaat ataatttatt ttaagtataa ataagctgtc tcctagatgt gtcctatttt   180
gtgattactt cttgaggtct ccttttgagc atgtctaagg attattaatt ttaattaaat   240
gcagcagttc ccatttttt tgtttctttg ctttgagttc aggtcagtct ccaactttta   300
tttctttcag tgattttgtt ctgagggcaa ccatttaaaa ctgtacttct gctccttaga   360
ctatatagca taatctggtc ccttgatagc tgccaaaatt aaacattgta aacccagcta   420
catgtgagaa acttggccaa cttgctgtcc aacgtcaaat tttcaaatga aatgtctga    480 ttcctccagt caggtctacc tccaggtcca ctgagttatg gaagacaact tcagagaaag   540
gaatcatgag taagtgacac aggaacggca gttggccact tctttatttt taattctctg   600
ctgatgtcag aaggatcaga ataccaagg aggaagagca acttgaggaa tctagggaaa    660
ccctatggaa tgctattttc attaccctcaa tcaaattcta aggacagcta ctgtttagta   720
atatctgttt agtaatatac aattaaaacc tatctcattt taatgagaa ctttctcatg    780 ttttataaat gagtttaaac tagcataaag ccattaagga gattatcagt ccaatatgaa   840
ccagtaggat gtgactctct aaaccaacct atccctctcc aacgtgacta tcgctttgag   900
gtatataagt cattcatctt acatgtcagc agatattagt tttggataga tctactttct   960

| | |
|---|---|
| ccagaacctg atggagaagt gggaaagcaa cagaggagaa cacaatgaaa gatgagatac | 1020 |
| tgagtaaacc ccagtaattt ttccatcatt ctcatattgg tatatatacc atcatactac | 1080 |
| cacacattag catcgattg cttttgacag caacacaaaa ccttctagtg ttgcatcaga | 1140 |
| tgaagtctct gaagttgacc tgacattgga catactcttt ttccagaagc attttgactg | 1200 |
| gtgtgtacac ctgtcacac cagtaatag cacagagccg gactactgat ggaaaagagc | 1260 |
| acccgagaca ggaaatctgg gttctagctc agacctttat cattcaggtc accccctagg | 1320 |
| ccttgatgtc cttgtcatta atgagacaag tattttccga atgtctcttc ccaggcctga | 1380 |
| acaattcttt gaccaaggct accagagagc tactatgtc cccaccatat tcctctggtc | 1440 |
| actttctgca gggccactga aatgaacagg ctcctagaga acagatgcat gaagtgcaag | 1500 |
| gtgggataat cctggccatc tgaggaaatt caaagatgag gtcaatctaa gatggaggtg | 1560 |
| ggacctccag atgttctgct catacagatg cttgggcaga tcctatgttt ataggggaca | 1620 |
| tcttttccag gtccatgtcc tctttgttcc tatttctctg tctccatctt gcagcagatc | 1680 |
| tgtgggctag gcagcctcct gtaatggcag tgatcacagc aatcacacca cttactacta | 1740 |
| agatcaggat gacccagagc tgttgctggt tattgggagg gtgtggctcg actgatttt | 1800 |
| gccagttgaa gatctgtgat actgttaagt ctccatactt gacaagacac acaaagctat | 1860 |
| ggttgcttgt tatattgaaa tccagttcac tactaatagt gtacaactca gtgtccgggt | 1920 |
| cttgggaaac tgttgtgttg gcagcattca attcttcttc attttcccac caggagaggt | 1980 |
| gaggcttttgg aaaacctcca gaggttgaac acattatcct tttgatgtca tgggatggat | 2040 |
| ttccaaggtc agttatacta gggacaggga agtcagctct gaccaataac atcaccgaag | 2100 |
| tcatgtgttt cactttgtaa gacctttttt cagtcttttg aacgatacag gtgtatttgc | 2160 |
| cattgtctga caggcgcaga gccataatca cgatggagag gttattggtg aagtcagcaa | 2220 |
| aggtgcgatt ctcatacttg gaccacactt tcgtttgtcc agatgtgaca gccagcacca | 2280 |
| cttcatcatc cttttgccaa tagattcgaa cttttcatcag ttctgtagtg gaaatgttgt | 2340 |
| aatcacagga cagtactgct acttctttca ctgtcttgtt cacctggatg atgcctgaac | 2400 |
| agaagtaaaa gagactagct agcaccaaga gctgagagac cttgagatat gggtgtttga | 2460 |
| gtggtggtgt tctccacttc gctgtgtaat ccatggcttc tgctgctgaa ggataactcc | 2520 |
| tcttttttt ttttcttgtg ttagaacaaa acaaaacaaa acgtcaaagg atgaggcccc | 2580 |
| agttctgaga tgttccttc ttgctgtctc caaaataatg gcaagttgct cagcttttct | 2640 |
| ttgggtgata taccagaggc aatccccttt ccaacttcct tttactcgct ggaagatcta | 2700 |
| gctgatgttc attaccagca gtatttaagt caaagcaggg gatgtgtaga tgttatgtat | 2760 |
| aacttgagga agctggttct gctgtccctt tttgtcagcc acctcagaga gtgtggctag | 2820 |
| gacaaagcac | 2830 |

<210> SEQ ID NO 4
<211> LENGTH: 912
<212> TYPE: DNA
<213> ORGANISM: Canis familiaris

<400> SEQUENCE: 4

| | |
|---|---|
| atggattaca cagcgaagtg gagaacacca ccactcaaac acccatatct caaggtctct | 60 |
| cagctcttgg tgctagctag tctctttttac ttctgttcag gcatcatcca ggtgaacaag | 120 |
| acagtgaaag aagtagcagt actgtcctgt gattacaaca tttccactac agaactgatg | 180 |
| aaagttcgaa tctattggca aaaggatgat gaagtggtgc tggctgtcac atctggacaa | 240 |

```
acgaaagtgt ggtccaagta tgagaatcgc acctttgctg acttcaccaa taacctctcc    300
atcgtgatta tggctctgcg cctgtcagac aatggcaaat acacctgtat cgttcaaaag    360
actgaaaaaa ggtcttacaa agtgaaacac atgacttcgg tgatgttatt ggtcagagct    420
gacttccctg tccctagtat aactgacctt ggaaatccat cccatgacat caaaaggata    480
atgtgttcaa cctctggagg ttttccaaag cctcacctct cctggtggga aaatgaagaa    540
gaattgaatg ctgccaacac aacagtttcc caagacccgg acactgagtt gtacactatt    600
agtagtgaac tggatttcaa tataacaagc aaccatagct ttgtgtgtct tgtcaagtat    660
ggagacttaa cagtatcaca gatcttcaac tggcaaaaat cagtcgagcc acaccctccc    720
aataaccagc aacagctctg ggtcatcctg atcttagtag taagtggtgt gattgctgtg    780
atcactgcca ttacaggagg ctgcctagcc cacagatctg ctgcaagatg gagacagaga    840
aataggaaca agaggacat ggacctggaa aagatgtccc ctataaacat aggatctgcc    900
caagcatctg ta                                                        912

<210> SEQ ID NO 5
<211> LENGTH: 912
<212> TYPE: DNA
<213> ORGANISM: Canis familiaris

<400> SEQUENCE: 5
tacagatgct tgggcagatc ctatgtttat aggggacatc ttttccaggt ccatgtcctc     60
tttgttccta tttctctgtc tccatcttgc agcagatctg tgggctaggc agcctcctgt    120
aatggcagtg atcacagcaa tcacaccact tactactaag atcaggatga cccagagctg    180
ttgctggtta ttgggagggt gtggctcgac tgattttgc cagttgaaga tctgtgatac     240
tgttaagtct ccatacttga caagacacac aaagctatgg ttgcttgtta tattgaaatc    300
cagttcacta ctaatagtgt acaactcagt gtccgggtct tgggaaactg ttgtgttggc    360
agcattcaat tcttcttcat tttcccacca ggagaggtga ggctttggaa aacctccaga    420
ggttgaacac attatccttt tgatgtcatg ggatggattt ccaaggtcag ttatactagg    480
gacagggaag tcagctctga ccaataacat caccgaagtc atgtgtttca ctttgtaaga    540 cctttttca gtcttttgaa cgatacaggt gtatttgcca ttgtctgaca ggcgcagagc    600
cataatcacg atggagaggt tattggtgaa gtcagcaaag gtgcgattct catacttgga    660
ccacactttc gttgtccag atgtgacagc cagcaccact tcatcatcct tttgccaata    720
gattcgaact tcatcagtt ctgtagtgga aatgttgtaa tcacaggaca gtactgctac    780
ttctttcact gtcttgttca cctggatgat gcctgaacag aagtaaaaga gactagctag    840
caccaagagc tgagagacct tgagatatgg gtgtttgagt ggtggtgttc tccacttcgc    900
tgtgtaatcc at                                                        912

<210> SEQ ID NO 6
<211> LENGTH: 1897
<212> TYPE: DNA
<213> ORGANISM: Canis familiaris
<220> FEATURE:
<221> NAME/KEY: CDS
<222> LOCATION: (6)..(992)

<400> SEQUENCE: 6 ccaag atg tat ctc aga tgc act atg gaa ctg aat aac att ctc ttt gtg      50
      Met Tyr Leu Arg Cys Thr Met Glu Leu Asn Asn Ile Leu Phe Val
        1               5                  10                  15
```

-continued

```
atg acc ctc ctg ctc tat ggt gct gct tcc atg aag agt caa gca tat        98
Met Thr Leu Leu Leu Tyr Gly Ala Ala Ser Met Lys Ser Gln Ala Tyr
             20                  25                  30 ttc aac aag act gga gaa ctg cca tgc cat ttt aca aat tct caa aac       146
Phe Asn Lys Thr Gly Glu Leu Pro Cys His Phe Thr Asn Ser Gln Asn
         35                  40                  45 ata agc ctg gat gag ttg gta gtg ttt tgg cag gac cag gat aag ctg       194
Ile Ser Leu Asp Glu Leu Val Val Phe Trp Gln Asp Gln Asp Lys Leu
             50                  55                  60 gtt ctg tac gag cta tac aga ggc aaa gag aac cct caa aat gtt cat       242
Val Leu Tyr Glu Leu Tyr Arg Gly Lys Glu Asn Pro Gln Asn Val His
 65                  70                  75 cgc aag tat aag ggc cgc aca agc ttt gac aaa gac aat tgg acc ctg       290
Arg Lys Tyr Lys Gly Arg Thr Ser Phe Asp Lys Asp Asn Trp Thr Leu
 80                  85                  90                  95 aga ctc cat aat att cag atc aag gac aag ggc ttg tat caa tgt ttc       338
Arg Leu His Asn Ile Gln Ile Lys Asp Lys Gly Leu Tyr Gln Cys Phe
                 100                 105                 110 gtt cat cat aaa ggg ccc aaa gga ctc gtt ccc atg cac cag atg aat       386
Val His His Lys Gly Pro Lys Gly Leu Val Pro Met His Gln Met Asn
             115                 120                 125 tct gac cta tca gtg ctt gct aac ttc agt caa cct gaa ata atg gta       434
Ser Asp Leu Ser Val Leu Ala Asn Phe Ser Gln Pro Glu Ile Met Val
         130                 135                 140 act tct aat aga aca gaa aat tct ggc atc ata aat ttg acc tgc tca       482
Thr Ser Asn Arg Thr Glu Asn Ser Gly Ile Ile Asn Leu Thr Cys Ser
     145                 150                 155 tcc ata caa ggt tac cca gaa ccc aag gag atg tat ttt ttg gta aaa       530
Ser Ile Gln Gly Tyr Pro Glu Pro Lys Glu Met Tyr Phe Leu Val Lys
 160                 165                 170                 175 acc gag aat tca agt act aag tat gat act gtc atg aag aaa tct caa       578
Thr Glu Asn Ser Ser Thr Lys Tyr Asp Thr Val Met Lys Lys Ser Gln
                 180                 185                 190 aat aat gtc aca gaa ctc tac aac gtt tct atc agc ttg tcc ttc tca       626
Asn Asn Val Thr Glu Leu Tyr Asn Val Ser Ile Ser Leu Ser Phe Ser
             195                 200                 205 gtc cct gaa gca agc aat gtg agc atc ttc tgt gtc ctg caa ctt gag       674
Val Pro Glu Ala Ser Asn Val Ser Ile Phe Cys Val Leu Gln Leu Glu
         210                 215                 220 tca atg aag ctt ccc tcc cta cct tat aat ata gat gca cat acg aaa       722
Ser Met Lys Leu Pro Ser Leu Pro Tyr Asn Ile Asp Ala His Thr Lys
     225                 230                 235 ccc acc cct gat gga gac cac atc ctc tgg att gcg gct ctg ctt gta       770
Pro Thr Pro Asp Gly Asp His Ile Leu Trp Ile Ala Ala Leu Leu Val
240                 245                 250                 255 atg ttg gtc att ttg tgt ggg atg gtg ttc ttt cta aca cta agg aaa       818
Met Leu Val Ile Leu Cys Gly Met Val Phe Phe Leu Thr Leu Arg Lys
                 260                 265                 270 agg aag aag aag cag cct ggc ccc tct cat gaa tgt gaa acc aac aaa       866
Arg Lys Lys Lys Gln Pro Gly Pro Ser His Glu Cys Glu Thr Asn Lys
             275                 280                 285 gtg gag aga aaa gaa agt gag cag acc aag gaa aga gta cgg tac cat       914
Val Glu Arg Lys Glu Ser Glu Gln Thr Lys Glu Arg Val Arg Tyr His
         290                 295                 300 gaa acg gaa aga tct gat gaa gcc cag tgt gtt aac att tcg aag aca       962
Glu Thr Glu Arg Ser Asp Glu Ala Gln Cys Val Asn Ile Ser Lys Thr
     305                 310                 315 gct tca ggc gac aac agt act aca cag ttt taattaaaga gtaaagtcca        1012
Ala Ser Gly Asp Asn Ser Thr Thr Gln Phe
```

```
                                              -continued 320              325 tccattgttt atatgccttc cctttcaaat tttggcttgc cttttctcg tccattaata   1072 ttattattgc cactaataat aagaggcttt ccagggctcc ctctaaatga gagagcctcc   1132
ctataatgcc agttctgctc cctacaccag gagcagattt taactgcttc ttttcatctc   1192
agagcacact tgtgggccat gctcacctga ctggctcctg gctcaggaat aatgtttaag   1252
actaacacct cctgtttcag attcagcctt cttttcttaa ttttatacat tgtgttttat   1312
gtagaactcc caattactgg actaatggct tttatctatg cttaattcta agatagtgcc   1372
tcattccatc ttgtatattt gtgactacct ctgcagtctg ggtgggagtt ttgtatgtta   1432
tggctttata gtgttgcttt aatattttga gacataaaga gatgtgtact ataataatgt   1492
aattactatg ccctgagaaa attctaccca ctgctgagga gctcttgctc ctctgtgagg   1552
gtcagtacga aaatggtggc ttggtgtgct gacaacaatg agcagaccaa ctcaaaattt   1612
ggaagattag gaatgatgga gatagaacca gctctgagtc ctggagccac ttctatctgg   1672
gctgctgcta atctgaggaa gatccacctg cctaacaagc tatggataag ccttagcagg   1732
gagctctttg tgaagcagga aagcactatg cactgtgaac cctacttctc ttcttgaaaa   1792
aaatggctga gatgatggct cagggcaact gttcaagagc caactgagag atcacaatac   1852
ttaaaagaga aaaagaaaa aagaaaaaaa aaaaaaaaa aaaaa                    1897
```

<210> SEQ ID NO 7
<211> LENGTH: 329
<212> TYPE: PRT
<213> ORGANISM: Canis familiaris

<400> SEQUENCE: 7

```
Met Tyr Leu Arg Cys Thr Met Glu Leu Asn Asn Ile Leu Phe Val Met
  1               5                  10                  15

Thr Leu Leu Tyr Gly Ala Ala Ser Met Lys Ser Gln Ala Tyr Phe
             20                  25                  30

Asn Lys Thr Gly Glu Leu Pro Cys His Phe Thr Asn Ser Gln Asn Ile
         35                  40                  45

Ser Leu Asp Glu Leu Val Val Phe Trp Gln Asp Gln Asp Lys Leu Val
     50                  55                  60

Leu Tyr Glu Leu Tyr Arg Gly Lys Glu Asn Pro Gln Asn Val His Arg
 65                  70                  75                  80

Lys Tyr Lys Gly Arg Thr Ser Phe Asp Lys Asp Asn Trp Thr Leu Arg
                 85                  90                  95

Leu His Asn Ile Gln Ile Lys Asp Lys Gly Leu Tyr Gln Cys Phe Val
            100                 105                 110

His His Lys Gly Pro Lys Gly Leu Val Pro Met His Gln Met Asn Ser
        115                 120                 125

Asp Leu Ser Val Leu Ala Asn Phe Ser Gln Pro Glu Ile Met Val Thr
    130                 135                 140

Ser Asn Arg Thr Glu Asn Ser Gly Ile Ile Asn Leu Thr Cys Ser Ser
145                 150                 155                 160

Ile Gln Gly Tyr Pro Glu Pro Lys Glu Met Tyr Phe Leu Val Lys Thr
                165                 170                 175

Glu Asn Ser Ser Thr Lys Tyr Asp Thr Val Met Lys Lys Ser Gln Asn
            180                 185                 190

Asn Val Thr Glu Leu Tyr Asn Val Ser Ile Ser Leu Ser Phe Ser Val
        195                 200                 205
```

```
Pro Glu Ala Ser Asn Val Ser Ile Phe Cys Val Leu Gln Leu Glu Ser
    210                 215                 220
Met Lys Leu Pro Ser Leu Pro Tyr Asn Ile Asp Ala His Thr Lys Pro
225                 230                 235                 240
Thr Pro Asp Gly Asp His Ile Leu Trp Ile Ala Ala Leu Leu Val Met
                245                 250                 255
Leu Val Ile Leu Cys Gly Met Val Phe Phe Leu Thr Leu Arg Lys Arg
                260                 265                 270
Lys Lys Lys Gln Pro Gly Pro Ser His Glu Cys Glu Thr Asn Lys Val
            275                 280                 285
Glu Arg Lys Glu Ser Glu Gln Thr Lys Glu Arg Val Arg Tyr His Glu
    290                 295                 300
Thr Glu Arg Ser Asp Glu Ala Gln Cys Val Asn Ile Ser Lys Thr Ala
305                 310                 315                 320
Ser Gly Asp Asn Ser Thr Thr Gln Phe
                325
```

<210> SEQ ID NO 8
<211> LENGTH: 1897
<212> TYPE: DNA
<213> ORGANISM: Canis familiaris

<400> SEQUENCE: 8

```
tttttttttt tttttttttt ttctttttc tttttctct tttaagtatt gtgatctctc    60
agttggctct tgaacagttg ccctgagcca tcatctcagc cattttttc aagaagagaa   120
gtagggttca cagtgcatag tgctttcctg cttcacaaag agctccctgc taaggcttat   180
ccatagcttg ttaggcaggt ggatcttcct cagattagca gcagcccaga tagaagtggc   240
tccaggactc agagctggtt ctatctccat cattcctaat cttccaaatt ttgagttggt   300
ctgctcattg ttgtcagcac accaagccac cattttcgta ctgaccctca cagaggagca   360
agagctcctc agcagtgggt agaatttct cagggcatag taattacatt attatagtac   420
acatctcttt atgtctcaaa atattaaagc aacactataa agccataaca tacaaaactc   480
ccacccagac tgcagaggta gtcacaaata tacaagatgg aatgaggcac tatcttagaa   540
ttaagcatag ataaaagcca ttagtccagt aattgggagt tctacataaa acacaatgta   600
taaaattaag aaaagaaggc tgaatctgaa acaggaggtg ttagtcttaa acattattcc   660
tgagccagga gccagtcagg tgagcatggc ccacaagtgt gctctgagat gaaaagaagc   720
agttaaaatc tgctcctggt gtagggagca gaactggcat tataggaggg ctctctcatt   780
tagagggagc cctggaaagc ctcttattat tagtggcaat aataatatta atggacgaga   840
aaaaggcaag ccaaaatttg aaagggaagg catataaaca atggatggac tttactcttt   900
aattaaaact gtgtagtact gttgtcgcct gaagctgtct tcgaaatgtt aacacactgg   960
gcttcatcag atctttccgt ttcatggtac cgtactcttt ccttggtctg ctcactttct  1020
tttctctcca ctttgttggt ttcacattca tgagagggc caggctgctt cttcttcctt  1080
ttccttagtg ttagaaagaa caccatccca cacaaaatga ccaacattac aagcagagcc  1140
gcaatccaga ggatgtggtc tccatcaggg gtgggtttcg tatgtgcatc tatattataa  1200
ggtagggagg gaagcttcat tgactcaagt tgcaggacac agaagatgct cacattgctt  1260
gcttcaggga ctgagaagga caagctgata gaaacgttgt agagttctgt gacattattt  1320
tgagatttct tcatgacagt atcatactta gtacttgaat tctcggtttt taccaaaaaa  1380
tacatctcct tgggttctgg gtaaccttgt atggatgagc aggtcaaatt tatgatgcca  1440
```

```
gaattttctg ttctattaga agttaccatt atttcaggtt gactgaagtt agcaagcact    1500
gataggtcag aattcatctg gtgcatggga acgagtcctt tgggcccttt atgatgaacg    1560
aaacattgat acaagcccct gtccttgatc tgaatattat ggagtctcag ggtccaattg    1620
tctttgtcaa agcttgtgcg gcccttatac ttgcgatgaa cattttgagg gttctctttg    1680
cctctgtata gctcgtacag aaccagctta tcctggtcct gccaaaacac taccaactca    1740
tccaggctta tgttttgaga atttgtaaaa tggcatggca gttctccagt cttgttgaaa    1800
tatgcttgac tcttcatgga agcagcacca tagagcagga gggtcatcac aaagagaatg    1860
ttattcagtt ccatagtgca tctgagatac atcttgg                              1897

<210> SEQ ID NO 9
<211> LENGTH: 987
<212> TYPE: DNA
<213> ORGANISM: Canis familiaris

<400> SEQUENCE: 9
atgtatctca gatgcactat ggaactgaat aacattctct ttgtgatgac cctcctgctc      60
tatggtgctg cttccatgaa gagtcaagca tatttcaaca agactggaga actgccatgc     120
cattttacaa attctcaaaa cataagcctg gatgagttgg tagtgttttg gcaggaccag     180
gataagctgg ttctgtacga gctatacaga ggcaaagaga accctcaaaa tgttcatcgc     240
aagtataagg gccgcacaag ctttgacaaa gacaattgga ccctgagact ccataatatt     300
cagatcaagg acaagggctt gtatcaatgt ttcgttcatc ataaagggcc caaaggactc     360
gttcccatgc accagatgaa ttctgaccta tcagtgcttg ctaacttcag tcaacctgaa     420
ataatggtaa cttctaatag aacagaaaat tctggcatca taaatttgac ctgctcatcc     480
atacaaggtt acccagaacc caaggagatg tattttttgg taaaaaccga gaattcaagt     540
actaagtatg atactgtcat gaagaaatct caaaataatg tcacagaact ctacaacgtt     600
tctatcagct tgtccttctc agtccctgaa gcaagcaatg tgagcatctt ctgtgtcctg     660
caacttgagt caatgaagct tccctcccta ccttataata tagatgcaca tacgaaaccc     720 accccctgatg gagaccacat cctctggatt gcggctctgc ttgtaatgtt ggtcattttg     780
tgtgggatgg tgttctttct aacactaagg aaaaggaaga agaagcagcc tggcccctct     840
catgaatgtg aaaccaacaa agtggagaga aagaaagtg agcagaccaa ggaaagagta     900
cggtaccatg aaacggaaag atctgatgaa gcccagtgtg ttaacatttc gaagacagct     960
tcaggcgaca acagtactac acagttt                                          987

<210> SEQ ID NO 10
<211> LENGTH: 987
<212> TYPE: DNA
<213> ORGANISM: Canis familiaris

<400> SEQUENCE: 10
aaactgtgta gtactgttgt cgcctgaagc tgtcttcgaa atgttaacac actgggcttc      60
atcagatctt tccgtttcat ggtaccgtac tctttccttg gtctgctcac tttcttttct     120
ctccactttg ttggtttcac attcatgaga ggggccaggc tgcttcttct tccttttcct     180
tagtgttaga aagaacacca tcccacacaa aatgaccaac attacaagca gagccgcaat     240
ccagaggatg tggtctccat caggggtggg tttcgtatgt gcatctatat tataaggtag     300
ggagggaagc ttcattgact caagttgcag gacacagaag atgctcacat tgcttgcttc     360
```

-continued

```
agggactgag aaggacaagc tgatagaaac gttgtagagt tctgtgacat tattttgaga      420
tttcttcatg acagtatcat acttagtact tgaattctcg gttttttacca aaaaatacat    480 ctccttgggt tctgggtaac cttgtatgga tgagcaggtc aaatttatga tgccagaatt     540
ttctgttcta ttagaagtta ccattatttc aggttgactg aagttagcaa gcactgatag     600
gtcagaattc atctggtgca tgggaacgag tcctttgggc cctttatgat gaacgaaaca     660
ttgatacaag cccttgtcct tgatctgaat attatgagt ctcagggtcc aattgtcttt      720
gtcaaagctt gtgcggccct tatacttgcg atgaacattt tgagggttct ctttgcctct     780
gtatagctcg tacagaacca gcttatcctg gtcctgccaa acactacca actcatccag      840 gcttatgttt tgagaatttg taaaatggca tggcagttct ccagtcttgt tgaaatatgc     900
ttgactcttc atggaagcag caccatagag caggagggtc atcacaaaga gaatgttatt    960
cagttccata gtgcatctga gatacat                                          987
```

```
<210> SEQ ID NO 11
<211> LENGTH: 1024
<212> TYPE: DNA
<213> ORGANISM: Canis familiaris
<220> FEATURE:
<221> NAME/KEY: CDS
<222> LOCATION: (79)..(783)

<400> SEQUENCE: 11
```

```
ctttgacgtt tgttttgtt  ttgttctaac acaagaaaaa aaaaaagag gagttatcct       60 tcagcagcag cagaagcc atg gat tac aca gcg aag tgg aga aca cca cca       111
                    Met Asp Tyr Thr Ala Lys Trp Arg Thr Pro Pro
                     1               5                  10 ctc aaa cac cca tat ctc aag gtc tct cag ctc ttg gtg cta gct agt      159
Leu Lys His Pro Tyr Leu Lys Val Ser Gln Leu Leu Val Leu Ala Ser
         15                  20                  25 ctc ttt tac ttc tgt tca ggc atc atc cag gtg aac aag aca gtg aaa      207
Leu Phe Tyr Phe Cys Ser Gly Ile Ile Gln Val Asn Lys Thr Val Lys
     30                  35                  40 gaa gta gca gta ctg tcc tgt gat tac aac att tcc act aca gaa ctg      255
Glu Val Ala Val Leu Ser Cys Asp Tyr Asn Ile Ser Thr Thr Glu Leu
 45                  50                  55 atg aaa gtt cga atc tat tgg caa aag gat gat gaa gtg gtg ctg gct      303
Met Lys Val Arg Ile Tyr Trp Gln Lys Asp Asp Glu Val Val Leu Ala
 60                  65                  70                  75 gtc aca tct gga caa acg aaa gtg tgg tcc aag tat gag aat cgc acc      351
Val Thr Ser Gly Gln Thr Lys Val Trp Ser Lys Tyr Glu Asn Arg Thr
             80                  85                  90 ttt gct gac ttc acc aat aac ctc tcc atc gtg att atg gct ctg cgc      399
Phe Ala Asp Phe Thr Asn Asn Leu Ser Ile Val Ile Met Ala Leu Arg
         95                  100                 105 ctg tca gac aat ggc aaa tac acc tgt atc gtt caa aag act gaa aaa      447
Leu Ser Asp Asn Gly Lys Tyr Thr Cys Ile Val Gln Lys Thr Glu Lys
     110                 115                 120 agg tct tac aaa gtg aaa cac atg act tcg gtg atg tta ttg gtc aga      495
Arg Ser Tyr Lys Val Lys His Met Thr Ser Val Met Leu Leu Val Arg
 125                 130                 135 gct gac ttc cct gtc cct agt ata act gac ctt gga aat cca tcc cat      543
Ala Asp Phe Pro Val Pro Ser Ile Thr Asp Leu Gly Asn Pro Ser His
140                 145                 150                 155 gac atc aaa agg ata atg tgt tca acc tct gga ggt ttt cca aag cct      591
Asp Ile Lys Arg Ile Met Cys Ser Thr Ser Gly Gly Phe Pro Lys Pro
             160                 165                 170
```

-continued

| | | |
|---|---|---|
| cac ctc tcc tgg tgg gaa aat gaa gaa gaa ttg aat gct gcc aac aca<br>His Leu Ser Trp Trp Glu Asn Glu Glu Glu Leu Asn Ala Ala Asn Thr<br>            175                 180               185 | 639 |
| aca gtt tcc caa gac ccg gac act gag ttg tac act att agt agt gaa<br>Thr Val Ser Gln Asp Pro Asp Thr Glu Leu Tyr Thr Ile Ser Ser Glu<br>190                    195                 200 | 687 |
| ctg gat ttc aat ata aca agc aac cat agc ttt gtg tgt ctt gtc aag<br>Leu Asp Phe Asn Ile Thr Ser Asn His Ser Phe Val Cys Leu Val Lys<br>205                    210               215 | 735 |
| tat gga gac tta aca gta tca cag atc ttc aac tgg caa aaa tgt aag<br>Tyr Gly Asp Leu Thr Val Ser Gln Ile Phe Asn Trp Gln Lys Cys Lys<br>220                    225               230              235 | 783 |
| taacattgtt ctgaggagtt tctactgtgt aaatctaaa agaaaataa ctcagccaga | 843 |
| tacattttgg aattatgtat gttaactttg atagcatttc ttgtatttt agacccataa | 903 |
| atgataatga agtgatattg tgacttgtta aggtcactgt acaggtatgg ccataatgtt | 963 |
| actaatttta tttcctttaa taaaccttct aaaactgaga catccaaaaa aaaaaaaaa | 1023 |
| a | 1024 |

<210> SEQ ID NO 12
<211> LENGTH: 235
<212> TYPE: PRT
<213> ORGANISM: Canis familiaris

<400> SEQUENCE: 12

```
Met Asp Tyr Thr Ala Lys Trp Arg Thr Pro Leu Lys His Pro Tyr
  1               5                  10                  15

Leu Lys Val Ser Gln Leu Leu Val Leu Ala Ser Leu Phe Tyr Phe Cys
                 20                  25                  30

Ser Gly Ile Ile Gln Val Asn Lys Thr Val Lys Glu Val Ala Val Leu
             35                  40                  45

Ser Cys Asp Tyr Asn Ile Ser Thr Thr Glu Leu Met Lys Val Arg Ile
         50                  55                  60

Tyr Trp Gln Lys Asp Asp Glu Val Val Leu Ala Val Thr Ser Gly Gln
 65                  70                  75                  80

Thr Lys Val Trp Ser Lys Tyr Glu Asn Arg Thr Phe Ala Asp Phe Thr
                 85                  90                  95

Asn Asn Leu Ser Ile Val Ile Met Ala Leu Arg Leu Ser Asp Asn Gly
            100                 105                 110

Lys Tyr Thr Cys Ile Val Gln Lys Thr Glu Lys Arg Ser Tyr Lys Val
            115                 120                 125

Lys His Met Thr Ser Val Met Leu Leu Val Arg Ala Asp Phe Pro Val
        130                 135                 140

Pro Ser Ile Thr Asp Leu Gly Asn Pro Ser His Asp Ile Lys Arg Ile
145                 150                 155                 160

Met Cys Ser Thr Ser Gly Gly Phe Pro Lys Pro His Leu Ser Trp Trp
                165                 170                 175

Glu Asn Glu Glu Glu Leu Asn Ala Ala Asn Thr Thr Val Ser Gln Asp
            180                 185                 190

Pro Asp Thr Glu Leu Tyr Thr Ile Ser Ser Glu Leu Asp Phe Asn Ile
        195                 200                 205

Thr Ser Asn His Ser Phe Val Cys Leu Val Lys Tyr Gly Asp Leu Thr
    210                 215                 220

Val Ser Gln Ile Phe Asn Trp Gln Lys Cys Lys
225                 230                 235
```

<210> SEQ ID NO 13
<211> LENGTH: 1024
<212> TYPE: DNA
<213> ORGANISM: Canis familiaris

<400> SEQUENCE: 13

| | | | | | |
|---|---|---|---|---|---|
| ttttttttttt | tttttttggat | gtctcagttt | tagaaggttt | attaaaggaa | ataaaattag | 60 |
| taacattatg | gccatacctg | tacagtgacc | ttaacaagtc | acaatatcac | ttcattatca | 120 |
| tttatgggtc | taaaaataca | agaaatgcta | tcaaagttaa | catacataat | tccaaaatgt | 180 |
| atctggctga | gttattttct | ttttagattt | tacacagtag | aaactcctca | gaacaatgtt | 240 |
| acttacattt | tgccagttg | aagatctgtg | atactgttaa | gtctccatac | ttgacaagac | 300 |
| acacaaagct | atggttgctt | gttatattga | aatccagttc | actactaata | gtgtacaact | 360 |
| cagtgtccgg | gtcttgggaa | actgttgtgt | tggcagcatt | caattcttct | tcattttccc | 420 |
| accaggagag | gtgaggcttt | ggaaaacctc | cagaggttga | acacattatc | cttttgatgt | 480 |
| catgggatgg | atttccaagg | tcagttatac | tagggacagg | gaagtcagct | ctgaccaata | 540 |
| acatcaccga | agtcatgtgt | ttcactttgt | aagaccttt | ttcagtcttt | tgaacgatac | 600 |
| aggtgtattt | gccattgtct | gacaggcgca | gagccataat | cacgatggag | aggttattgg | 660 |
| tgaagtcagc | aaaggtgcga | ttctcatact | tggaccacac | tttcgtttgt | ccagatgtga | 720 |
| cagccagcac | cacttcatca | tccttttgcc | aatagattcg | aactttcatc | agttctgtag | 780 |
| tggaaatgtt | gtaatcacag | gacagtactg | ctacttcttt | cactgtcttg | ttcacctgga | 840 |
| tgatgcctga | acagaagtaa | aagagactag | ctagcaccaa | gagctgagag | accttgagat | 900 |
| atgggtgttt | gagtggtggt | gttctccact | tcgctgtgta | atccatggct | tctgctgctg | 960 |
| ctgaaggata | actcctcttt | tttttttttc | ttgtgttaga | acaaaacaaa | acaaaacgtc | 1020 |
| aaag | | | | | | 1024 |

<210> SEQ ID NO 14
<211> LENGTH: 705
<212> TYPE: DNA
<213> ORGANISM: Canis familiaris

<400> SEQUENCE: 14

| | | | | | |
|---|---|---|---|---|---|
| atggattaca | cagcgaagtg | gagaacacca | ccactcaaac | acccatatct | caaggtctct | 60 |
| cagctcttgg | tgctagctag | tctcttttac | ttctgttcag | gcatcatcca | ggtgaacaag | 120 |
| acagtgaaag | aagtagcagt | actgtcctgt | gattacaaca | tttccactac | agaactgatg | 180 |
| aaagttcgaa | tctattggca | aaaggatgat | gaagtggtgc | tggctgtcac | atctggacaa | 240 |
| acgaaagtgt | ggtccaagta | tgagaatcgc | acctttgctg | acttcaccaa | taacctctcc | 300 |
| atcgtgatta | tggctctgcg | cctgtcagac | aatggcaaat | acacctgtat | cgttcaaaag | 360 |
| actgaaaaaa | ggtcttacaa | agtgaaacac | atgacttcgg | tgatgttatt | ggtcagagct | 420 |
| gacttccctg | tccctagtat | aactgacctt | ggaaatccat | cccatgacat | caaaaggata | 480 |
| atgtgttcaa | cctctggagg | ttttccaaag | cctcacctct | cctggtggga | aaatgaagaa | 540 |
| gaattgaatg | ctgccaacac | aacagtttcc | caagacccgg | acactgagtt | gtacactatt | 600 |
| agtagtgaac | tggatttcaa | tataacaagc | aaccatagct | tgtgtgtctc | tgtcaagtat | 660 |
| ggagacttaa | cagtatcaca | gatcttcaac | tggcaaaaat | gtaag | | 705 |

<210> SEQ ID NO 15
<211> LENGTH: 705

```
<212> TYPE: DNA
<213> ORGANISM: Canis familiaris

<400> SEQUENCE: 15
cttacatttt tgccagttga agatctgtga tactgttaag tctccatact tgacaagaca      60
cacaaagcta tggttgcttg ttatattgaa atccagttca ctactaatag tgtacaactc     120
agtgtccggg tcttgggaaa ctgttgtgtt ggcagcattc aattcttctt cattttccca     180
ccaggagagg tgaggctttg gaaaacctcc agaggttgaa cacattatcc ttttgatgtc     240
atgggatgga tttccaaggt cagttatact agggacaggg aagtcagctc tgaccaataa     300
catcaccgaa gtcatgtgtt tcactttgta agaccttttt tcagtctttt gaacgataca     360
ggtgtatttg ccattgtctg acaggcgcag agccataatc acgatggaga ggttattggt     420
gaagtcagca aaggtgcgat tctcatactt ggaccacact ttcgtttgtc cagatgtgac     480
agccagcacc acttcatcat ccttttgcca atagattcga actttcatca gttctgtagt     540
ggaaatgttg taatcacagg acagtactgc tacttctttc actgtcttgt tcacctggat     600
gatgcctgaa cagaagtaaa agagactagc tagcaccaag agctgagaga ccttgagata     660
tgggtgtttg agtggtggtg ttctccactt cgctgtgtaa tccat                     705

<210> SEQ ID NO 16
<211> LENGTH: 1795
<212> TYPE: DNA
<213> ORGANISM: Canis familiaris
<220> FEATURE:
<221> NAME/KEY: CDS
<222> LOCATION: (7)..(846)

<400> SEQUENCE: 16 gccaag atg tat ctc aga tgc act atg gaa ctg aat aac att ctc ttt         48
       Met Tyr Leu Arg Cys Thr Met Glu Leu Asn Asn Ile Leu Phe
         1               5                  10 gtg atg acc ctc ctg ctc tat ggt gct gct tcc atg aag agt caa gca        96
Val Met Thr Leu Leu Leu Tyr Gly Ala Ala Ser Met Lys Ser Gln Ala
 15                  20                  25                  30 tat ttc aac aag act gga gaa ctg cca tgc cat ttt aca aat tct caa       144
Tyr Phe Asn Lys Thr Gly Glu Leu Pro Cys His Phe Thr Asn Ser Gln
                 35                  40                  45 aac ata agc ctg gat gag ttg gta gtg ttt tgg cag gac cag gat aag       192
Asn Ile Ser Leu Asp Glu Leu Val Val Phe Trp Gln Asp Gln Asp Lys
             50                  55                  60 ctg gtt ctg tac gag cta tac aga ggc aaa gag aac cct caa aat gtt       240
Leu Val Leu Tyr Glu Leu Tyr Arg Gly Lys Glu Asn Pro Gln Asn Val
 65                  70                  75 cat cgc aag tat aag ggc cgc aca agc ttt gac aaa gac aat tgg acc       288
His Arg Lys Tyr Lys Gly Arg Thr Ser Phe Asp Lys Asp Asn Trp Thr
             80                  85                  90 ctg aga ctc cat aat att cag atc aag gac aag ggc ttg tat caa tgt       336
Leu Arg Leu His Asn Ile Gln Ile Lys Asp Lys Gly Leu Tyr Gln Cys
 95                 100                 105                 110 ttc gtt cat cat aaa ggg ccc aaa gga ctc gtt ccc atg cac cag atg       384
Phe Val His His Lys Gly Pro Lys Gly Leu Val Pro Met His Gln Met
                115                 120                 125 aat tct gac cta tca gtg ctt gct aac ttc agt caa cct gaa ata atg       432
Asn Ser Asp Leu Ser Val Leu Ala Asn Phe Ser Gln Pro Glu Ile Met
            130                 135                 140 gta act tct aat aga aca gaa aat tct ggc atc ata aat ttg acc tgc       480
Val Thr Ser Asn Arg Thr Glu Asn Ser Gly Ile Ile Asn Leu Thr Cys
145                 150                 155
```

| | | | | | | | | | | | | | | | |
|---|---|---|---|---|---|---|---|---|---|---|---|---|---|---|---|
| tca | tcc | ata | caa | ggt | tac | cca | gaa | ccc | aag | gag | atg | tat | ttt | ttg | gta | 528
| Ser | Ser | Ile | Gln | Gly | Tyr | Pro | Glu | Pro | Lys | Glu | Met | Tyr | Phe | Leu | Val |
| | | 160 | | | | 165 | | | | | 170 | | | | |
| aaa | acc | gag | aat | tca | agt | act | aag | tat | gat | act | gtc | atg | aag | aaa | tct | 576
| Lys | Thr | Glu | Asn | Ser | Ser | Thr | Lys | Tyr | Asp | Thr | Val | Met | Lys | Lys | Ser |
| 175 | | | | | 180 | | | | | 185 | | | | | 190 |
| caa | aat | aat | gtc | aca | gaa | ctc | tac | aac | gtt | tct | atc | agc | ttg | tcc | ttc | 624
| Gln | Asn | Asn | Val | Thr | Glu | Leu | Tyr | Asn | Val | Ser | Ile | Ser | Leu | Ser | Phe |
| | | | | 195 | | | | | 200 | | | | | 205 | |
| tca | gtc | cct | gaa | gca | agc | aat | gtg | agc | atc | ttc | tgt | gtc | ctg | caa | ctt | 672
| Ser | Val | Pro | Glu | Ala | Ser | Asn | Val | Ser | Ile | Phe | Cys | Val | Leu | Gln | Leu |
| | | | 210 | | | | | 215 | | | | | 220 | | |
| gag | tca | atg | aag | ctt | ccc | tcc | cta | cct | tat | aat | ata | gaa | acc | aac | aaa | 720
| Glu | Ser | Met | Lys | Leu | Pro | Ser | Leu | Pro | Tyr | Asn | Ile | Glu | Thr | Asn | Lys |
| | | | 225 | | | | | 230 | | | | | 235 | | |
| gtg | gag | aga | aaa | gaa | agt | gag | cag | acc | aag | gaa | aga | gta | cgg | tac | cat | 768
| Val | Glu | Arg | Lys | Glu | Ser | Glu | Gln | Thr | Lys | Glu | Arg | Val | Arg | Tyr | His |
| | 240 | | | | | 245 | | | | | 250 | | | | |
| gaa | acg | gaa | aga | tct | gat | gaa | gcc | cag | tgt | gtt | aac | att | tcg | aag | aca | 816
| Glu | Thr | Glu | Arg | Ser | Asp | Glu | Ala | Gln | Cys | Val | Asn | Ile | Ser | Lys | Thr |
| 255 | | | | | 260 | | | | | 265 | | | | | 270 |
| gct | tca | ggc | gac | aac | agt | act | aca | cag | ttt | taattaaaga | gtaaagtcca | | | | | 866
| Ala | Ser | Gly | Asp | Asn | Ser | Thr | Thr | Gln | Phe | | | | | | |
| | | | | 275 | | | | | 280 | | | | | | |

| | |
|---|---|
| tccattgttt atatgccttc cctttcaaat tttggcttgc cttttctcg tccattaata | 926 |
| ttattattgc cactaataat aagaggcttt ccagggctcc ctctaaatga gagagcctcc | 986 |
| ctataatgcc agttctgctc cctacaccag gagcagattt taactgcttc ttttcatctc | 1046 |
| agagcacact tgtgggccat gctcacctga ctggctcctg gctcaggaat aatgtttaag | 1106 |
| actaacacct cctgtttcag attcagcctt cttttcttaa ttttatacat tgtgttttat | 1166 |
| gtagaactcc caattactgg actaatggct tttatctatg cttaattcta agatagtgcc | 1226 |
| tcattccatc ttgtatattt gtgactacct ctgcagtctg ggtgggagtt ttgtatgtta | 1286 |
| tggctttata gtgttgcttt aatattttga gacataaaga gatgtgtact ataataatgt | 1346 |
| aattactatg ccctgagaaa attctaccca ctgctgagga gctcttgctc ctctgtgagg | 1406 |
| gtcagtacga aaatggtggc ttggtgtgct gacaacaatg agcagaccaa ctcaaaattt | 1466 |
| ggaagattag gaatgatgga gatagaacca gctctgagtc ctggagccac ttctatctgg | 1526 |
| gctgctgcta atctgaggaa gatccacctg cctaacaagc tatggataag ccttagcagg | 1586 |
| gagctctttg tgaagcagga aagcactatg cactgtgaac cctacttctc ttcttgaaaa | 1646 |
| aaatggctga gatgatggct cagggcaact gttcaagagc caactgagag atcacaatac | 1706 |
| ttaaaagaga aaaagaaaa aagaaaaaaa aaaaaaaaa aaaaaaaaa aaaaaaaaa | 1766 |
| aaaaaaaaa aaaaaaaaa aaaaaaaa | 1795 |

<210> SEQ ID NO 17
<211> LENGTH: 280
<212> TYPE: PRT
<213> ORGANISM: Canis familiaris

<400> SEQUENCE: 17

| | | | | | | | | | | | | | | |
|---|---|---|---|---|---|---|---|---|---|---|---|---|---|---|
| Met | Tyr | Leu | Arg | Cys | Thr | Met | Glu | Leu | Asn | Asn | Ile | Leu | Phe | Val | Met |
| 1 | | | | 5 | | | | | 10 | | | | | 15 | |
| Thr | Leu | Leu | Leu | Tyr | Gly | Ala | Ala | Ser | Met | Lys | Ser | Gln | Ala | Tyr | Phe |
| | | | 20 | | | | | 25 | | | | | 30 | | |

-continued

```
Asn Lys Thr Gly Glu Leu Pro Cys His Phe Thr Asn Ser Gln Asn Ile
         35                  40                  45

Ser Leu Asp Glu Leu Val Val Phe Trp Gln Asp Gln Asp Lys Leu Val
     50                  55                  60

Leu Tyr Glu Leu Tyr Arg Gly Lys Glu Asn Pro Gln Asn Val His Arg
 65                  70                  75                  80

Lys Tyr Lys Gly Arg Thr Ser Phe Asp Lys Asp Asn Trp Thr Leu Arg
                 85                  90                  95

Leu His Asn Ile Gln Ile Lys Asp Lys Gly Leu Tyr Gln Cys Phe Val
            100                 105                 110

His His Lys Gly Pro Lys Gly Leu Val Pro Met His Gln Met Asn Ser
        115                 120                 125

Asp Leu Ser Val Leu Ala Asn Phe Ser Gln Pro Glu Ile Met Val Thr
    130                 135                 140

Ser Asn Arg Thr Glu Asn Ser Gly Ile Ile Asn Leu Thr Cys Ser Ser
145                 150                 155                 160

Ile Gln Gly Tyr Pro Glu Pro Lys Glu Met Tyr Phe Leu Val Lys Thr
                165                 170                 175

Glu Asn Ser Ser Thr Lys Tyr Asp Thr Val Met Lys Lys Ser Gln Asn
            180                 185                 190

Asn Val Thr Glu Leu Tyr Asn Val Ser Ile Ser Leu Ser Phe Ser Val
        195                 200                 205

Pro Glu Ala Ser Asn Val Ser Ile Phe Cys Val Leu Gln Leu Glu Ser
    210                 215                 220

Met Lys Leu Pro Ser Leu Pro Tyr Asn Ile Glu Thr Asn Lys Val Glu
225                 230                 235                 240

Arg Lys Glu Ser Glu Gln Thr Lys Glu Arg Val Arg Tyr His Glu Thr
                245                 250                 255

Glu Arg Ser Asp Glu Ala Gln Cys Val Asn Ile Ser Lys Thr Ala Ser
            260                 265                 270

Gly Asp Asn Ser Thr Thr Gln Phe
        275                 280
```

<210> SEQ ID NO 18
<211> LENGTH: 1795
<212> TYPE: DNA
<213> ORGANISM: Canis familiaris

<400> SEQUENCE: 18

| | | |
|---|---|---|
| tttttttttt tttttttttt tttttttttt tttttttttt tttttttttt tttttttttt | 60 |
| tttttttcttt tttctttttt ctcttttaag tattgtgatc tctcagttgg ctcttgaaca | 120 |
| gttgccctga gccatcatct cagccatttt tttcaagaag agaagtaggg ttcacagtgc | 180 |
| atagtgcttt cctgcttcac aaagagctcc ctgctaaggc ttatccatag cttgttaggc | 240 |
| aggtggatct tcctcagatt agcagcagcc cagatagaag tggctccagg actcagagct | 300 |
| ggttctatct ccatcattcc taatcttcca aattttgagt tggtctgctc attgttgtca | 360 |
| gcacaccaag ccaccatttt cgtactgacc ctcacagagg agcaagagct cctcagcagt | 420 |
| gggtagaatt ttctcagggc atagtaatta cattattata gtacacatct ctttatgtct | 480 |
| caaaatatta aagcaacact ataaagccat aacatacaaa actcccaccc agactgcaga | 540 |
| ggtagtcaca aatatacaag atggaatgag gcactatctt agaattaagc atagataaaa | 600 |
| gccattagtc cagtaattgg gagttctaca taaacacaa tgtataaaat taagaaaaga | 660 |
| aggctgaatc tgaaacagga ggtgttagtc ttaaacatta ttcctgagcc aggagccagt | 720 |

-continued

```
caggtgagca tggcccacaa gtgtgctctg agatgaaaag aagcagttaa aatctgctcc      780
tggtgtaggg agcagaactg gcattatagg gaggctctct catttagagg gagccctgga      840
aagcctctta ttattagtgg caataataat attaatggac gagaaaaagg caagccaaaa      900
tttgaaaggg aaggcatata acaatggat ggactttact ctttaattaa aactgtgtag       960
tactgttgtc gcctgaagct gtcttcgaaa tgttaacaca ctgggcttca tcagatcttt     1020
ccgtttcatg gtaccgtact ctttccttgg tctgctcact ttcttttctc tccactttgt     1080
tggtttctat attataaggt agggaggaa gcttcattga ctcaagttgc aggacacaga      1140
agatgctcac attgcttgct tcagggactg agaaggacaa gctgatagaa acgttgtaga     1200
gttctgtgac attattttga gatttcttca tgacagtatc atacttagta cttgaattct     1260
cggttttac caaaaaatac atctccttgg gttctgggta accttgtatg gatgagcagg     1320
tcaaatttat gatgccagaa ttttctgttc tattagaagt taccattatt tcaggttgac     1380
tgaagttagc aagcactgat aggtcagaat tcatctggtg catgggaacg agtcctttgg     1440
gccctttatg atgaacgaaa cattgataca agcccttgtc cttgatctga atattatgga     1500
gtctcagggt ccaattgtct tgtcaaagc ttgtgcggcc cttatacttg cgatgaacat      1560
tttgagggtt ctcttttgcct ctgtatagct cgtacagaac cagcttatcc tggtcctgcc    1620
aaaacactac caactcatcc aggcttatgt tttgagaatt tgtaaaatgg catggcagtt     1680
ctccagtctt gttgaaatat gcttgactct tcatggaagc agcaccatag agcaggaggg     1740
tcatcacaaa gagaatgtta ttcagttcca tagtgcatct gagatacatc ttggc          1795
```

<210> SEQ ID NO 19
<211> LENGTH: 840
<212> TYPE: DNA
<213> ORGANISM: Canis familiaris

<400> SEQUENCE: 19

```
atgtatctca gatgcactat ggaactgaat aacattctct ttgtgatgac cctcctgctc       60
tatggtgctg cttccatgaa gagtcaagca tatttcaaca agactggaga actgccatgc      120
cattttacaa attctcaaaa cataagcctg gatgagttgg tagtgttttg gcaggaccag      180
gataagctgg ttctgtacga gctatacaga ggcaaagaga accctcaaaa tgttcatcgc      240
aagtataagg gccgcacaag cttgacaaa gacaattgga ccctgagact ccataatatt      300
cagatcaagg acaagggctt gtatcaatgt ttcgttcatc ataaagggcc caaggactc      360
gttcccatgc accagatgaa ttctgaccta tcagtgcttg ctaacttcag tcaacctgaa     420
ataatggtaa cttctaatag aacagaaaat tctggcatca taaatttgac ctgctcatcc    480
atacaaggtt acccagaacc caaggagatg tatttttgg taaaaccga gaattcaagt     540
actaagtatg atactgtcat gaagaaatct caaaataatg tcacagaact ctacaacgtt     600
tctatcagct tgtccttctc agtccctgaa gcaagcaatg tgagcatctt ctgtgtcctg    660
caacttgagt caatgaagct tccctcccta ccttataata tagaaaccaa caaagtggag    720
agaaaagaaa gtgagcagac caaggaaaga gtacggtacc atgaaacgga aagatctgat    780
gaagcccagt gtgttaacat ttcgaagaca gcttcaggcg acaacagtac tacacagttt    840
```

<210> SEQ ID NO 20
<211> LENGTH: 840
<212> TYPE: DNA
<213> ORGANISM: Canis familiaris

```
<400> SEQUENCE: 20
aaactgtgta gtactgttgt cgcctgaagc tgtcttcgaa atgttaacac actgggcttc      60
atcagatctt tccgtttcat ggtaccgtac tctttccttg gtctgctcac tttcttttct     120
ctccactttg ttggtttcta tattataagg tagggaggga agcttcattg actcaagttg     180
caggacacag aagatgctca cattgcttgc ttcagggact gagaaggaca agctgataga     240
aacgttgtag agttctgtga cattattttg agatttcttc atgacagtat catacttagt     300
acttgaattc tcggttttta ccaaaaaata catctccttg ggttctgggt aaccttgtat     360
ggatgagcag gtcaaattta tgatgccaga attttctgtt ctattagaag ttaccattat     420
ttcaggttga ctgaagttag caagcactga taggtcagaa ttcatctggt gcatgggaac     480
gagtcctttg ggccctttat gatgaacgaa acattgatac aagcccttgt ccttgatctg     540
aatattatgg agtctcaggg tccaattgtc tttgtcaaag cttgtgcggc ccttatactt     600
gcgatgaaca ttttgagggt tctctttgcc tctgtatagc tcgtacagaa ccagcttatc     660
ctggtcctgc caaaacacta ccaactcatc caggcttatg ttttgagaat ttgtaaaatg     720
gcatggcagt tctccagtct tgttgaaata tgcttgactc ttcatggaag cagcaccata     780
gagcaggagg gtcatcacaa agagaatgtt attcagttcc atagtgcatc tgagatacat     840

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 21
gtcaragctg acttccct                                                    18

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 22
gtagaaactc ctcagaacaa tg                                               22

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 23
gtagtatttt ggcaggacc                                                   19

<210> SEQ ID NO 24
<211> LENGTH: 23
<212> TYPE: DNA
<213> ORGANISM: Canis familiaris

<400> SEQUENCE: 24
tagaygsgca ggtcaaattt atg                                              23
```

<210> SEQ ID NO 25
<211> LENGTH: 2830
<212> TYPE: DNA
<213> ORGANISM: Felis catus
<220> FEATURE:
<221> NAME/KEY: CDS
<222> LOCATION: (179)..(1174)

<400> SEQUENCE: 25

| | |
|---|---|
| gttttttttt ttttgagttc tagtctcagc cctgacatta tttctttctc tacaaagagt | 60 |
| gttaggaagt tatggggagc tcacaaaggc tcctcatcgt ttattcttaa caccttgttt | 120 |
| ctgtgttcct cgggaatgtc actgagctta tacatctggt ctctgggagc tgcagtgg | 178 |

| | |
|---|---|
| atg ggc att tgt gac agc act atg gga ctg agt cac act ctc ctt gtg<br>Met Gly Ile Cys Asp Ser Thr Met Gly Leu Ser His Thr Leu Leu Val<br>1               5                  10                  15 | 226 |
| atg gcc ctc ctg ctc tct ggt gtt tct tcc atg aag agt caa gca tat<br>Met Ala Leu Leu Leu Ser Gly Val Ser Ser Met Lys Ser Gln Ala Tyr<br>            20                  25                  30 | 274 |
| ttc aac aag act gga gaa ctg cca tgc cat ttt aca aac tct caa aac<br>Phe Asn Lys Thr Gly Glu Leu Pro Cys His Phe Thr Asn Ser Gln Asn<br>        35                  40                  45 | 322 |
| ata agc ctg gat gag ctg gta gta ttt tgg cag gac cag gat aag ctg<br>Ile Ser Leu Asp Glu Leu Val Val Phe Trp Gln Asp Gln Asp Lys Leu<br>    50                  55                  60 | 370 |
| gtt ctg tat gag ata ttc aga ggc aaa gag aac cct caa aat gtt cat<br>Val Leu Tyr Glu Ile Phe Arg Gly Lys Glu Asn Pro Gln Asn Val His<br>65                  70                  75                  80 | 418 |
| ctc aaa tat aag ggc cgt aca agc ttt gac aag gac aac tgg acc ctg<br>Leu Lys Tyr Lys Gly Arg Thr Ser Phe Asp Lys Asp Asn Trp Thr Leu<br>                85                  90                  95 | 466 |
| aga ctc cac aat gtt cag atc aag gac aag ggc aca tat cac tgt ttc<br>Arg Leu His Asn Val Gln Ile Lys Asp Lys Gly Thr Tyr His Cys Phe<br>            100                 105                 110 | 514 |
| att cat tat aaa ggg ccc aaa gga cta gtt ccc atg cac caa atg agt<br>Ile His Tyr Lys Gly Pro Lys Gly Leu Val Pro Met His Gln Met Ser<br>        115                 120                 125 | 562 |
| tct gac cta tca gtg ctt gct aac ttc agt caa cct gaa ata aca gta<br>Ser Asp Leu Ser Val Leu Ala Asn Phe Ser Gln Pro Glu Ile Thr Val<br>    130                 135                 140 | 610 |
| act tct aat aga aca gaa aat tct ggc atc ata aat ttg acc tgc tca<br>Thr Ser Asn Arg Thr Glu Asn Ser Gly Ile Ile Asn Leu Thr Cys Ser<br>145                 150                 155                 160 | 658 |
| tct ata caa ggt tac cca gaa cct aag gag atg tat ttt cag cta aac<br>Ser Ile Gln Gly Tyr Pro Glu Pro Lys Glu Met Tyr Phe Gln Leu Asn<br>                165                 170                 175 | 706 |
| act gag aat tca act act aag tat gat act gtc atg aag aaa tct caa<br>Thr Glu Asn Ser Thr Thr Lys Tyr Asp Thr Val Met Lys Lys Ser Gln<br>            180                 185                 190 | 754 |
| aat aat gtg aca gaa ctg tac aac gtt tct atc agc ttg cct ttt tca<br>Asn Asn Val Thr Glu Leu Tyr Asn Val Ser Ile Ser Leu Pro Phe Ser<br>        195                 200                 205 | 802 |
| gtc cct gaa gca cac aat gtg agc gtc ttt tgt gcc ctg aaa ctg gag<br>Val Pro Glu Ala His Asn Val Ser Val Phe Cys Ala Leu Lys Leu Glu<br>    210                 215                 220 | 850 |
| aca ctg gag atg ctg ctc tcc cta cct ttc aat ata gat gca caa cct<br>Thr Leu Glu Met Leu Leu Ser Leu Pro Phe Asn Ile Asp Ala Gln Pro<br>225                 230                 235                 240 | 898 |
| aag gat aaa gac cct gaa caa ggc cac ttc ctc tgg att gcg gct gta<br>Lys Asp Lys Asp Pro Glu Gln Gly His Phe Leu Trp Ile Ala Ala Val | 946 |

-continued

```
                         245                 250                255
ctt gta atg ttt gtt gtt ttt tgt ggg atg gtg tcc ttt aaa aca cta      994
Leu Val Met Phe Val Val Phe Cys Gly Met Val Ser Phe Lys Thr Leu
                260                 265                 270 agg aaa agg aag aag aag cag cct ggc ccc tct cat gaa tgt gaa acc     1042
Arg Lys Arg Lys Lys Lys Gln Pro Gly Pro Ser His Glu Cys Glu Thr
            275                 280                 285 atc aaa agg gag aga aaa gag agc aaa cag acc aac gaa aga gta cca     1090
Ile Lys Arg Glu Arg Lys Glu Ser Lys Gln Thr Asn Glu Arg Val Pro
        290                 295                 300 tac cac gta cct gag aga tct gat gaa gcc cag tgt att aac att ttg     1138
Tyr His Val Pro Glu Arg Ser Asp Glu Ala Gln Cys Ile Asn Ile Leu
305                 310                 315                 320 aag aca gcc tca ggc gac aaa agt act aca cat ttt taattaaaga          1184
Lys Thr Ala Ser Gly Asp Lys Ser Thr Thr His Phe
                    325                 330
```

| | |
|---|---|
| ataaagtcca tataactgtc cattgtttat atgcctttcc cttcaagttt tgggcttacc | 1244 |
| ttttttttgtc tattaatatt attattacca ttaataatag tggaggttcc aggactccat | 1304 |
| ctgagaaagc caccctgtaa tgccagctct gctccctacc tcaggagcag accttaactg | 1364 |
| cttcttttca tttcagagca aatttgtgcg ccaagctcac ctgactggat cctggctcag | 1424 |
| gaataatgtt taagactaac acctcctgtt tcacattcag ccttcttttc ttaattttat | 1484 |
| aaattgcgtc ttatgtagaa ctcccaatta ctggaataat ggcttttatc tatgtaattc | 1544 |
| taaggtagtg cctcattcta tcttgtatat ttgtgactga ataactacct cttcagtctt | 1604 |
| gtgggagtta tatttttat ggcttttata gtattgctat taatatcttg aaacataaag | 1664 |
| agatgtgtac tataataatg taattactat gccctgagaa atcactgct gaggagctct | 1724 |
| tgtccctctg tgaagatcag taggaaaatg gtggcttggc gtgctgacaa tgatgagcag | 1784 |
| accaactcaa aatttggaaa attaagacca tgaagatgga atcagctctg gatcctggat | 1844 |
| ccacttctat ctgggcccct gctaacctga aaggatctg cctgcggaac aagctataga | 1904 |
| taagccttag cagagaacac tgggtcaagc actgcatatt gtgaacccac ttctcttctt | 1964 |
| gaaagaaatg actgagatga tggtccagag caactatgca agagccaact gagagatcac | 2024 |
| aacactcaaa agagaaaaaa aatgaaagat cttgacaaca gagatgcata tgaatgtcct | 2084 |
| gtctgtccag tcctctgaca aaccttggga ttagcaacag gtagacagtc tgtccaaaag | 2144 |
| gacttaagac agacagcagc tcccatggtg gttggtgaga agtttggata ataatcaagt | 2204 |
| tattgtgatg tttcatctgg ctgcaggcag agcaggggag gaagagctat catcttgata | 2264 |
| atgggataaa tggaaggaag cttaggactc tttcaactta cttctgagac acaaagagct | 2324 |
| agagtggaat caggaggacc aagatgtaaa tcatctaaag gccaacttag ctggcaggtg | 2384 |
| ccctagggag agatcagctg gccaagagca ggggtggcaa atttatatct gaggactgtc | 2444 |
| tatatgtcat tataaatgat ggggaaactg ggtacacgag aggactatac tagcccagta | 2504 |
| gagatgagtc agatgacccct ggctctaaag cagcatcact aagggacgag gcagcctcag | 2564 |
| tccaaaccaa gagagaactt tgggaggccc aacccacaga aatatttctt cttattctac | 2624 |
| ataaaggaat ctagaaggtt gtagacagct gtactagcca tgcttgtcct tgtaatatta | 2684 |
| ccatttgtgt gttcttccct gcatttgctt cattaggcca taagcatctt gttggtttct | 2744 |
| aacatgtttc gtatagtgag ttcttaataa attttttctta aattgaaaaa aaaaaaaaa | 2804 |
| aaaaaaaaaa aaaaaaaaaa aaaaa | 2830 |

<210> SEQ ID NO 26
<211> LENGTH: 332
<212> TYPE: PRT
<213> ORGANISM: Felis catus

<400> SEQUENCE: 26

Met Gly Ile Cys Asp Ser Thr Met Gly Leu Ser His Thr Leu Leu Val
1               5                   10                  15

Met Ala Leu Leu Leu Ser Gly Val Ser Ser Met Lys Ser Gln Ala Tyr
                20                  25                  30

Phe Asn Lys Thr Gly Glu Leu Pro Cys His Phe Thr Asn Ser Gln Asn
            35                  40                  45

Ile Ser Leu Asp Glu Leu Val Val Phe Trp Gln Asp Gln Asp Lys Leu
        50                  55                  60

Val Leu Tyr Glu Ile Phe Arg Gly Lys Glu Asn Pro Gln Asn Val His
65                  70                  75                  80

Leu Lys Tyr Lys Gly Arg Thr Ser Phe Asp Lys Asp Asn Trp Thr Leu
                85                  90                  95

Arg Leu His Asn Val Gln Ile Lys Asp Lys Gly Thr Tyr His Cys Phe
            100                 105                 110

Ile His Tyr Lys Gly Pro Lys Gly Leu Val Pro Met His Gln Met Ser
        115                 120                 125

Ser Asp Leu Ser Val Leu Ala Asn Phe Ser Gln Pro Glu Ile Thr Val
130                 135                 140

Thr Ser Asn Arg Thr Glu Asn Ser Gly Ile Ile Asn Leu Thr Cys Ser
145                 150                 155                 160

Ser Ile Gln Gly Tyr Pro Glu Pro Lys Glu Met Tyr Phe Gln Leu Asn
                165                 170                 175

Thr Glu Asn Ser Thr Thr Lys Tyr Asp Thr Val Met Lys Lys Ser Gln
            180                 185                 190

Asn Asn Val Thr Glu Leu Tyr Asn Val Ser Ile Ser Leu Pro Phe Ser
        195                 200                 205

Val Pro Glu Ala His Asn Val Ser Val Phe Cys Ala Leu Lys Leu Glu
210                 215                 220

Thr Leu Glu Met Leu Leu Ser Leu Pro Phe Asn Ile Asp Ala Gln Pro
225                 230                 235                 240

Lys Asp Lys Asp Pro Glu Gln Gly His Phe Leu Trp Ile Ala Ala Val
                245                 250                 255

Leu Val Met Phe Val Val Phe Cys Gly Met Val Ser Phe Lys Thr Leu
            260                 265                 270

Arg Lys Arg Lys Lys Gln Pro Gly Pro Ser His Glu Cys Glu Thr
        275                 280                 285

Ile Lys Arg Glu Arg Lys Glu Ser Lys Gln Thr Asn Glu Arg Val Pro
        290                 295                 300

Tyr His Val Pro Glu Arg Ser Asp Glu Ala Gln Cys Ile Asn Ile Leu
305                 310                 315                 320

Lys Thr Ala Ser Gly Asp Lys Ser Thr Thr His Phe
                325                 330

<210> SEQ ID NO 27
<211> LENGTH: 2830
<212> TYPE: DNA
<213> ORGANISM: Felis catus

<400> SEQUENCE: 27
tttttttttt tttttttttt tttttttttt tttttttttt tcaatttaag aaaaatttat    60

-continued

```
taagaactca ctatacgaaa catgttagaa accaacaaga tgcttatggc ctaatgaagc      120
aaatgcaggg aagaacacac aaatggtaat attacaagga caagcatggc tagtacagct      180
gtctacaacc ttctagattc ctttatgtag aataagaaga aatatttctg tgggttgggc      240
ctcccaaagt tctctcttgg tttggactga ggctgcctcg tcccttagtg atgctgcttt      300
agagccaggt tcatctgact catctctact gggctagtat agtcctctcg tgtacccagt      360
ttccccatca tttataatga catatagaca gtcctcagat ataaatttgc caccccctgct     420 cttggccagc tgatctctcc ctagggcacc tgccagctaa gttggccttt agatgattta      480
catcttggtc ctcctgattc cactctagct ctttgtgtct cagaagtaag ttgaaagagt      540
cctaagcttc cttccattta tcccattatc aagatgatag ctcttcctcc cctgctctgc      600
ctgcagccag atgaaacatc acaataactt gattattatc caaacttctc accaaccacc      660
atgggagctg ctgtctgtct taagtccttt tggacagact gtctacctgt tgctaatccc      720
aaggtttgtc agaggactgg acagacagga cattcatatg catctctgtt gtcaagatct      780 ttcattttttt ttctcttttg agtgttgtga tctctcagtt ggctcttgca tagttgctct     840
ggaccatcat ctcagtcatt tctttcaaga agagaagtgg gttcacaata tgcagtgctt      900
gacccagtgt tctctgctaa ggcttatcta tagcttgttc cgcaggcaga tccttctcag      960
gttagcaagg gcccagatag aagtggatcc aggatccaga gctgattcca tcttcatggt     1020
cttaattttc caaattttga gttggtctgc tcatcattgt cagcacgcca agccaccatt     1080
ttcctactga tcttcacaga gggacaagag ctcctcagca gtgattttct cagggcatag     1140
taattacatt attatagtac acatctcttt atgtttcaag atattaatag caatactata     1200
aaagccataa aatatataac tcccacaaga ctgaagaggg agttattcag tcacaaatat     1260
acaagataga atgaggcact accttagaat tacatagata aaagccatta ttccagtaat     1320
tgggagttct acataagacg caatttataa aattaagaaa agaaggctga atgtgaaaca     1380
ggaggtgtta gtcttaaaca ttattcctga gccaggatcc agtcaggtga gcttggcgca     1440
caaatttgct ctgaaatgaa aagaagcagt taaggtctgc tcctgaggta gggagcagag     1500
ctggcattac agggtggctt tctcagatgg agtcctggaa cctccactat tattaatggt     1560
aataataata ttaatagaca aaaaaaggta agcccaaaac ttgaagggaa aggcatataa     1620
acaatggaca gttatatgga ctttattctt taattaaaaa tgtgtagtac ttttgtcgcc     1680
tgaggctgtc ttcaaaatgt taatacactg ggcttcatca gatctctcag gtacgtggta     1740
tggtactctt tcgttggtct gttgtgctctc tttctctcc cttttgatgg tttcacattc     1800
atgagagggg ccaggctgct tcttcttcct tttccttagt gtttttaaagg acaccatccc    1860 acaaaaaaca caaacatta caagtacagc cgcaatccag aggaagtggc cttgttcagg      1920
gtctttatcc ttaggttgtg catctatatt gaaaggtagg gagagcagca tctccagtgt     1980
ctccagtttc agggcacaaa agacgctcac attgtgtgct tcagggactg aaaaaggcaa     2040
gctgatagaa acgttgtaca gttctgtcac attattttga gatttcttca tgacagtatc     2100
atacttagta gttgaattct cagtgtttag ctgaaaatac atctccttag gttctgggta     2160
accttgtata gatgagcagg tcaaatttat gatgccagaa ttttctgttc tattagaagt     2220
tactgttatt tcaggttgac tgaagttagc aagcactgat aggtcagaac tcatttggtg     2280
catgggaact agtcctttgg gcccttata atgaatgaaa cagtgatatg tgcccttgtc      2340
cttgatctga acattgtgga gtctcagggt ccagttgtcc ttgtcaaagc ttgtacggcc     2400
```

```
cttatatttg agatgaacat tttgagggtt ctctttgcct ctgaatatct catacagaac    2460
cagcttatcc tggtcctgcc aaaatactac cagctcatcc aggcttatgt tttgagagtt    2520
tgtaaaatgg catggcagtt ctccagtctt gttgaaatat gcttgactct tcatggaaga    2580
aacaccagag agcaggaggg ccatcacaag gagagtgtga ctcagtccca tagtgctgtc    2640
acaaatgccc atccactgca gctcccagag accagatgta taagctcagt gacattcccg    2700
aggaacacag aaacaaggtg ttaagaataa acgatgagga gcctttgtga gctccccata    2760
acttcctaac actctttgta gagaaagaaa taatgtcagg gctgagacta gaactcaaaa    2820
aaaaaaaaac                                                          2830

<210> SEQ ID NO 28
<211> LENGTH: 996
<212> TYPE: DNA
<213> ORGANISM: Felis catus

<400> SEQUENCE: 28
atgggcattt gtgacagcac tatgggactg agtcacactc tccttgtgat ggccctcctg     60
ctctctggtg tttcttccat gaagagtcaa gcatatttca acaagactgg agaactgcca    120
tgccatttta caaactctca aaacataagc ctggatgagc tggtagtatt ttggcaggac    180
caggataagc tggttctgta tgagatattc agaggcaaag agaaccctca aaatgttcat    240
ctcaaatata agggccgtac aagctttgac aaggacaact ggaccctgag actccacaat    300
gttcagatca aggacaaggg cacatatcac tgtttcattc attataaagg gcccaaagga    360
ctagttccca tgcaccaaat gagttctgac ctatcagtgc ttgctaactt cagtcaacct    420
gaaataacag taacttctaa tagaacagaa aattctggca tcataaattt gacctgctca    480
tctatacaag gttacccaga acctaaggag atgtattttc agctaaacac tgagaattca    540
actactaagt atgatactgt catgaagaaa tctcaaaata atgtgacaga actgtacaac    600
gtttctatca gcttgccttt ttcagtccct gaagcacaca atgtgagcgt cttttgtgcc    660
ctgaaactgg agacactgga gatgctgctc tccctacctt tcaatatgga tgcacaacct    720
aaggataaag accctgaaca aggccacttc ctctggattg cggctgtact tgtaatgttt    780
gttgtttttt gtgggatggt gtcctttaaa acactaagga aaggaagaa gaagcagcct    840 ggcccctctc atgaatgtga aaccatcaaa agggagagaa aagagagcaa acagaccaac    900
gaaagagtac cataccacgt acctgagaga tctgatgaag cccagtgtat taacattttg    960
aagacagcct caggcgacaa aagtactaca catttt                              996

<210> SEQ ID NO 29
<211> LENGTH: 996
<212> TYPE: DNA
<213> ORGANISM: Felis catus

<400> SEQUENCE: 29
aaaatgtgta gtactttgt cgcctgaggc tgtcttcaaa atgttaatac actgggcttc      60
atcagatctc tcaggtacgt ggtatggtac tctttcgttg gtctgtttgc tctcttttct    120
ctcccttttg atggtttcac attcatgaga ggggccaggc tgcttcttct ccttttcct    180 tagtgtttta aaggacacca tcccacaaaa acaacaaac attacaagta cagccgcaat    240
ccagaggaag tggccttgtt cagggtcttt atccttaggt tgtgcatcta tattgaaagg    300
tagggagagc agcatctcca gtgtctccag tttcagggca caaagacgc tcacattgtg    360 tgcttcaggg actgaaaaag gcaagctgat agaaacgttg tacagttctg tcacattatt    420
```

-continued

```
ttgagatttc ttcatgacag tatcatactt agtagttgaa ttctcagtgt ttagctgaaa      480
atacatctcc ttaggttctg ggtaaccttg tatagatgag caggtcaaat ttatgatgcc      540
agaattttct gttctattag aagttactgt tatttcaggt tgactgaagt tagcaagcac      600
tgataggtca gaactcattt ggtgcatggg aactagtcct ttgggccctt tataatgaat      660
gaaacagtga tatgtgccct tgtccttgat ctgaacattg tggagtctca gggtccagtt      720
gtccttgtca aagcttgtac ggcccttata tttgagatga acattttgag ggttctcttt      780
gcctctgaat atctcataca gaaccagctt atcctggtcc tgccaaaata ctaccagctc      840
atccaggctt atgttttgag agtttgtaaa atggcatggc agttctccag tcttgttgaa      900
atatgcttga ctcttcatgg aagaaacacc agagagcagg agggccatca caaggagagt      960
gtgactcagt cccatagtgc tgtcacaaat gcccat                                996
```

<210> SEQ ID NO 30
<211> LENGTH: 509
<212> TYPE: DNA
<213> ORGANISM: Felis catus
<220> FEATURE:
<221> NAME/KEY: CDS
<222> LOCATION: (1)..(507)

<400> SEQUENCE: 30

```
ata caa ggt tac cca gaa cct aag gag atg tat ttt cag cta aac act        48
Ile Gln Gly Tyr Pro Glu Pro Lys Glu Met Tyr Phe Gln Leu Asn Thr
  1               5                  10                  15 gag aat tca act act aag tat gat act gtc atg aag aaa tct caa aat       96
Glu Asn Ser Thr Thr Lys Tyr Asp Thr Val Met Lys Lys Ser Gln Asn
             20                  25                  30 aat gtg aca gaa ctg tac aac gtt tct atc agc ttg cct ttt tca gtc      144
Asn Val Thr Glu Leu Tyr Asn Val Ser Ile Ser Leu Pro Phe Ser Val
         35                  40                  45 cct gaa gca cac aat gtg agc gtc ttt tgt gcc ctg aaa ctg gag aca      192
Pro Glu Ala His Asn Val Ser Val Phe Cys Ala Leu Lys Leu Glu Thr
     50                  55                  60 ctg gag atg ctg ctc tcc cta cct ttc aat ata gat gca caa cct aag      240
Leu Glu Met Leu Leu Ser Leu Pro Phe Asn Ile Asp Ala Gln Pro Lys
 65                  70                  75                  80 gat aaa gac cct gaa caa ggc cac ttc ctc tgg att gcg gct gta ctt      288
Asp Lys Asp Pro Glu Gln Gly His Phe Leu Trp Ile Ala Ala Val Leu
                 85                  90                  95 gta atg ttt gtt gtt ttt tgt ggg atg gtg tcc ttt aaa aca cta agg      336
Val Met Phe Val Val Phe Cys Gly Met Val Ser Phe Lys Thr Leu Arg
            100                 105                 110 aaa agg aag aag aag cag cct ggc ccc tct cat gaa tgt gaa acc atc      384
Lys Arg Lys Lys Lys Gln Pro Gly Pro Ser His Glu Cys Glu Thr Ile
        115                 120                 125 aaa agg gag aga aaa gag agc aaa cag acc aac gaa aga gta cca tac      432
Lys Arg Glu Arg Lys Glu Ser Lys Gln Thr Asn Glu Arg Val Pro Tyr
    130                 135                 140 cac gta cct gag aga tct gat gaa gcc cag tgt att aac att ttg aag      480
His Val Pro Glu Arg Ser Asp Glu Ala Gln Cys Ile Asn Ile Leu Lys
145                 150                 155                 160 aca gcc tca ggc gac aaa agt act aca ca                                509
Thr Ala Ser Gly Asp Lys Ser Thr Thr
                165
```

<210> SEQ ID NO 31
<211> LENGTH: 169

<212> TYPE: PRT
<213> ORGANISM: Felis catus

<400> SEQUENCE: 31

Ile Gln Gly Tyr Pro Glu Pro Lys Glu Met Tyr Phe Gln Leu Asn Thr
1               5                   10                  15

Glu Asn Ser Thr Thr Lys Tyr Asp Thr Val Met Lys Lys Ser Gln Asn
            20                  25                  30

Asn Val Thr Glu Leu Tyr Asn Val Ser Ile Ser Leu Pro Phe Ser Val
        35                  40                  45

Pro Glu Ala His Asn Val Ser Val Phe Cys Ala Leu Lys Leu Glu Thr
    50                  55                  60

Leu Glu Met Leu Leu Ser Leu Pro Phe Asn Ile Asp Ala Gln Pro Lys
65                  70                  75                  80

Asp Lys Asp Pro Glu Gln Gly His Phe Leu Trp Ile Ala Ala Val Leu
                85                  90                  95

Val Met Phe Val Val Phe Cys Gly Met Val Ser Phe Lys Thr Leu Arg
            100                 105                 110

Lys Arg Lys Lys Lys Gln Pro Gly Pro Ser His Glu Cys Glu Thr Ile
        115                 120                 125

Lys Arg Glu Arg Lys Glu Ser Lys Gln Thr Asn Glu Arg Val Pro Tyr
130                 135                 140

His Val Pro Glu Arg Ser Asp Glu Ala Gln Cys Ile Asn Ile Leu Lys
145                 150                 155                 160

Thr Ala Ser Gly Asp Lys Ser Thr Thr
                165

<210> SEQ ID NO 32
<211> LENGTH: 509
<212> TYPE: DNA
<213> ORGANISM: Felis catus

<400> SEQUENCE: 32
tgtgtagtac ttttgtcgcc tgaggctgtc ttcaaaatgt taatacactg ggcttcatca    60
gatctctcag gtacgtggta tggtactctt tcgttggtct gtttgctctc tttctctcc   120 cttttgatgg tttcacattc atgagagggg ccaggctgct tcttcttcct tttccttagt   180
gttttaaagg acaccatccc acaaaaaaca acaaacatta caagtacagc cgcaatccag   240
aggaagtggc cttgttcagg gtctttatcc ttaggttgtg catctatatt gaaaggtagg   300
gagagcagca tctccagtgt ctccagtttc agggcacaaa agacgctcac attgtgtgct   360
tcagggactg aaaaaggcaa gctgatagaa acgttgtaca gttctgtcac attattttga   420
gatttcttca tgacagtatc atacttagta gttgaattct cagtgtttag ctgaaaatac   480
atctccttag gttctgggta accttgtat                                     509

<210> SEQ ID NO 33
<211> LENGTH: 359
<212> TYPE: DNA
<213> ORGANISM: Felis catus
<220> FEATURE:
<221> NAME/KEY: CDS
<222> LOCATION: (1)..(357)

<400> SEQUENCE: 33 ata caa ggt tac cca gaa cct aag gag atg tat ttt cag cta aac act    48
Ile Gln Gly Tyr Pro Glu Pro Lys Glu Met Tyr Phe Gln Leu Asn Thr
1               5                   10                  15

```
gag aat tca act act aag tat gat act gtc atg aag aaa tct caa aat      96
Glu Asn Ser Thr Thr Lys Tyr Asp Thr Val Met Lys Lys Ser Gln Asn
             20                  25                  30 aat gtg aca gaa ctg tac aac gtt tct atc agc ttg cct ttt tca gtc     144
Asn Val Thr Glu Leu Tyr Asn Val Ser Ile Ser Leu Pro Phe Ser Val
         35                  40                  45 cct gaa gca cac aat gtg agc gtc ttt tgt gcc ctg aaa ctg gag aca     192
Pro Glu Ala His Asn Val Ser Val Phe Cys Ala Leu Lys Leu Glu Thr
 50                  55                  60 ctg gag atg ctg ctc tcc cta cct ttc aat ata gaa acc atc aaa agg     240
Leu Glu Met Leu Leu Ser Leu Pro Phe Asn Ile Glu Thr Ile Lys Arg
 65                  70                  75                  80 gag aga aaa gag agc aaa cag acc aac gaa aga gta cca tac cac gta     288
Glu Arg Lys Glu Ser Lys Gln Thr Asn Glu Arg Val Pro Tyr His Val
                 85                  90                  95 cct gag aga tct gat gaa gcc cag tgt att aac att ttg aag aca gcc     336
Pro Glu Arg Ser Asp Glu Ala Gln Cys Ile Asn Ile Leu Lys Thr Ala
            100                 105                 110 tca ggc gac aaa agt act aca ca                                      359
Ser Gly Asp Lys Ser Thr Thr
        115
```

<210> SEQ ID NO 34
<211> LENGTH: 119
<212> TYPE: PRT
<213> ORGANISM: Felis catus

<400> SEQUENCE: 34

```
Ile Gln Gly Tyr Pro Glu Pro Lys Glu Met Tyr Phe Gln Leu Asn Thr
 1               5                  10                  15

Glu Asn Ser Thr Thr Lys Tyr Asp Thr Val Met Lys Lys Ser Gln Asn
             20                  25                  30

Asn Val Thr Glu Leu Tyr Asn Val Ser Ile Ser Leu Pro Phe Ser Val
         35                  40                  45

Pro Glu Ala His Asn Val Ser Val Phe Cys Ala Leu Lys Leu Glu Thr
 50                  55                  60

Leu Glu Met Leu Leu Ser Leu Pro Phe Asn Ile Glu Thr Ile Lys Arg
 65                  70                  75                  80

Glu Arg Lys Glu Ser Lys Gln Thr Asn Glu Arg Val Pro Tyr His Val
                 85                  90                  95

Pro Glu Arg Ser Asp Glu Ala Gln Cys Ile Asn Ile Leu Lys Thr Ala
            100                 105                 110

Ser Gly Asp Lys Ser Thr Thr
        115
```

<210> SEQ ID NO 35
<211> LENGTH: 359
<212> TYPE: DNA
<213> ORGANISM: Felis catus

<400> SEQUENCE: 35

```
tgtgtagtac ttttgtcgcc tgaggctgtc ttcaaaatgt taatacactg ggcttcatca     60
gatctctcag gtacgtggta tggtactctt tcgttggtct gtttgctctc ttttctctcc    120
cttttgatgg tttctatatt gaaaggtagg gagagcagca tctccagtgt ctccagtttc    180
agggcacaaa agacgctcac attgtgtgct tcagggactg aaaaaggcaa gctgatagaa    240
acgttgtaca gttctgtcac attattttga gatttcttca tgacagtatc atacttagta    300
gttgaattct cagtgtttag ctgaaaatac atctccttag gttctgggta accttgtat     359
```

<210> SEQ ID NO 36
<211> LENGTH: 594
<212> TYPE: DNA
<213> ORGANISM: Felis catus
<220> FEATURE:
<221> NAME/KEY: CDS
<222> LOCATION: (1)..(522)

<400> SEQUENCE: 36

```
atg ggt cac gca gca aag tgg aaa aca cca cta ctg aag cac cca tat      48
Met Gly His Ala Ala Lys Trp Lys Thr Pro Leu Leu Lys His Pro Tyr
 1               5                  10                  15 ccc aag ctc ttt ccg ctc ttg atg cta gct agt ctt ttt tac ttc tgt      96
Pro Lys Leu Phe Pro Leu Leu Met Leu Ala Ser Leu Phe Tyr Phe Cys
             20                  25                  30 tca ggt atc atc cag gtg aac aag aca gtg gaa gaa gta gca gta cta     144
Ser Gly Ile Ile Gln Val Asn Lys Thr Val Glu Glu Val Ala Val Leu
         35                  40                  45 tcc tgt gat tac aac att tcc acc aaa gaa ctg acg gaa att cga atc     192
Ser Cys Asp Tyr Asn Ile Ser Thr Lys Glu Leu Thr Glu Ile Arg Ile
     50                  55                  60 tat tgg caa aag gat gat gaa atg gtg ttg gct gtc atg tct ggc aaa     240
Tyr Trp Gln Lys Asp Asp Glu Met Val Leu Ala Val Met Ser Gly Lys
 65                  70                  75                  80 gta caa gtg tgg ccc aag tac aag aac cgc aca ttc act gac gtc acc     288
Val Gln Val Trp Pro Lys Tyr Lys Asn Arg Thr Phe Thr Asp Val Thr
                 85                  90                  95 gat aac cac tcc att gtg atc atg gct ctg cgc ctg tca gac aat ggc     336
Asp Asn His Ser Ile Val Ile Met Ala Leu Arg Leu Ser Asp Asn Gly
            100                 105                 110 aaa tac act tgt att att caa aag att gaa aaa ggg tct tac aaa gtg     384
Lys Tyr Thr Cys Ile Ile Gln Lys Ile Glu Lys Gly Ser Tyr Lys Val
        115                 120                 125 aaa cac ctg act tcg gtg atg tta ttg gtc aga ggc gtc aca ccc agc     432
Lys His Leu Thr Ser Val Met Leu Leu Val Arg Gly Val Thr Pro Ser
    130                 135                 140 aca gag ccc aat gcc cat gcg gag ctt gaa atc atg acc ctg aga tca     480
Thr Glu Pro Asn Ala His Ala Glu Leu Glu Ile Met Thr Leu Arg Ser
145                 150                 155                 160 aga cct gag ctg aga tca aga gtc gga cgc tta atc gac tga             522
Arg Pro Glu Leu Arg Ser Arg Val Gly Arg Leu Ile Asp
                165                 170 gccacccagg catcccaatg atactttcta aataaactct taaaaaaaaa aaaaaaaaaa   582
aaaaaaaaaa aa                                                        594
```

<210> SEQ ID NO 37
<211> LENGTH: 173
<212> TYPE: PRT
<213> ORGANISM: Felis catus

<400> SEQUENCE: 37

```
Met Gly His Ala Ala Lys Trp Lys Thr Pro Leu Leu Lys His Pro Tyr
 1               5                  10                  15

Pro Lys Leu Phe Pro Leu Leu Met Leu Ala Ser Leu Phe Tyr Phe Cys
             20                  25                  30

Ser Gly Ile Ile Gln Val Asn Lys Thr Val Glu Glu Val Ala Val Leu
         35                  40                  45

Ser Cys Asp Tyr Asn Ile Ser Thr Lys Glu Leu Thr Glu Ile Arg Ile
     50                  55                  60
```

```
Tyr Trp Gln Lys Asp Asp Glu Met Val Leu Ala Val Met Ser Gly Lys
 65                  70                  75                  80

Val Gln Val Trp Pro Lys Tyr Lys Asn Arg Thr Phe Thr Asp Val Thr
                 85                  90                  95

Asp Asn His Ser Ile Val Ile Met Ala Leu Arg Leu Ser Asp Asn Gly
            100                 105                 110

Lys Tyr Thr Cys Ile Ile Gln Ile Glu Lys Gly Ser Tyr Lys Val
        115                 120                 125

Lys His Leu Thr Ser Val Met Leu Leu Val Arg Gly Val Thr Pro Ser
    130                 135                 140

Thr Glu Pro Asn Ala His Ala Glu Leu Glu Ile Met Thr Leu Arg Ser
145                 150                 155                 160

Arg Pro Glu Leu Arg Ser Arg Val Gly Arg Leu Ile Asp
                165                 170
```

```
<210> SEQ ID NO 38
<211> LENGTH: 594
<212> TYPE: DNA
<213> ORGANISM: Felis catus

<400> SEQUENCE: 38
tttttttttt tttttttttt tttttttttt taagagttta tttagaaagt atcattggga      60
tgcctgggtg gctcagtcga ttaagcgtcc gactcttgat ctcagctcag gtcttgatct     120
cagggtcatg atttcaagct ccgcatgggc attgggctct gtgctgggtg tgacgcctct     180
gaccaataac atcaccgaag tcaggtgttt cactttgtaa gaccctttt  caatcttttg     240
aataatacaa gtgtatttgc cattgtctga caggcgcaga gccatgatca caatggagtg     300
gttatcggtg acgtcagtga atgtgcggtt cttgtacttg gccacactt  gtactttgcc     360
agacatgaca gccaacacca tttcatcatc cttttgccaa tagattcgaa tttccgtcag     420
ttctttggtg gaaatgttgt aatcacagga tagtactgct acttcttcca ctgtcttgtt     480
cacctggatg atacctgaac agaagtaaaa aagactagct agcatcaaga gcggaaagag     540
cttgggatat gggtgcttca gtagtggtgt tttccacttt gctgcgtgac ccat           594
```

```
<210> SEQ ID NO 39
<211> LENGTH: 519
<212> TYPE: DNA
<213> ORGANISM: Felis catus

<400> SEQUENCE: 39
atgggtcacg cagcaaagtg gaaaacacca ctactgaagc acccatatcc caagctcttt      60
ccgctcttga tgctagctag tcttttttac ttctgttcag gtatcatcca ggtgaacaag     120
acagtggaag aagtagcagt actatcctgt gattacaaca tttccaccaa agaactgacg     180
gaaattcgaa tctattggca aaaggatgat gaaatggtgt tggctgtcat gtctggcaaa     240
gtacaagtgt ggcccaagta caagaaccgc acattcactg acgtcaccga taaccactcc     300
attgtgatca tggctctgcg cctgtcagac aatggcaaat acacttgtat tattcaaaag     360
attgaaaaag ggtcttacaa agtgaaacac ctgacttcgg tgatgttatt ggtcagaggc     420
gtcacaccca gcacagagcc caatgcccat gcggagcttg aaatcatgac cctgagatca     480
agacctgagc tgagatcaag agtcggacgc ttaatcgac                            519
```

```
<210> SEQ ID NO 40
<211> LENGTH: 519
```

```
<212> TYPE: DNA
<213> ORGANISM: Felis catus

<400> SEQUENCE: 40
gtcgattaag cgtccgactc ttgatctcag ctcaggtctt gatctcaggg tcatgatttc        60
aagctccgca tgggcattgg gctctgtgct gggtgtgacg cctctgacca ataacatcac       120
cgaagtcagg tgtttcactt tgtaagaccc ttttcaatc ttttgaataa acaagtgta        180 tttgccattg tctgacaggc gcagagccat gatcacaatg gagtggttat cggtgacgtc       240
agtgaatgtg cggttcttgt acttgggcca cacttgtact ttgccagaca tgacagccaa       300
caccatttca tcatcctttt gccaatagat tcgaatttcc gtcagttctt tggtggaaat       360
gttgtaatca caggatagta ctgctacttc ttccactgtc ttgttcacct ggatgatacc       420
tgaacagaag taaaaaagac tagctagcat caagagcgga aagagcttgg gatatgggtg       480
cttcagtagt ggtgttttcc actttgctgc gtgacccat                              519

<210> SEQ ID NO 41
<211> LENGTH: 1856
<212> TYPE: DNA
<213> ORGANISM: Canis familiaris
<220> FEATURE:
<221> NAME/KEY: CDS
<222> LOCATION: (60)..(731)

<400> SEQUENCE: 41
caggatcctg aaaggtttca ctctgcttcc tgaagacctg aacactgctc cataaagcc         59 atg gct ggc ttt gga ttc cgg agg cat ggg gct cag ccg gac ctg gct        107
Met Ala Gly Phe Gly Phe Arg Arg His Gly Ala Gln Pro Asp Leu Ala
 1               5                  10                  15 tct agg acc tgg ccc tgc act gct ctg ttt tct ctt ctc ttt atc ccc        155
Ser Arg Thr Trp Pro Cys Thr Ala Leu Phe Ser Leu Leu Phe Ile Pro
             20                  25                  30 gtc ttc tcc aaa ggg atg cat gtg gct cag cct gca gtg gtt ctg gcc        203
Val Phe Ser Lys Gly Met His Val Ala Gln Pro Ala Val Val Leu Ala
         35                  40                  45 agc agc cgg ggt gtt gct agc ttc gtg tgt gaa tat ggg tct tca ggc        251
Ser Ser Arg Gly Val Ala Ser Phe Val Cys Glu Tyr Gly Ser Ser Gly
     50                  55                  60 aac gca gcc gag gtc cgg gtg aca gtg ctg cgg cag gct ggc agc cag        299
Asn Ala Ala Glu Val Arg Val Thr Val Leu Arg Gln Ala Gly Ser Gln
 65                  70                  75                  80 atg act gaa gtc tgt gcc gcg aca tac aca gtg gag gat gag ttg gcc        347
Met Thr Glu Val Cys Ala Ala Thr Tyr Thr Val Glu Asp Glu Leu Ala
                 85                  90                  95 ttc ctg gat gat tct acc tgc acc ggc acc tcc agt gga aac aaa gtg        395
Phe Leu Asp Asp Ser Thr Cys Thr Gly Thr Ser Ser Gly Asn Lys Val
            100                 105                 110 aac ctc acc atc caa ggg ttg agg gcc atg gac acg ggg ctc tac atc        443
Asn Leu Thr Ile Gln Gly Leu Arg Ala Met Asp Thr Gly Leu Tyr Ile
        115                 120                 125 tgc aag gtg gag ctc atg tac cca cca ccc tac tat gta ggc atg gga        491
Cys Lys Val Glu Leu Met Tyr Pro Pro Pro Tyr Tyr Val Gly Met Gly
    130                 135                 140 aat gga acc cag att tat gtc atc gat cct gaa cct tgc cca gat tct        539
Asn Gly Thr Gln Ile Tyr Val Ile Asp Pro Glu Pro Cys Pro Asp Ser
145                 150                 155                 160 gac ttc ctc ctc tgg atc ctt gca gca gtc agt tcg ggc ttg ttt ttt        587
Asp Phe Leu Leu Trp Ile Leu Ala Ala Val Ser Ser Gly Leu Phe Phe
                165                 170                 175
```

```
tat agc ttt ctt atc aca gct gtt tct ttg agc aaa atg cta aag aaa       635
Tyr Ser Phe Leu Ile Thr Ala Val Ser Leu Ser Lys Met Leu Lys Lys
            180                 185                 190 aga agc cct ctt acc aca ggg gtc tat gtg aaa atg ccc cca act gag       683
Arg Ser Pro Leu Thr Thr Gly Val Tyr Val Lys Met Pro Pro Thr Glu
            195                 200                 205 cca gaa tgt gaa aag caa ttt cag cct tat ttt att ccc atc aat tga       731
Pro Glu Cys Glu Lys Gln Phe Gln Pro Tyr Phe Ile Pro Ile Asn
        210                 215                 220 gagatcatta tgaagaagaa agaatatttt ccaatttcca ggagctgagg caattctaac     791
tttgtgctat ccagctatgt gtacttgttt gtatattttg gggggggttt catctctctt     851
taatataaag ctggatgcag aacccaaatg aagtgtacta caaattcaaa gcaaaggtgc     911
aagaaaacag agccaggatg tttctgtcac atcagatcca attttcgtaa agtatcact      971
tgggagcaat atgggatgc agcattagga catgcgctct aggatatagg ttagggagtg     1031
gtgcggtcca agaaagcaa aggagagaga gtcagggaga ggatgatatt gtacacactt     1091
tgtatttaca tgtgagaagt ttatagctga agtgacgttt tcaagttaaa ttttttgtgct    1151
atgttatttt tcataaatgt aaaatcacgt gaagacttta aaaatattca catggctata    1211
ttttagccag tgattccaaa ggttgtattg taccaatata tatttttta tctgatagta    1271
ttatgcatgg gggccacatg tgcttttgtg tatttgttga tggtttcaat ataaacacta    1331
tatggcagtg tcttcccacc agggggctcag ggggaagtttt atggagggat tcaggacact    1391
aatacgccag gtaaaataca aggtcacttg gtaactggct tggaaactgg atgaggtcat    1451
agttgattct tgtagacgtg ttgggctaaa ttggtgttga catgtgcttt gggcttttat    1511
gttagctcct ttcaaagatt tgtaagggag tcaaaactgg tatatctgat ttaactccat    1571
agaacaccat cgtcaagtaa acggctcatt ccaggagtct tggaggtatg aacttcaagg    1631
aagctctagt ttcacaaggg ccccaattcc ttgctcatgg ttaatgccat gggcagaaaa    1691
cagcagcagg tggcagaaca gggtgatgaa ggtttccgaa acaaacact gttggtgttt     1751
ttttaactca ctatttctg tgaaaatgca acaacatgta taatatttt aattaaataa     1811
aaatctgtgg tggtcattaa aaaaaaaaaa aaaaaaaaa aaaaa                      1856
```

<210> SEQ ID NO 42
<211> LENGTH: 223
<212> TYPE: PRT
<213> ORGANISM: Canis familiaris

<400> SEQUENCE: 42

```
Met Ala Gly Phe Gly Phe Arg Arg His Gly Ala Gln Pro Asp Leu Ala
  1               5                  10                  15

Ser Arg Thr Trp Pro Cys Thr Ala Leu Phe Ser Leu Leu Phe Ile Pro
                 20                  25                  30

Val Phe Ser Lys Gly Met His Val Ala Gln Pro Ala Val Leu Ala
             35                  40                  45

Ser Ser Arg Gly Val Ala Ser Phe Val Cys Glu Tyr Gly Ser Ser Gly
         50                  55                  60

Asn Ala Ala Glu Val Arg Val Thr Val Leu Arg Gln Ala Gly Ser Gln
 65                  70                  75                  80

Met Thr Glu Val Cys Ala Ala Thr Tyr Thr Val Glu Asp Glu Leu Ala
                 85                  90                  95

Phe Leu Asp Asp Ser Thr Cys Thr Gly Thr Ser Ser Gly Asn Lys Val
                100                 105                 110
```

```
Asn Leu Thr Ile Gln Gly Leu Arg Ala Met Asp Thr Gly Leu Tyr Ile
            115                 120                 125
Cys Lys Val Glu Leu Met Tyr Pro Pro Tyr Tyr Val Gly Met Gly
        130                 135                 140
Asn Gly Thr Gln Ile Tyr Val Ile Asp Pro Glu Pro Cys Pro Asp Ser
145                 150                 155                 160
Asp Phe Leu Leu Trp Ile Leu Ala Ala Val Ser Ser Gly Leu Phe Phe
                165                 170                 175
Tyr Ser Phe Leu Ile Thr Ala Val Ser Leu Ser Lys Met Leu Lys Lys
            180                 185                 190
Arg Ser Pro Leu Thr Thr Gly Val Tyr Val Lys Met Pro Pro Thr Glu
            195                 200                 205
Pro Glu Cys Glu Lys Gln Phe Gln Pro Tyr Phe Ile Pro Ile Asn
        210                 215                 220

<210> SEQ ID NO 43
<211> LENGTH: 1856
<212> TYPE: DNA
<213> ORGANISM: Canis familiaris

<400> SEQUENCE: 43
```

| | | | | | |
|---|---|---|---|---|---|
| tttttttttt | tttttttttt | ttttttttaat | gaccaccaca | gatttttatt | taattaaaaa | 60 |
| tattatacat | gttgttgcat | tttcacagaa | aatagtgagt | taaaaaaaca | ccaacagtgt | 120 |
| ttgttttcgg | aaaccttcat | caccctgttc | tgccacctgc | tgctgttttc | tgcccatggc | 180 |
| attaaccatg | agcaaggaat | tggggccctt | gtgaaactag | agcttccttg | aagttcatac | 240 |
| ctccaagact | cctggaatga | gccgtttact | tgacgatggt | gttctatgga | gttaaatcag | 300 |
| ataccagt | tttgactccc | ttacaaatct | tgaaaggag | ctaacataaa | agcccaaagc | 360 |
| acatgtcaac | accaatttag | cccaacacgt | ctacaagaat | caactatgac | ctcatccagt | 420 |
| ttccaagcca | gttaccaagt | gaccttgtat | tttacctggc | gtattagtgt | cctgaatccc | 480 |
| tccataaaac | ttcccctgag | cccctggtgg | aagacactg | ccatatagtg | tttatattga | 540 |
| aaccatcaac | aaatacacaa | agcacatgt | ggccccatg | cataatacta | tcagataaaa | 600 |
| aaatatat | tggtacaata | caacctttgg | aatcactggc | taaatatag | ccatgtgaat | 660 |
| atttttaaag | tcttcacgtg | attttacatt | tatgaaaaat | aacatagcac | aaaaatttaa | 720 |
| cttgaaaacg | tcacttcagc | tataaacttc | tcacatgtaa | atacaaagtg | tgtacaatat | 780 |
| catcctctcc | ctgactctct | ctcctttgct | ttctttggac | cgcaccactc | cctaacctat | 840 |
| atcctagagc | gcatgtccta | atgctgcatc | cccatattgc | tcccaagtga | tacttttacg | 900 |
| aaaattggat | ctgatgtgac | agaaacatcc | tggctctgtt | tcttgcacc | tttgctttga | 960 |
| atttgtagta | cacttcattt | gggttctgca | tccagcttta | tattaaagag | agatgaaacc | 1020 |
| ccccccaaaa | tatacaaaca | agtacacata | gctggatagc | acaaagttag | aattgcctca | 1080 |
| gctcctggaa | attggaaaat | attctttctt | cttcataatg | atctctcaat | tgatgggaat | 1140 |
| aaaataaggc | tgaaattgct | tttcacattc | tggctcagtt | gggggcattt | tcacatagac | 1200 |
| ccctgtggta | agagggcttc | tttctttag | cattttgctc | aaagaaacag | ctgtgataag | 1260 |
| aaagctataa | aaaacaagc | ccgaactgac | tgctgcaagg | atccagagga | ggaagtcaga | 1320 |
| atctgggcaa | ggttcaggat | cgatgacata | aatctgggtt | ccatttccca | tgcctacata | 1380 |
| gtagggtggt | gggtacatga | gctccacctt | gcagatgtag | agcccccgtgt | ccatggcccct | 1440 |
| caaccccttgg | atggtgaggt | tcactttgtt | tccactggag | gtgccggtgc | aggtagaatc | 1500 |

```
atccaggaag gccaactcat cctccactgt gtatgtcgcg gcacagactt cagtcatctg    1560
gctgccagcc tgccgcagca ctgtcacccg gacctcggct gcgttgcctg aagacccata    1620
ttcacacacg aagctagcaa cacccgggct gctggccaga accactgcag gctgagccac    1680
atgcatccct ttggagaaga cggggataaa gagaagagaa aacagagcag tgcagggcca    1740
ggtcctagaa gccaggtccg gctgagcccc atgcctccgg aatccaaagc cagccatggc    1800
tttatggagc agtgttcagg tcttcaggaa gcagagtgaa acctttcagg atcctg         1856

<210> SEQ ID NO 44
<211> LENGTH: 669
<212> TYPE: DNA
<213> ORGANISM: Canis familiaris

<400> SEQUENCE: 44
atggctggct ttggattccg gaggcatggg gctcagccgg acctggcttc taggacctgg     60
ccctgcactg ctctgttttc tcttctcttt atccccgtct tctccaaagg gatgcatgtg    120
gctcagcctg cagtggttct ggccagcagc cggggtgttg ctagcttcgt gtgtgaatat    180
gggtcttcag gcaacgcagc cgaggtccgg gtgacagtgc tgcggcaggc tggcagccag    240
atgactgaag tctgtgccgc gacatacaca gtggaggatg agttggcctt cctggatgat    300
tctacctgca ccggcaccctc cagtggaaac aaagtgaacc tcaccatcca agggttgagg    360
gccatggaca cggggctcta catctgcaag gtggagctca tgtacccacc accctactat    420
gtaggcatgg gaaatggaac ccagatttat gtcatcgatc ctgaaccttg cccagattct    480
gacttcctcc tctggatcct tgcagcagtc agttcgggct tgtttttta tagcttttctt   540 atcacagctg tttctttgag caaaatgcta aagaaaagaa gccctcttac acagggggtc    600
tatgtgaaaa tgcccccaac tgagccagaa tgtgaaaagc aatttcagcc ttattttatt    660
cccatcaat                                                            669

<210> SEQ ID NO 45
<211> LENGTH: 669
<212> TYPE: DNA
<213> ORGANISM: Canis familiaris

<400> SEQUENCE: 45
attgatggga ataaaataag gctgaaattg cttttcacat tctggctcag ttggggggcat    60 tttcacatag acccctgtgg taagagggct tcttttcttt agcattttgc tcaaagaaac    120
agctgtgata agaaagctat aaaaaaacaa gcccgaactg actgctgcaa ggatccagag    180
gaggaagtca gaatctgggc aaggttcagg atcgatgaca taaatctggg ttccatttcc    240
catgcctaca tagtaggggtg gtgggtacat gagctccacc ttgcagatgt agagccccgt    300
gtccatggcc ctcaacccctt ggatggtgag gttcactttg tttccactgg aggtgccggt    360
gcaggtagaa tcatccagga aggccaactc atcctccact gtgtatgtcg cggcacagac    420
ttcagtcatc tggctgccag cctgccgcag cactgtcacc cggacctcgg ctgcgttgcc    480
tgaagaccca tattcacaca cgaagctagc aacaccccgg ctgctggcca gaaccactgc    540
aggctgagcc acatgcatcc ctttggagaa gacggggata agagaagag aaaacagagc    600 agtgcagggc caggtcctag aagccaggtc cggctgagcc ccatgcctcc ggaatccaaa    660
gccagccat                                                           669

<210> SEQ ID NO 46
```

```
<211> LENGTH: 1883
<212> TYPE: DNA
<213> ORGANISM: Felis catus
<220> FEATURE:
<221> NAME/KEY: CDS
<222> LOCATION: (69)..(740)

<400> SEQUENCE: 46
```

| | |
|---|---:|
| caaagcttca ggatcctgaa aggtttcact ctgcttcctg aagacctgaa cactgctccc | 60 |
| ataaagcc atg gct tgc ttt gga ttc cgg agg cat ggg gct cag ctg gac<br>         Met Ala Cys Phe Gly Phe Arg Arg His Gly Ala Gln Leu Asp<br>          1           5                 10 | 110 |
| ctg gct tct agg acc tgg ccc tgc act gct ctg ttt tct ctt ctc ttt<br>Leu Ala Ser Arg Thr Trp Pro Cys Thr Ala Leu Phe Ser Leu Leu Phe<br> 15                  20              25              30 | 158 |
| atc ccc gtc ttc tcc aaa ggg atg cat gtg gcc cag cct gca gtg gtg<br>Ile Pro Val Phe Ser Lys Gly Met His Val Ala Gln Pro Ala Val Val<br>                35              40              45 | 206 |
| ctg gcc agc agc cga ggt gtc gcc agc ttc gtg tgt gaa tat ggg tct<br>Leu Ala Ser Ser Arg Gly Val Ala Ser Phe Val Cys Glu Tyr Gly Ser<br>        50              55              60 | 254 |
| tca ggc aat gcc gcc gaa gtc cga gtg act gtg ctg agg cag act ggc<br>Ser Gly Asn Ala Ala Glu Val Arg Val Thr Val Leu Arg Gln Thr Gly<br>     65               70              75 | 302 |
| agc cag atg act gaa gtc tgt gct gca aca tac aca gtg gag aat gag<br>Ser Gln Met Thr Glu Val Cys Ala Ala Thr Tyr Thr Val Glu Asn Glu<br> 80                  85              90 | 350 |
| ttg gcc ttc cta gat gat tcc acc tgc act ggc atc tcc agc gga aac<br>Leu Ala Phe Leu Asp Asp Ser Thr Cys Thr Gly Ile Ser Ser Gly Asn<br> 95               100            105            110 | 398 |
| aaa gtg aac ctc acc atc caa ggg ttg agg gcc atg gac acg gga ctc<br>Lys Val Asn Leu Thr Ile Gln Gly Leu Arg Ala Met Asp Thr Gly Leu<br>                115            120            125 | 446 |
| tac atc tgc aag gtg gag ctc atg tac cca cca ccc tac tat gca ggc<br>Tyr Ile Cys Lys Val Glu Leu Met Tyr Pro Pro Pro Tyr Tyr Ala Gly<br>        130              135              140 | 494 |
| atg ggc aat gga acc cag att tat gtc atc gat cct gaa cct tgc cca<br>Met Gly Asn Gly Thr Gln Ile Tyr Val Ile Asp Pro Glu Pro Cys Pro<br>              145            150            155 | 542 |
| gat tct gac ttc ctc ctc tgg atc ctc gca gca gtc agt tca gga ttg<br>Asp Ser Asp Phe Leu Leu Trp Ile Leu Ala Ala Val Ser Ser Gly Leu<br>        160              165              170 | 590 |
| ttt ttt tat agc ttc ctt atc aca gct gtt tct ttg agc aaa atg cta<br>Phe Phe Tyr Ser Phe Leu Ile Thr Ala Val Ser Leu Ser Lys Met Leu<br>175               180            185            190 | 638 |
| aag aaa aga agc cct ctt act aca ggg gtc tat gtg aaa atg ccc cca<br>Lys Lys Arg Ser Pro Leu Thr Thr Gly Val Tyr Val Lys Met Pro Pro<br>              195            200            205 | 686 |
| aca gag cca gaa tgt gaa aag caa ttt cag cct tat ttt att ccc atc<br>Thr Glu Pro Glu Cys Glu Lys Gln Phe Gln Pro Tyr Phe Ile Pro Ile<br>        210            215              220 | 734 |
| aat tga cacaccgtta tgaagaagga agaacactgt ccaatttcta agagctgagg<br>Asn | 790 |
| caattctaac ttttgctat ccagctatgt tgcttatttg tgtatttggg gggggattc | 850 |
| atctctcttt aatataaagc tggatgcaaa atccagatga agtgtactac aatttgaagc | 910 |
| aaaggtgcag gaaaacagag ccaggatgtt tctgtcacat cagatccaat tttagtaaaa | 970 |
| gcatcactcg ggagcaatat agggatgcag tcttacgttg taggtgaagg atatgggtta | 1030 |
| gggggtggtg ctgtccaaag aatacaaagg aagagagtta gggagaggat gatattgtac | 1090 |

-continued

```
acactttgta tttacacatg agaagtttat agctgaagtg atgttttcaa gttaaagttt    1150
tgtgctgtta tttttcttaa atgtggaatt acatgaagac tttaaaaata ctcacgtggc    1210
tatattttag ccagtgattc caaaggttgt attgtaccaa tatgtatttt tttttatttg    1270
atagtattgt gcatggggac cacatgtgct tttgtgtatt tgctgatggt tttaatataa    1330
acactatatg gcagtgtctt cccaccatgg gttcagggga agttttatgg aggggctcag    1390
gacactaata caccaggtag aacacaaagt cacttggtaa ctggcttgga aactggctga    1450
ggtcataact gattcttata gacacgttga gctgaattgg tgttgacatg tgatttgggc    1510
ttttatgtta gctcctttca aaggtttgca agggagtcca gactggtgta tctgatgtaa    1570
ttcaatagaa caccaacctc aagaaaatgg ctcactccag gggtcttgta ggtacgaact    1630
tcaaggaagc tctagtttca caagggcccc aattcctaac acatggttca tgccatggac    1690
agaaaaaagc agccggtggc agaacggggt gatgaaagtt tctaaaaact aacactgttg    1750
gtgtttttta actcattatt ttccatgaaa atgcaacaac atgtataata tttttaatta    1810
aataaaaatc tgtggtggtc aaaaaaaaaa aaaaaaaaaa aaaaaaaaaa aaaaaaaaaa    1870
aaaaaaaaaa aaa                                                       1883
```

<210> SEQ ID NO 47
<211> LENGTH: 223
<212> TYPE: PRT
<213> ORGANISM: Felis catus

<400> SEQUENCE: 47

```
Met Ala Cys Phe Gly Phe Arg Arg His Gly Ala Gln Leu Asp Leu Ala
  1               5                  10                  15

Ser Arg Thr Trp Pro Cys Thr Ala Leu Phe Ser Leu Leu Phe Ile Pro
                 20                  25                  30

Val Phe Ser Lys Gly Met His Val Ala Gln Pro Ala Val Val Leu Ala
             35                  40                  45

Ser Ser Arg Gly Val Ala Ser Phe Val Cys Glu Tyr Gly Ser Ser Gly
         50                  55                  60

Asn Ala Ala Glu Val Arg Val Thr Val Leu Arg Gln Thr Gly Ser Gln
 65                  70                  75                  80

Met Thr Glu Val Cys Ala Ala Thr Tyr Thr Val Glu Asn Glu Leu Ala
                 85                  90                  95

Phe Leu Asp Asp Ser Thr Cys Thr Gly Ile Ser Ser Gly Asn Lys Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Ala Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Ile Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 48
<211> LENGTH: 1883
<212> TYPE: DNA
<213> ORGANISM: Felis catus

<400> SEQUENCE: 48

```
tttttttttt tttttttttt tttttttttt tttttttttt tttttttttt tttgaccacc      60
acagatttt atttaattaa aaatattata catgttgttg cattttcatg gaaaataatg      120
agttaaaaaa caccaacagt gttagttttt agaaactttc atcaccccgt tctgccaccg      180
gctgctttt tctgtccatg gcatgaacca tgtgttagga attggggccc ttgtgaaact      240
agagcttcct tgaagttcgt acctacaaga cccctggagt gagccatttt cttgaggttg      300
gtgttctatt gaattacatc agatacacca gtctggactc ccttgcaaac ctttgaaagg      360
agctaacata aagcccaaa tcacatgtca acaccaattc agctcaacgt gtctataaga      420
atcagttatg acctcagcca gtttccaagc cagttaccaa gtgactttgt gttctacctg      480
gtgtattagt gtcctgagcc cctccataaa acttcccctg aacccatggt gggaagacac      540
tgccatatag tgtttatatt aaaccatca gcaaatacac aaaagcacat gtggtcccca      600
tgcacaatac tatcaaataa aaaaaaatac atattggtac aatacaacct ttggaatcac      660
tggctaaaat atagccacgt gagtattttt aaagtcttca tgtaattcca catttaagaa      720
aaataacagc acaaaacttt aacttgaaaa catcacttca gctataaact tctcatgtgt      780
aaatacaaag tgtgtacaat atcatcctct ccctaactct cttccttgt attctttgga      840
cagcaccacc ccctaaccca tatccttcac ctacaacgta agactgcatc cctatattgc      900
tcccgagtga tgcttttact aaaattggat ctgatgtgac agaaacatcc tggctctgtt      960
ttcctgcacc tttgcttcaa attgtagtac acttcatctg gattttgcat ccagctttat     1020
attaaagaga gatgaatccc cccccaaaat acacaaataa gcaacatagc tggatagcaa     1080
aaagttagaa ttgcctcagc tcttagaaat tggacagtgt tcttccttct tcataacggt     1140
gtgtcaattg atgggaataa aataaggctg aaattgcttt tcacattctg gctctgttgg     1200
gggcattttc acatagaccc ctgtagtaag agggcttctt ttctttagca ttttgctcaa     1260
agaaacagct gtgataagga agctataaaa aaacaatcct gaactgactg ctgcgaggat     1320
ccagaggagg aagtcagaat ctgggcaagg ttcaggatcg atgacataaa tctgggttcc     1380
attgcccatg cctgcatagt agggtggtgg gtacatgagc tccaccttgc agatgtagag     1440
tcccgtgtcc atggccctca acccttggat ggtgaggttc actttgtttc cgctggagat     1500
gccagtgcag gtggaatcat ctaggaaggc caactcattc tccactgtgt atgtcgcagc     1560
acagacttca gtcatctggc tgccagtctg cctcagcaca gtcactcgga cttcggcggc     1620
attgcctgaa gacccatatt cacacacgaa gctggcgaca cctcggctgc tggccagcac     1680
cactgcaggc tgggccacat gcatcccttt ggagaagacg gggataaaga gaagagaaaa     1740
cagagcagtg cagggccagg tcctagaagc caggtccagc tgagccccat gcctccggaa     1800
tccaaagcaa gccatggctt tatgggagca gtgttcaggt cttcaggaag cagagtgaaa     1860
cctttcagga tcctgaagct ttg                                              1883
```

<210> SEQ ID NO 49
<211> LENGTH: 669
<212> TYPE: DNA
<213> ORGANISM: Felis catus

<400> SEQUENCE: 49

```
atggcttgct ttggattccg gaggcatggg gctcagctgg acctggcttc taggacctgg      60
ccctgcactg ctctgttttc tcttctcttt atccccgtct tctccaaagg gatgcatgtg     120
gcccagcctg cagtggtgct ggccagcagc cgaggtgtcg ccagcttcgt gtgtgaatat     180
gggtcttcag gcaatgccgc cgaagtccga gtgactgtgc tgaggcagac tggcagccag     240
atgactgaag tctgtgctgc gacatacaca gtggagaatg agttggcctt cctagatgat     300
tccacctgca ctggcatctc cagcggaaac aaagtgaacc tcaccatcca agggttgagg     360
gccatggaca cgggactcta catctgcaag gtggagctca tgtacccacc ccctactat      420
gcaggcatgg gcaatggaac ccagatttat gtcatcgatc ctgaaccttg cccagattct     480
gacttcctcc tctggatcct cgcagcagtc agttcaggat tgttttttta tagcttcctt     540
atcacagctg tttctttgag caaaatgcta agaaaagaa gccctcttac tacagggtc      600
tatgtgaaaa tgcccccaac agagccagaa tgtgaaaagc aatttcagcc ttattttatt     660
cccatcaat                                                              669
```

<210> SEQ ID NO 50
<211> LENGTH: 669
<212> TYPE: DNA
<213> ORGANISM: Felis catus

<400> SEQUENCE: 50

```
attgatggga ataaaataag gctgaaattg cttttcacat tctggctctg ttgggggcat      60
tttcacatag accctgtag taagagggct tcttttcttt agcattttgc tcaaagaaac      120
agctgtgata aggaagctat aaaaaaacaa tcctgaactg actgctgcga ggatccagag     180
gaggaagtca gaatctgggc aaggttcagg atcgatgaca taaatctggg ttccattgcc     240
catgcctgca tagtagggtg gtgggtacat gagctccacc ttgcagatgt agagtcccgt     300
gtccatggcc ctcaacccctt ggatggtgag gttcactttg tttccgctgg agatgccagt    360
gcaggtggaa tcatctagga aggccaactc attctccact gtgtatgtcg cagcacagac     420
ttcagtcatc tggctgccag tctgcctcag cacagtcact cggacttcgg cggcattgcc     480
tgaagaccca tattcacaca cgaagctggc gacacctcgg ctgctggcca gcaccactgc     540
aggctgggcc acatgcatcc ctttggagaa gacggggata aagagaagag aaaacagagc     600
agtgcagggc caggtcctag aagccaggtc cagctgagcc ccatgcctcc ggaatccaaa     660
gcaagccat                                                              669
```

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51

```
atacaaggtt acccagaacc                                                   20
```

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 52
tgtgtagtac ttttgtcgcc                                               20

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 53
gggaattcgc caccatgggt cacgcagcaa agtg                               34

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 54
ccctcgagct atgtagacag gtgagatc                                      28

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 55
gtaatacgac tcactatagg gc                                            22

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 56
accactccat tgtgatcatg                                               20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
gtcttgatct cagggtcatg                                               20

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 58

```
gcggatccac catgggcatt tgtgacagca c                              31
```

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 59

```
gcctcgagtt aaaaatgtgt agtacttttg tcg                            33
```

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 60

```
gtgaacctsa cyatccaagg                                           20
```

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 61

```
gcattttcac atagacccct g                                         21
```

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 62

```
ggtacgtagg gatgcatgtg gctcagc                                   27
```

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 63

```
ccgaattctc agtcagaatc tgggcaaggt tc                             32
```

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 64

```
ggtacgtagg tgctgcttcc atgaagag                                          28

<210> SEQ ID NO 65
<211> LENGTH: 35
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 65
cccctaggtt aaaactgtgt agtactgttg tcgcc                                  35
```